United States Patent
Nishikawa et al.

(10) Patent No.: US 6,713,473 B1
(45) Date of Patent: Mar. 30, 2004

(54) TRICYCLIC COMPOUNDS

(75) Inventors: Naoyuki Nishikawa, Minami-ashigara (JP); Masaharu Sugai, Minami-ashigara (JP); Kozo Aoki, Odawara (JP); Makoto Suzuki, Minami-ashigara (JP); Akihiko Ikegawa, Ishehara (JP); Kazunobu Takahashi, Minami-ashigara (JP); Fukuichi Ohsawa, Yokohama (JP); Naomi Masuda, Tokyo (JP); Nobukazu Kakui, Kawasaki (JP); Jiro Tanaka, Yokohama (JP); Yuji Tabata, Yokohama (JP); Kenji Asai, Tokyo (JP)

(73) Assignee: Meiji Seika Kaisha, Ltd., Tokyo (JP)

( * ) Notice: Subject to any disclaimer, the term of this patent is extended or adjusted under 35 U.S.C. 154(b) by 0 days.

(21) Appl. No.: 09/926,355

(22) PCT Filed: Apr. 20, 2000

(86) PCT No.: PCT/JP00/02573
§ 371 (c)(1),
(2), (4) Date: Feb. 19, 2002

(87) PCT Pub. No.: WO00/63171
PCT Pub. Date: Oct. 26, 2000

(30) Foreign Application Priority Data

Apr. 20, 1999 (JP) .......................... 11-111698
Jul. 14, 1999 (JP) .......................... 11-200228

(51) Int. Cl.[7] .............. A61K 31/403; A61P 43/00; C07D 209/88; C07F 9/572
(52) U.S. Cl. .............. 514/217.08; 514/228.8; 514/231.5; 514/323; 514/339; 514/385; 514/383; 514/254.08; 544/142; 544/360; 544/333; 544/61; 544/372; 546/200; 546/267.7; 548/449; 548/311.4; 548/266.4; 548/146; 540/602
(58) Field of Search .............. 548/449, 311.4, 548/266.4, 146; 514/411, 323, 339, 231.5, 385, 383, 217.08, 365, 228.8, 254.08; 546/200, 267.7; 544/360, 142, 61, 333, 372; 540/602

(56) References Cited

U.S. PATENT DOCUMENTS

| | | |
|---|---|---|
| 3,932,456 A | 1/1976 | Albrecht et al. |
| 5,391,556 A | 2/1995 | Heckel et al. |
| 5,602,024 A | 2/1997 | Gerald et al. |
| 5,708,187 A | 1/1998 | Flaugh et al. |
| 5,814,653 A | 9/1998 | Flaugh et al. |
| 5,892,041 A * | 4/1999 | Yuan et al. .................. 544/372 |

FOREIGN PATENT DOCUMENTS

| | | |
|---|---|---|
| CA | 1299577 | 4/1992 |
| EP | 00555824 | 8/1993 |
| EP | 0749962 | 12/1996 |
| EP | 00882726 | 12/1998 |
| JP | 48-54061 | 7/1973 |
| JP | 54-17932 | 2/1979 |
| JP | 8-301846 | 11/1996 |
| JP | 9-157253 | 6/1997 |
| WO | 92/15590 | 9/1992 |
| WO | 94/14773 | 7/1994 |
| WO | 95/04720 | 2/1995 |
| WO | 96/16542 | 6/1996 |
| WO | 97/09308 | 3/1997 |
| WO | 97/19682 | 6/1997 |
| WO | 97/20820 | 6/1997 |
| WO | 97/20821 | 6/1997 |
| WO | 97/20822 | 6/1997 |
| WO | 97/20823 | 6/1997 |
| WO | 97/40017 | 10/1997 |
| WO | 97/46250 | 12/1997 |
| WO | 98/01417 | 1/1998 |
| WO | 98/06402 | 2/1998 |
| WO | 98/06717 | 2/1998 |
| WO | 98/11895 | 3/1998 |

(List continued on next page.)

OTHER PUBLICATIONS

Brunton, et al, J. CHem. Soc. (1956), 4783–4785.*
GRammaticakis Compt. Rend. (1960), 251, 2728–30.*
English Language Abstract of JP 8–301846.

(List continued on next page.)

Primary Examiner—Joseph K. McKane
Assistant Examiner—Andrea D. Small
(74) Attorney, Agent, or Firm—Greenblum & Bernstein, P.L.C.

(57) ABSTRACT

A compound represented by the formula (I) [A represents a 5- to 7-membered hydrocarbon ring group; L represents $-NR^3-CO-$, $-CO-NR^3-$ and the like ($R^3$ represents a hydrogen atom, a lower alkyl group, a lower acyl group and the like); M represents an alkylene linking group (a carbon atom constituting the carbon chain may be replaced with a nitrogen atom, an oxygen atom and the like); X represents $-S-$, $-O-$, $-NR^4-$, $-NR^5-CO-$ and the like ($R^4$ and $R^5$ represent a hydrogen atom, a lower alkyl group and the like) or a single bond; Y represents an alkyl group, an aryl group, an amino group, an aromatic heterocyclic group and the like; $R^1$ represents a lower alkyl group, a lower alkenyl group, a lower alkynyl group or a lower acyl group; and $R^{21}$, $R^{22}$ and $R^{23}$ represent a hydrogen atom, a hydroxyl group, a lower alkyl group and the like] or a salt thereof. The compound is useful as an active ingredient of medicaments for diseases in which neuropeptide Y is involved, ingestion control for hyperphagia and the like.

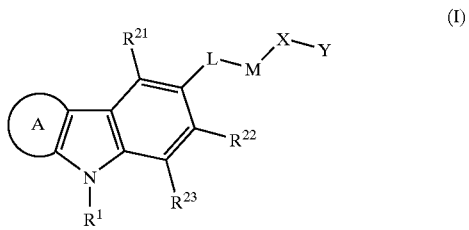

(I)

27 Claims, No Drawings

FOREIGN PATENT DOCUMENTS

| | | |
|---|---|---|
| WO | 98/24768 | 6/1998 |
| WO | 98/25907 | 6/1998 |
| WO | 98/25908 | 6/1998 |
| WO | 98/27063 | 6/1998 |
| WO | 98/35944 | 8/1998 |
| WO | 98/35957 | 8/1998 |
| WO | 98/40356 | 9/1998 |
| WO | 98/47505 | 10/1998 |
| WO | 99/27965 | 6/1999 |

OTHER PUBLICATIONS

English Language Abstract of JP 54–17932.
English Language Abstract of JP 9–157253.
Tachimoto et al., Nature, 296, p. 659 (1982).
International Journal of Obesity, 19, p. 517 (1995).
Endocrinology, 133, p. 1753 (1993).
British Journal of Pharmacology, 95, p. 419 (1988).
FEBS Letter, vol. 271, p. 81 (1990).
Journal of Biological Chemistry, vol. 270, p. 22661 (1995).
Journal of Biological Chemistry, vol. 270, p. 26762 (1995).
Nature, vol. 382, p. 168, (1996).
Trends in Pharmacological Sciences, vol. 15, p. 153 (1994).
C. R. Heb. Seances Acad. Sic., 251, p. 2728, 1960.
J. Pharmacol. Exptl. Therap., 99, p. 450, 1950.
Journal of Chemical Society, p. 833 (1924).
Journal of Medicinal Chemistry (J. Med. Chem., 36, p. 272 (1993)).
Journal of Chemical Society, p. 809 (1926).
Tetrahedron, vol. 48, No. 11, p. 1999 (1992).
Journal of Heterocycle Chemistry, 27, p. 147 (1990).
Chemical Abstracts, vol. 55, Col. 18702, e (RN=102659–65–4).
Journal of Medicinal Chemistry, 40, p. 2643–2652, 1997.
Heterocycles, 45, p. 585–596, 1997.

* cited by examiner

TRICYCLIC COMPOUNDS

TECHINCAL FIELD

The present invention relates to a tricyclic compound useful in the pharmaceutical field and a medicament comprising the compound as an active ingredient.

BACKGROUND ART

Neuropeptide Y (hereinafter occasionally abbreviated as "NPY" in the specification) is a peptide consisting of 36 amino acid residues, and first isolated from swine brain by Tachimoto et al. in 1982 [Nature, 296, p.659 (1982)]. NPY was revealed to be classified into the pancreatic polypeptides (PP) family based on the homology of primary amino acid sequence. As polypeptides belonging to this family, pancreatic polypeptides (PP) produced in pancreatic endocrine system cells and peptides YY (PYY) produced in endocrine system cells of the digestive tract are known. All of these peptides of the PP family consist of 36 amino acid residues and a carboxy terminal (C-terminal) sequence consisting of several amino acid residues is well conserved among them. In particular, in all of the polypeptides, the C-terminal amino acid (36th amino acid: Y36) is tyrosine. For this reason, receptors for the peptides of the PP family are referred to as Y-type receptors. It has also found that the Y type receptors are seven transmembrane-type receptors conjugated with G protein.

NPY is widely distributed over the central nervous system and the peripheral nervous system, and it bears various functions in living bodies as one of the peptides existing in the nervous systems in largest amounts. For example, NPY is involved in control of blood pressure, control of ingestion behavior, control of intestinal function, control of circadian rhythm, suppressive control of insulin secretion, suppression of secretion of hormones such as prolactin, lutenizing hormone, adrenocorticotropic hormone, gonadotropin releasing hormone and vasopressin, and the like. It is known that, when NPY is continuously administered into a ventricle, obesity and insulin resistance are induced based on these actions. NPY is also involved in control of emotion, functions of the central autonomic nervous system and the like.

Furthermore, NPY coexists with norepinephrine at terminals of sympathetic nerves, and is involved in tonicity of sympathetic nerves. It is known that peripheral administration of NPY causes vasoconstriction and enhances actions of other vasoconstrictors such as norepinephrine [International Journal of Obesity], 19, p.517 (1995); Endocrinology, 133, p.1753 (1993); British Journal of Pharmacology, 95, p.419 (1998)].

The function of NPY is expressed when it binds to a Y-type receptor for NPY which exists in the central or peripheral nervous system. As the NPY receptor, at least six kinds of subtypes have been recognized so far, and genes encoding the receptors have been isolated except for Y3. Y1 is the first cloned receptor [FEBS Letter, 271, p.81 (1990)], and the receptor mainly distributes in vessels in the peripheral system and is involved in vasoconstriction (increase of blood pressure). In the central system, the receptor mainly distributes in cerebral cortex, thalamus and amygdaloid corpus, and it is considered that anxiety action is expressed in amygdaloid corpus through the Y1 receptor.

Y2 receptor was first classified as a pharmacologically different receptor from the Y1 receptor, and its existence was clarified by isolation of its gene [J. Biol. Chem., 270, p.22661 (1995)]. The expression site of this receptor is mainly brain. The receptor is localized in, in particular, cerebral cortex, hippocampus, amygdaloid corpus and the like, whilst the receptor has not been found in cerebellum or spinal marrow. Y3 receptor has been pharmacologically classified, however, its gene has not yet been isolated. Y4 receptor was found by using human Y1 receptor cDNA as probe, and its gene was isolated [J. Biol. Chem., 270, p.26762 (1995)]. Its expression is specifically limited to prostate, colon, pancreas and small intestine, and the receptor has not found in brain, kidney, lung, heart, spleen and the like.

It has long been suggested that other NPY receptor subtype may exist in hypothalamus, which has ligand affinity similar to that of the Y1 receptor and controls ingestion behavior, and Gerald et al. successfully cloned Y5 receptor that controlled ingestion from a rat hypothalamus cDNA library [Nature, 382, p.168 (1996)]. The Y5 receptor has low homology of 35% or less to the other NPY receptors. Its expression site is limited to cerebral hypothalamus, and the receptor is mostly involved in control of ingestion. Y6 receptor is found only in mouse, and the receptor does not function in human as its gene is a pseudogene.

A substance that has affinity for these Y-type receptors and acts as an agonist or antagonist for the receptors can control expression of actions of NPY. A substance having such properties is expected to be useful in prophylactic or therapeutic treatment of various kinds of diseases in which NPY is involved, for example, cardiovascular diseases such as hypertension, kidney diseases, heart diseases and vascular spasm, central system diseases such as hyperphagia, melancholia, epilepsy and dementia, metabolic diseases such as obesity, diabetes mellitus, hyperlipidemia and hormone abnormality, inappetence of cancer patients, glaucoma and the like [Trends in Pharmacological Sciences], 15, p.153 (1994)].

In particular, it is expected that a substance that has selective affinity to the Y5 receptor (also referred to as "NPY/Y5 receptor" hereinafter in the specification) among the NPY receptors is useful for prophylatic and/or therapeutic treatment of diseases in which the NPY/Y5 receptor is involved, and can be used without a risk of side effects of enhancing or antagonizing other Y-type receptors. Since the Y5 receptor is mostly involved in the control of ingestion, it is considered that the substance can be used as an ingestion controlling agent for hyperphagia and inappetence of cancer patients, for example, and can also be used for prophylactic or therapeutic treatment of central system diseases such as melancholia, epilepsy and dementia, metabolic diseases such as obesity, diabetes mellitus, hyperlipidemia and hormone abnormality and the like.

The gene coding for the NPY/Y5 receptor and applications thereof are disclosed in U.S. Pat. No. 5,602,024, International Patent Publication WO96/16542 and WO97/46250. However, these publications do not specifically disclose nor suggest the compounds of the present invention.

As antagonists against the NPY/Y5 receptor, aryl sulfonamide and sulfamide derivatives are disclosed in WO97/19682, quinazoline derivatives are disclosed in WO97/20820, WO97/20821, WO97/20822 and WO97/20823, amide derivatives are disclosed in WO98/35944 and WO98/35957, aminopyridine derivatives are disclosed in WO98/40356, pyrazole derivatives are disclosed in WO98/24768, WO98/25907, WO98/25908 and WO98/27063, xanthene derivatives are disclosed in WO98/47505 and the like. However, these publications do not specifically disclose nor suggest the compounds of the present invention. WO99/27965 discloses that NPY/Y5 receptor antagonists are useful for prophylactic or therapeutic treatment of hypercholesterolemia, hyperlipidemia or arteriosclerosis.

Compounds which structurally relates to the compounds represented by the general formula (I) or the general formula (IV) of the present invention are described in European Patent Publication EP882726, WO98/01417, WO97/40017, Japanese Patent Unexamined Publication (Kokai) Nos. 8-301846, 54-017932, 48-054061, WO95/04720, Canadian Patent No. 1,299,577, WO92/15590, WO98/06717, WO94/14773, U.S. Pat. No. 3,932,456. However, these publications do not disclose NPY antagonism of the respective disclosed compounds, and do not specifically disclose nor suggest the compounds newly provided by the inventor of the present invention.

Compounds which structurally relates to the compounds represented by the general formula (XXI) of the present invention are described in WO98/11895, WO98/06402, EP 749 962, U.S. Pat. Nos. 5,708,187, 5,814,653, C. R. Heb. Seances Acad. Sic., 251, p.2728, 1960 and J. Pharmacol. Exptl. Therap., 99, p.450, 1950. However, these publications do not specifically disclose nor suggest the compounds of the present invention and the NPY antagonism thereof.

DISCLOSURE OF THE INVENTION

An object of the present invention is to provide a substance having affinity for the NPY receptors, in particular a substance having selective affinity to the NPY/Y5 receptor. Another object of the present invention is to provide a medicament having a controlling action of ingestion and is useful as, for example, an ingestion controlling agent for hyperphagia and inappetence of cancer patients. Still another object of the present invention is to provide a medicament useful for prophylactic or therapeutic treatment of central system diseases such as melancholia, epilepsy and dementia, metabolic diseases such as obesity, diabetes mellitus, hyperlipidemia and hormone abnormality and the like.

The inventors of the present invention conducted various studies to achieve the aforementioned objects. As a result, they found that novel compounds represented by the following general formula (I) had affinity for the NPY receptors and controlling action of expression of the action of NPY. Moreover, they also found that compounds represented by the following general formula (IV) also had the same action. Furthermore, they found that these substances have selective affinity particularly to the NPY/Y5 receptor, and that these substances were useful as a medicament for ingestion control and prophylactic or therapeutic treatment of the aforementioned diseases. The present invention was achieved on the basis of these findings.

That is, the present invention provides compounds represented by the following general formula (I):

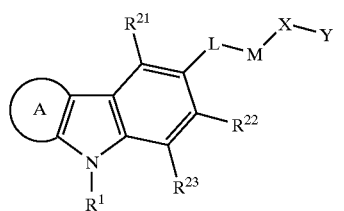

(I)

[in the formula, A represents a 5- to 7-membered hydrocarbonic ring group (wherein the ring may have one or more substituents selected from the group consisting of a hydroxyl group, a lower alkyl group, a lower acyl group, a lower alkoxy group and a halogen atom, and wherein the lower alkyl group, the lower acyl group and the lower alkoxy group may have one or more substituents);

L represents a linking group selected from the group consisting of —NR$^3$—CO—, —CO—NR$^3$—, —NR$^3$—CS—, —CS—NR$^3$—, —NR$^3$—SO$_2$— and —SO$_2$—NR$^3$— (in the formulas, R$^3$ represents a hydrogen atom, a lower alkyl group or a lower acyl group, wherein the lower alkyl group and the lower acyl group may have one or more substituents);

M represents an alkylene linking group having 2 to 10 carbon atoms [the alkylene linking group may have one or more substituents, and the carbon atoms constituting the carbon chain of the alkylene linking group (except for at least one carbon atom) may be replaced with a nitrogen atom, an oxygen atom, a sulfur atom or a 3- to 8-membered cycloalkylene group, wherein the nitrogen atom may be substituted with a lower alkyl group or a lower acyl group, and the cycloalkylene group may have one or more substituents], provided that M may be a single bond when L represents —NR$^3$—CO—;

X represents a linking group selected from the group consisting of —S—, —O—, —NR$^4$—, —NR$^5$—CO—, —NR$^5$—CS— or —NR$^5$—SO$_2$— (in the formulas, R$^4$ represents a hydrogen atom, an alkyl group or a lower acyl group, wherein the alkyl group and the lower acyl group may have one or more substituents, and the alkyl group may contain a ring structure, R$^5$ represents a hydrogen atom, a lower alkyl group or a lower acyl group, wherein the lower alkyl group and lower acyl group may have one or more substituents, and R$^4$ may bond to M to form a ring) or a single bond, provided that X represents —NR$^4$— when M represents a single bond (wherein R$^4$ represents a hydrogen atom or an alkyl group, and wherein the alkyl group may contain a ring structure and may have one or more substituents), and X represents a linking group selected from the group consisting of —NR$^5$—CO—, —NR$^5$—CS— and —NR$^5$—SO$_2$— mentioned above (in the formulas, R$^5$ has the same meaning as that defined above) when A represents a benzene ring;

Y represents a substituent selected from the group consisting of an alkyl group having 1 to 20 carbon atoms (said alkyl group may contain a ring structure), an aryl group having 6 to 12 carbon atoms, an amino group, a monoalkylamino group having 1 to 8 carbon atoms, a dialkylamino group having 2 to 16 carbon atoms, an azacycloalkyl group having 4 to 8 carbon atoms, a phosphoryl group, a monoalkylphosphoryl group having 1 to 8 carbon atoms, a dialkylphosphoryl group having 2 to 16 carbon atoms, an aromatic heterocyclic group and a 5- to 7-membered non-aromatic heterocyclic group (said groups may further have one or more substituents, and may bind to R$^5$ to form a ring), provided that Y represents an aromatic heterocyclic group or a 5- to 7-membered non-aromatic heterocyclic group when X represents a single bond, and R$^4$ and Y may bind to each other to form a ring together with the nitrogen atom to which they bind when M represents a single bond (the ring may contain one or more hetero atoms as ring-constituting atoms in addition to the nitrogen atom bound with R$^4$ and Y, and may have one or more substituents);

R$^1$ represents substituent selected from the group consisting of a lower alkyl group, a lower alkenyl group, a lower alkynyl group and a lower acyl group (said groups may contain a ring structure, and may have one or more substituents); and R$^{21}$, R$^{22}$ and R$^{23}$ each independently represent a substituent selected from the group consisting of a hydrogen atom, a hydroxyl group, a lower alkyl group, a lower acyl group, a lower alkoxy group, a halogen atom, an amino group, a mono (lower alkyl)amino group, a di(lower alkyl)amino group, a lower acylamino group and an amido group (the substituent may have one or more substituents)] and salts thereof.

According to a preferred embodiment of the present invention, in the aforementioned general formula (I), A represents a 5- to 7-membered hydrocarbon ring (the ring may have one or more substituents selected from the group consisting of a hydroxyl group, a lower alkyl group, a lower acyl group, a lower alkoxy group and a halogen atom, wherein the lower alkyl group, the lower acyl group and the lower alkoxy group may have one or more substituents);

L represents a linking group selected from the group consisting of —NR$^3$—CO—, —CO—NR$^3$—, —NR$^3$—CS—, —CS—NR$^3$—, —NR$^3$—SO$_2$— and —SO$_2$—NR$^3$— (in the formulas, R$^3$ represents a hydrogen atom, a lower alkyl group or a lower acyl group, wherein the lower alkyl group and the lower acyl group may have one or more substituents);

M represents an alkylene linking group having 2 to 10 carbon atoms [the alkylene linking group may have one or more substituents, and the carbon atoms constituting the carbon chain of the alkylene linking group (except for at least one carbon atom) may be replaced with a nitrogen atom, an oxygen atom, a sulfur atom or a 3- to 8-membered cycloalkylene group, wherein the nitrogen atom may be substituted with a lower alkyl group or a lower acyl group, and the cycloalkylene group may have one or more substituents];

X represents a linking group selected from the group consisting of —S—, —O—, —NR$^4$—, —NR$^5$—CO—, —NR$^5$—CS— and —NR$^5$—SO$_2$— (in the formulas, R$^4$ and R$^5$ each independently represent a hydrogen atom, a lower alkyl group or a lower acyl group, wherein the lower alkyl group and lower acyl group may have one or more substituents, and R$^4$ may bind to M to form a ring) or a single bond, provided that X represents a linking group selected from the group consisting of —NR$^5$—CO—, —NR$^5$—CS— and —NR$^5$—SO$_2$— mentioned above (in the formulas, R$^5$ has the same meaning as that defined above) when A represents a benzene ring;

Y represents a substituent selected from the group consisting of an alkyl group having 1 to 12 carbon atoms, an aryl group having 6 to 12 carbon atoms, an amino group, a monoalkylamino group having 1 to 8 carbon atoms, a dialkylamino group having 2 to 16 carbon atoms, an azacycloalkyl group having 4 to 8 carbon atoms, a phosphoryl group, a monoalkylphosphoryl group having 1 to 8 carbon atoms, a dialkylphosphoryl group having 2 to 16 carbon atoms, an aromatic heterocyclic group and a 5- to 7-membered non-aromatic heterocyclic group (said groups may further have one or more substituents, and may bind to R$^5$ to form a ring), provided that Y represents an aromatic heterocyclic group or a 5- to 7-membered non-aromatic heterocyclic group when X represents a single bond;

R$^1$ represents a substituent selected from the group consisting of a lower alkyl group, a lower alkenyl group, a lower alkynyl group and a lower acyl group (said groups may contain a ring structure, and may have one or more substituents); and R$^{21}$, R$^{22}$ and R$^{23}$ each independently represent a substituent selected from the group consisting of a hydrogen atom, a hydroxyl group, a lower alkyl group, a lower acyl group, a lower alkoxy group, a halogen atom, an amino group, a mono(lower alkyl)amino group, a di(lower alkyl)amino group, a lower acylamino group and an amido group (the substituent may have one or more substituents).

In the aforementioned preferred embodiment, preferred compounds are those wherein A is a hydrocarbon ring group represented by the following formula (Ia), (Ib) or (Ic):

(Ia)

(Ib)

(Ic)

(the rings may have one or more substituents selected from the group consisting of a hydroxyl group, a lower alkyl group, a lower acyl group, a lower alkoxy group and a halogen atom, wherein the lower alkyl group, the lower acyl group and the lower alkoxy group may have one or more substituents) and salts thereof; and A is preferably a benzene ring (the benzene ring may have one or more substituents selected from the group consisting of a hydroxyl group, a lower alkyl group, a lower acyl group, a lower alkoxy group and a halogen atom, wherein the lower alkyl group, the lower acyl group and the lower alkoxy group may have one or more substituents). Furthermore, according to further preferred embodiments, there are provided compounds represented by the aforementioned general formula (I) and salts thereof, wherein L is —NR$^3$—CO— and X is —NR$^5$—CO— or —NR$^5$—SO$_2$—; and compounds represented by the aforementioned general formula (I) and salts thereof, wherein L is —CO—NR$^3$— and X is —NR$^5$—CO— or —NR$^5$—SO$_2$—.

Further, as a preferred embodiment falling within the scope of the aforementioned general formula (I), there are provided compounds represented by the following general formula (XXI):

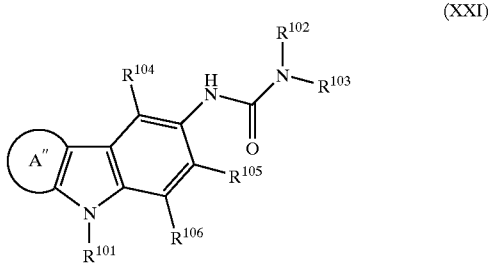
(XXI)

[in the formula, A" represents a 5- to 7-membered hydrocarbon ring group (the ring may have one or more substituents selected from the group consisting of a lower alkyl group, a lower alkoxy group and a halogen atom, wherein the lower alkyl group and the lower alkoxy group may have one or more substituents);

$R^{101}$ represents a lower alkyl group or a lower acyl group (the lower alkyl group and the lower acyl group may contain a ring structure, and may have one or more substituents);

$R^{102}$ represents a hydrogen atom or an alkyl group having 1 to 20 carbon atoms in total (the alkyl group may contain a ring structure, and may have one or more substituents);

$R^{103}$ represents an alkyl group having 1 to 20 carbon atoms in total (the alkyl group may contain a ring structure, and may have one or more substituents), and $R^{102}$ and $R^{103}$ may bind to each other to form a ring with the nitrogen atom to which they bind (the ring may contain one or more hetero atoms as ring constituting atoms in addition to the nitrogen atom to which $R^{102}$ and $R^{103}$ bind, and may have one or more substituents on the ring); and $R^{104}$, $R^{105}$ and $R^{106}$ each independently represent a substituent selected from the group consisting of a hydrogen atom, a hydroxyl group, a lower alkyl group, a lower acyl group, a lower alkoxy group, a halogen atom, an amino group, a mono(lower alkyl)amino group, a di(lower alkyl) amino group, a lower acylamino group and an amido group (the substituent may have one or more substituents) and salts thereof.

According to a preferred embodiment of the above invention, there are provided compounds represented by the aforementioned general formula (XXI) wherein A" is a hydrocarbon ring group represented by the following formula (Ia), (Ib) or (Ic):

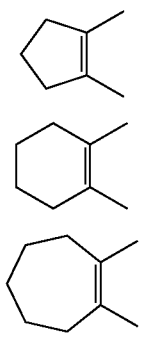

(Ia)

(Ib)

(Ic)

(the rings may have one or more substituents selected from the group consisting of a lower alkyl group, a lower alkoxy group and a halogen atom, wherein the lower alkyl group and lower alkoxy group may have one or more substituents) and salts thereof.

According to further preferred embodiments of the compounds represented by the aforementioned general formula (XXI) and salt thereof, there are provided compounds represented by the aforementioned general formula (XXI) wherein $R^{101}$ is a lower alkyl group (the alkyl group may contain a ring structure, and may have one or more substituents) and salts thereof; compounds represented by the aforementioned general formula (XXI) wherein $R^{103}$ is an alkyl group having one or more substituents containing one or more hetero atoms selected from the group consisting of a nitrogen atom, an oxygen atom and a sulfur atom, and salts thereof; and compounds represented by the aforementioned general formula (XXI) wherein the substituent on the alkyl group represented by $R^{103}$ is selected from the group consisting of a hydroxyl group, an amino group, a cyano group, a carbamoyl group, a sulfamoyl group, a lower alkoxy group, a lower alkylthio group, a lower alkylsulfonylamino group, a lower alkylcarbonylamino group, a hydroxyalkyl group, a hydroxyalkyloxy group, an alkoxyalkyloxy group, a monoalkylamino group, a dialkylamino group, a lower alkylsulfonylaminoalkoxy group, a lower alkylcarbonylaminoalkoxy group, a lower alkylsulfonylaminoalkylthio group, a lower alkylcarbonylaminoalkylthio group, a tetrazolyl group, a triazolyl group, an imidazolyl group, a pyridyl group, a morpholinyl group, a morpholino group, a thiomorpholino group, a piperazino group, a piperazinyl group, a piperidino group, a piperidinyl group, a pyrrolidinyl group, a triazolylthio group and an imidazolylthio group, and salts thereof.

Furthermore, according to a further preferred embodiment, there are provided compounds represented by the aforementioned general formula (XXI) wherein the ring formed by $R^{102}$ and $R^{108}$ bound to each other together with the nitrogen atom to which they bind is a ring represented by the following general formula (XXII):

(XXII)

[in the formula, X represents —$CH_2$—, —O—, —S—, —NH— or —$NR^{108}$— [(in the formula, $R^{108}$ represents a lower alkyl group, a lower acyl group, a phenyl group or a heterocyclic group (the lower alkyl group, the lower acyl group, the phenyl group and the heterocyclic group may have one or more substituents)];

n represents an integer of 1 to 4;

$R^{107}$ represents a hydroxyl group, an amino group, a cyano group, a lower alkyl group, a lower alkoxy group, a lower alkylthio group, a lower alkylcarbonyl group (the lower alkyl group, the lower alkoxy group, the lower alkylthio group and the lower, alkylcarbonyl group may contain a ring structure, and may have one or more substituents), an aryl group (the aryl group may have one or more substituents) or a heterocyclic group;

m represents an integer of 0 to 4, and when two or more of $R^{107}$ exist, respective $R^{107}{}_s$ are independent and may be the same or different] and salts thereof; and compounds represented by the aforementioned general formula (XXI) wherein X is —$CH_2$—, —O— or —S— and salts thereof.

The compounds represented by the aforementioned general formula (I) and salts thereof have affinity for the NPY receptors, in particular, act as a ligand of the NPY/Y5 receptor, and can control the expression of the action of NPY. Therefore, the compounds represented by the aforementioned general formula (I) and salt thereof are useful for prophylactic and/or therapeutic treatment of diseases in which NPY is involved, especially diseases in which the NPY/Y5 receptor is involved.

According to the present invention, there are thus provided medicaments comprising as an active ingredient a substance selected from the group consisting of the compounds represented by the aforementioned general formula (I) and physiologically acceptable salts thereof and hydrates thereof and solvates thereof. The aforementioned medicaments are useful as, for example, medicaments for controlling ingestion, medicaments for prophylactic and/or therapeutic treatment of diabetes or medicaments for prophylactic and/or therapeutic treatment of hypercholesterolemia, hyperlipidemia or arteriosclerosis. There are also provided use of a substance selected from the group consisting of the compounds represented by the aforementioned general formula (I) and physiologically acceptable salts thereof, and hydrates thereof and solvates thereof for manufacture of the aforementioned medicaments; methods for controlling ingestion, which comprise a step of administering an effective amount of a substance selected from the group consisting of the compounds represented by the aforementioned general formula (I) and physiologically acceptable salts thereof, and hydrates thereof and solvates thereof to a mammal including human; and methods for prophylactic and/or therapeutic treatment of diseases in which NPY is involved, which comprise a step of administering an effective amount of a substance selected from the group consisting of the compounds represented by the aforementioned general formula (I) and physiologically acceptable salts thereof, and hydrates thereof and solvates thereof to a mammal including human.

As another aspect, the present invention provides ligands for NPY receptors comprising as an active ingredient a compound represented by the following general formula (IV):

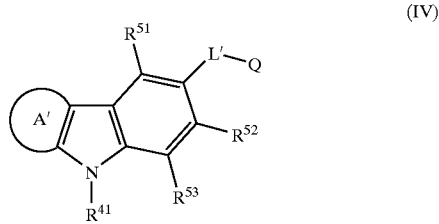

(IV)

[in the formula, A' represents a 5- to 7-membered hydrocarbon ring group (the ring may have one or more substituents selected from the group consisting of a hydroxyl group, a lower alkyl group, a lower acyl group, a lower alkoxy group, a halogen atom, an amino group, a mono(lower alkyl)amino group, a di(lower alkyl)amino group, a lower acylamino group and an amido group, wherein the lower alkyl group, the lower acyl group and the lower alkoxy group may have one or more substituents);

L' represents a linking group selected from the group consisting of —NR$^{63}$—CO—, —CO—NR$^{53}$—, —NR$^{63}$—CS—, —CS—NR$^{63}$—, —NR$^{63}$—SO$_2$— and —SO$_2$—NR$^{63}$— (in the formulas, R$^{63}$ represents a hydrogen atom, a lower alkyl group or a lower acyl group, wherein the lower alkyl group and the lower acyl group may have one or more substituents);

Q represents a substituent selected from the group consisting of an alkyl group, an alkenyl group, an alkynyl group, an alkylalkenyl group, a cycloalkyl group, an alkylcycloalkylalkyl group, an aryl group, a heterocyclic group, an alkylcycloalkyl group, a cycloalkylalkyl group and an alkylazacycloalkyl group (the substituent may have one or more substituents);

R$^{41}$ represents a substituent selected from the group consisting of a lower alkyl group, a lower alkenyl group, a lower alkynyl group and a lower acyl group (the substituent may contain a ring structure, and may have one or more substituents); and R$^{51}$, R$^{52}$ and R$^{53}$ each independently represent a substituent selected from the group consisting of a hydrogen atom, a hydroxyl group, a lower alkyl group, a lower acyl group, a lower alkoxy group, a halogen atom, an amino group, a mono(lower alkyl)amino group, a di(lower alkyl)amino group, a lower acylamino group and an amido group (the substituent may have one or more substituents)] or a physiologically acceptable salt thereof. According to a preferred embodiment of this invention, there are provided the aforementioned ligands of NPY receptors wherein L' is —CONR$^{53}$—.

As a further aspect, the present invention provides medicaments for controlling ingestion, which comprise as an active ingredient a substance selected from the group consisting of the compounds represented by the aforementioned general formula (IV) and physiologically acceptable salts thereof, and hydrates thereof and solvates thereof, and medicaments for prophylactic and/or therapeutic treatment of diabetes or medicaments for prophylactic and/or therapeutic treatment of hypercholesterolemia, hyperlipidemia or arteriosclerosis, which comprise the aforementioned substance as an active ingredient. There are further provided use of a substance selected from the group consisting of the compounds represented by the aforementioned general formula (IV) and physiologically acceptable salts thereof, and hydrates thereof and solvates thereof for manufacture of the aforementioned medicaments; methods for controlling ingestion which comprise a step of administering an effective amount of a substance selected from the group consisting of the compounds represented by the aforementioned general formula (IV) and physiologically acceptable salts thereof, and hydrates thereof and solvates thereof to a mammal including human; and methods for therapeutic and/or prophylactic treatment of diseases in which NPY is involved, which comprise a step of administering an effective amount of a substance selected from the group consisting of the compounds represented by the aforementioned general formula (IV) and physiologically acceptable salts thereof, and hydrates thereof and solvates thereof to a mammal including human.

BEST MODE FOR CARRYING OUT THE INVENTION

Definitions of the terms used in this specification are as follows.

An "alkyl group" or an alkyl portion of substituents having the alkyl portion (for example, an alkoxy group, a monoalkylamino group, a dialkylamino group and the like) may be any of linear, branched, cyclic or a combination thereof unless otherwise specifically mentioned. The cyclic alkyl group may be a polycyclic alkyl group. As the alkyl group, a $C_1$–$C_{20}$ alkyl group, preferably a $C_1$–$C_{12}$ alkyl group, more preferably a $C_1$–$C_8$ alkyl group, further preferably a $C_1$–$C_8$ alkyl group, and most preferably a $C_1$–$C_4$ alkyl group may be used.

When the term "lower" is used for a substituent, the term means that the substituent has 1 to 7, preferably 1 to 5, and most preferably 1 to 4 carbon atoms unless otherwise specifically mentioned. For example, examples of the lower alkyl group include methyl group, ethyl group, n-propyl group, isopropyl group, cyclopropyl group, n-butyl group, sec-butyl group, tert-butyl group, cyclobutyl group, cyclopropylmethyl group, n-pentyl group, neopentyl group, n-hexyl group, cyclohexyl group, n-heptyl group and the like. However, the lower alkyl groups are not limited to these examples. The "halogen atom" may be any of fluorine atom, chlorine atom, bromine atom and iodine atom.

As the "aryl group", a monocyclic or a condensed polycyclic aromatic group can be used. For example, a monocyclic to tetracyclic aromatic group, preferably a monocyclic to tricyclic aromatic group, and more preferably a monocyclic or bicyclic aromatic group may be used. The carbon number of the aryl group may be 6 to 20, preferably 6 to 16, more preferably 6 to 12, and further preferably 6 to 10. Examples of the aryl group include phenyl group, naphthyl group, anthryl group, phenanthryl group, biphenyl group and the like, but preferably used are phenyl group, 1-naphthyl group, 2-naphthyl group and the like. The aryl group may form a bond at any position on a ring.

As the "heterocyclic group", a monocyclic to tetracyclic heterocyclic group, preferably a monocyclic to tricyclic heterocyclic group, more preferably a monocyclic or bicyclic heterocyclic group may be used, which contains one or more hetero atoms such as nitrogen atom, oxygen atom, and sulfur atom, unless otherwise specifically mentioned. The term "hetero atom" used in the specification means an atom other than carbon atom such as nitrogen atom, oxygen atom and sulfur atom, unless otherwise specifically mentioned. When two or more hetero atoms are contained, they may be the same or different. The hetero ring may be a saturated or partially saturated ring or an aromatic ring. The "aromatic heterocyclic group" means a heterocyclic group whose hetero ring moiety is aromatic, and the "non-aromatic heterocyclic group" means a heterocyclic group whose hetero ring moiety is saturated or partially saturated. The heterocyclic group may form a bond at any position on a ring.

Examples of the heterocyclic group include, for example, isocromanyl group, cromanyl group, pyrrolidinyl group, pyrrolinyl group, imidazolidinyl group, imidazolinyl group, pyrazolidinyl group, pyrazolinyl group, piperidyl group, piperidino group, morpholinyl group, morpholino group, thiomorpholinyl group, thiomorpholino group, piperazinyl group, indolinyl group, isoindolinyl group, quinuclidinyl group, thienyl group, thianthrenyl group, furyl group, pyranyl group, isobenzofuranyl group, chromenyl group, xanthenyl group, phenoxatinyl group, 2H-pyrrolyl group, pyrrolyl group, imidazolyl group, pyrazolyl group, isothiazolyl group, isoxazolyl group, pyridyl group, pyrazinyl group, pyrimidinyl group, pyridazinyl group, indolidinyl group, isoindolyl group, 3H-indolyl group, indolyl group, 1H-indazolyl group, purinyl group, quinolidinyl group, isoquinolyl group, quinolyl group, phthalazinyl group, naphthylidinyl group, quinoxalinyl group, quinazolinyl group, cinnolinyl group, pteridinyl group, 4aH-carbazolyl group, carbazolyl group, β-carbolinyl group, phenanthridinyl group, acridinyl group, perimidinyl group, phenanthrolinyl group, phenadinyl group, phenarsazinyl group, phenothiazinyl group, furazanyl group, phenoxazinyl group, hexamethyleneimino group, heptamethyleneimino group, oxazolyl group, thiazolyl group, triazolyl group, tetrazolyl group and the like. However, heterocyclic groups are not limited to these examples.

In the specification, when a functional group is defined with the phrase "may have a substituent", the phrase means that the functional group may have one or more of any substituents unless otherwise specifically referred to the substituent(s). When the functional group has two or more substituents, they may be the same or different. A position of a substituent is not limited, and a substituent may be present at any substitutable position.

Types of the substituent are not particularly limit, and examples include, for example, a $C_1$–$C_{20}$ alkyl group, a $C_2$–$C_{20}$ alkenyl group, a $C_2$–$C_{20}$ alkynyl group, a $C_6$–$C_{20}$ aryl group, a heterocyclic group, a halogen atom (the halogen atom referred to in the present specification may be any of fluorine atom, chlorine atom, bromine atom and iodine atom), a hydroxyl group, an oxo group, an amino group, an ammonium group, an imino group, a mercapto group, a thioxo group, a cyano group, a nitro group, a carboxyl group, a phosphate group, a sulfo group, a hydrazino group, a $C_1$–$C_{15}$ ureido group, a $C_1$–$C_{15}$ imido group, an isothiocyanato group, an isocyanato group, a $C_1$–$C_{20}$ alkoxy group, a $C_1$–$C_{20}$ alkylthio group, a $C_6$–$C_{20}$ aryloxy group, a heterocyclyloxy group, a $C_6$–$C_{20}$ arylthio group, a heterocyclylthio group, a $C_7$–$C_{20}$ aralkyl group, a heterocyclylalkyl group, a $C_7$–$C_{20}$ aralkyloxy group, a heterocyclylalkyloxy group, a $C_1$–$C_{20}$ alkoxycarbonyl group, a $C_6$–$C_{20}$ aryloxycarbonyl group, a heterocyclyloxycarbonyl group, a $C_2$–$C_{10}$ alkylcarbonyl group, a $C_6$–$C_{20}$ arylcarbonyl group, a heterocyclylcarbonyl group, a $C_2$–$C_{10}$ alkylcarbonyloxy group, a $C_6$–$C_{20}$ arylcarbonyloxy group, a heterocyclylcarbonyloxy group, a $C_2$–$C_8$ alkylcarbonylamino group, a $C_1$–$C_8$ sulfonyl group, a $C_1$–$C_{20}$ sulfinyl group, a $C_1$–$C_8$ sulfonylamino group, a $C_1$–$C_{10}$ carbamoyl group, a $C_2$–$C_{10}$ sulfamoyl group, a $C_1$–$C_{20}$ monoalkylamino group, a $C_2$–$C_{40}$ dialkylamino group, a $C_1$–$C_{20}$ alkylsulfonylamino group, a $C_2$–$C_{20}$ alkylcarbonylamino group, a $C_6$–$C_{20}$ arylcarbonylamino group, a $C_1$–$C_{20}$ alkylsulfonyl group, a $C_6$–$C_{20}$ arylsulfonyl group, a $C_1$–$C_{20}$ alkylsulfinyl group, a $C_6$–$C_{20}$ arylsulfinyl group, a $C_1$–$C_{20}$ alkylsulfonylamino group, a $C_6$–$C_{20}$ arylsulfonylamino group, a $C_2$–$C_{20}$ alkylaminocarbonyl group, a $C_6$–$C_{20}$ arylaminocarbonyl group, a $C_1$–$C_{20}$ alkylaminosulfonyl group, a $C_6$–$C_{20}$ arylaminosulfonyl group and the like.

Furthermore, the substituents exemplified above may further have one or more other substituents. Examples of such substituents include, for example, a hydroxy($C_1$–$C_{20}$ alkyl) group, a halogenated $C_1$–$C_{20}$ alkyl group, a halogenated $C_1$–$C_{20}$ alkylcarbonyl group, a halogenated $C_6$–$C_{20}$ aryl group, a hydroxy($C_6$–$C_{20}$ aryl) group, a mono- or di($C_1$–$C_{20}$ alkyl)carbamoyl group, a $C_1$–$C_{20}$ hydroxyalkyloxy group, a $C_2$–$C_{20}$ alkoxyalkyloxy group, a $C_2$–$C_{20}$ alkylsulfonylaminoalkoxy group, a $C_3$–$C_{20}$ alkylcarbonylaminoalkoxy group, a $C_2$–$C_{20}$ alkylsulfonylaminoalkylthio group, a $C_3$–$C_{20}$ alkylcarbonylaminoalkylthio group and the like. However the aforementioned substituents are explained solely as examples and not limited thereto.

As the "acyl group", an arylcarbonyl group such as benzoyl group or an alkylcarbonyl group such as acetyl group may be used, and these groups may be substituted. Examples of the arylcarbonyl group having a substituent include, for example, p-methoxybenzoyl group, p-chlorobenzoyl group and the like, and examples of the alkylcarbonyl group having a substituent include, for example, chloroacetyl group, trifluoroacetyl group, benzylcarbonyl group and the like. Examples of the alkoxy group include, for example, methoxy group, ethoxy group, n-propoxy group, isopropoxy group, n-butoxy group, sec-butoxy group, tert-butoxy group, n-pentoxy group, neopentoxy group, n-hexoxy group and the like.

The number of double bond existing in the "alkenyl group" is not particularly limited, and may preferably be 1 to 3, more preferably 1 to 2, and further preferably 1. When two or more double bonds are contained, they may be conjugated or not conjugated. The number of triple bond existing in the "alkynyl group" is not particularly limited, and may preferably be 1 to 3, more preferably 1 to 2, and further preferably 1. The alkynyl group may include one or more double bonds. Two of alkyl groups existing in the "dialkylamino group" or "dialkylphosphoryl group" may be the same or different. The number of nitrogen atoms contained as ring-constituting atoms in the "azacycloalkyl group" is not particularly limited, and may preferably be 1 to 3, more preferably 1 to 2, and further preferably 1.

In the general formula (I), A represents a 5- to 7-membered hydrocarbonic ring group. This hydrocarbonic ring group may include one or more double bonds. As A, for example, the aforementioned hydrocarbonic ring group represented by (Ia), (Ib) or (Ic) can be used as well as a benzene ring. As A, a 6-membered hydrocarbonic ring group can be preferably used, and a benzene ring or a hydrocarbonic group represented by (Ib) can be most preferably used. The ring of A may have one or more substituents selected from the group consisting of a hydroxyl group, a lower alkyl group, a lower acyl group, a lower alkoxy group and a halogen atom, and the lower alkyl group, lower acyl group and lower alkoxy group may have one or more substituents. As the substituent existing on the ring of A, a lower alkyl group and a lower alkoxy group are preferred.

In the general formula (I), L represents a linking group selected from the group consisting of —$NR^3$—CO—, —CO—$NR^3$—, —$NR^3$—CS—, —CS—$NR^3$—, —$NR^8$—$SO_2$— and —$SO_2$—$NR^3$—. While $R^3$ represents a hydrogen atom, a lower alkyl group or a lower acyl group, preferably used are a hydrogen atom, methyl group, ethyl group and the like. The lower alkyl group and lower acyl group may have one or more substituents, and examples of such substituents include a halogen atom and the like. L is preferably —$NR^3$—CO— or —CO—$NR^3$—, further preferably —CO—$NR^3$—, and most preferably —CO—NH—.

M represents an alkylene linking group having 2 to 10 carbon atoms, and the alkylene linking group may have one or more substituents. The carbon chain of the alkylene linking group may have one or more branched chains. Further, among the carbon atoms constituting the carbon chain of the alkylene linking group except for at least one carbon atom may be replaced with nitrogen atom, oxygen atom, sulfur atom or a 3- to 8-membered cycloalkylene group. Furthermore, the nitrogen atom may be substituted with a lower alkyl group or a lower acyl group, and the cycloalkylene group may have one or more substituents. However, when L represents —$NR^3$—CO—, M may be a single bond as weU as the aforementioned alkylene linking group. When M represents a single bond, $R^3$ is preferably a hydrogen atom.

Examples of the alkylene linking group represented by M include, for example, an alkylene group, an alkyleneoxyalkylene group, an alkylenethioalkylene group, a cycloalkylenealkylene group, an alkylenecycloalkylene group, an alkylenecycloalkylenealkylene group or a group represented as —$Z^1$—$Z^2$—$Z^3$— [$Z^1$ and $Z^3$ each independently represents an alkylene group, an alkyleneoxyalkylene group, an alkylenethioalkylene group, a cycloalkylenealkylene group or an alkylenecycloalkylene group, which has 2 to 7 carbon atoms, and $Z^2$ represents an oxygen atom, a sulfur atom or a group represented as $NR^6$ ($R^6$ represent a hydrogen atom, a lower alkyl group or a lower acyl group, and the lower alkyl group and lower acyl group may have one or more substituents)]. Preferred examples of M include, for example, —$(CH_2)_4$—, —$(CH_2)_5$—, —$(CH_2)_6$—, an alkylene group containing one oxygen atom, sulfur atom or nitrogen atom (for example, —$(CH_2)_2$—O—$(CH_2)_2$—, —$(CH_2)_2$—S—$(CH_2)_2$—, —$(CH_2)_2$—$NR^6$—$(CH_2)_2$— etc.) and the like. Examples of substituents existing in M include, for example, a hydroxyl group, a lower alkyl group, a lower acyl group, a lower alkoxy group, a mono(lower alkyl)amino group, a di(lower alkyl)amino group, a lower acylamino group and the like, and the lower alkyl group, lower alkoxy group and lower acylamino group may have a substituent.

X represents a linking group selected from the group consisting of —S—, —O—, —$NR^4$—, —$NR^5$—CO—, —$NR^5$—CS— and —$NR^5$—$SO_2$— or a single bond. $R^4$ represents a hydrogen atom, an alkyl group or a lower acyl group, and the alkyl group and lower acyl group may have one or more substituents. The alkyl group may contain a ring structure. $R^5$ represents a hydrogen atom, a lower alkyl group or a lower acyl group, and the lower alkyl group and lower acyl group may have one or more substituents. $R^4$ may bind to M to form a ring. Preferred examples of $R^4$ and $R^5$ include a hydrogen atom, methyl group, ethyl group and the like. The alkyl group and lower acyl group represented by $R^4$, and the lower alkyl group and lower acyl group represented by $R^5$ may have a substituent. Preferably used X include —$NR^5$—CO— and —$NR^5$—$SO_2$—, and most preferred X is —$NR^5$—$SO_2$—. When M represents a single bond, X represents a group represented as —$NR^4$—, and in this case, $R^4$ represents a hydrogen atom or an alkyl group, and the alkyl group may contain a ring structure and have one or more substituents. Further, when A represents a benzene ring, X represents a linking group selected from the group consisting of —$NR^5$—CO—, —$NR^5$—CS— and —$NR^5$—$SO_2$— mentioned above (in the formula, $R^5$ has the same meaning as defined above).

Examples of the substituent of the alkyl group or lower acyl group represented by $R^4$ include, for example, a hydroxyl group, an alkoxy group, an alkylthio group, a carbamoyl group, a cyano group, a halogen atom and the like. Specific examples of $R^4$ include a hydrogen atom, hydroxymethyl group, hydroxyethyl group, methoxymethyl group, methoxyethyl group, methylthiomethyl group, methylthioethyl group, cyanomethyl group, cyanoethyl group, hydroxymethyl group, hydroxyethyl group, carbamoylmethyl group and the like. Further, $R^4$ may bind to M to form a ring. For example, $R^4$ may bind to $Z^1$ or $Z^2$ mentioned above to form a ring, preferably a 5- to 7-membered ring. Specifically, they may form a piperazine ring, piperidine ring, pyrrolidine ring and the like. When a ring is formed, L is preferably a linking group selected from —$NR^3$—CO—, —$NR^3$—CS— and —$NR^3$—$SO_2$—, and L is most preferably —$NR^3$—CO—. Examples of the substituent of the lower alkyl group or lower acyl group represented by $R^5$ include, for example, a halogen atom and the like. Hydrogen atom or methyl group may be preferred as $R^5$.

Y represents a substituent selected from the group consisting of an alkyl group having 1 to 20 carbon atoms (the alkyl group may contain a ring structure), an aryl group having 6 to 12 carbon atoms, an amino group, a monoalkylamino group having 1 to 8 carbon atoms, a dialkylamino group having 2to 16 carbon atoms, an azacycloalkyl group having 4 to 8 carbon atoms, a phosphoryl group, a monoalkylphosphoryl group having 1 to 8 carbon atoms, a dialkylphosphoryl group having 2 to 16 carbon atoms, an aromatic heterocyclic group and a 5- to 7-membered nonaromatic heterocyclic group. Preferably used as the alkyl group having 1 to 20 carbon atoms represented by Y are a linear or branched alkyl group having 1 to 12 carbon atoms, a cycloalkyl group having 3 to 12 carbon atoms and the like. The scope of the cycloalkyl group encompasses bicyclic or tricyclic cycloalkyl groups such as adamantyl group.

The aforementioned substituents represented by Y may further have one or more substituents. Examples of such substituents include, for example, a hydroxyl group, a halogen atom, dimethylamino group and the like. The aforementioned substituents represented by Y may bind to $R^5$ to form a ring. An example where Y and $R^5$ bind to each other to form a ring includes a compound wherein a phthalimide ring is formed. When X represents a single bond, Y represents an aromatic heterocyclic group or a 5- to 7-membered nonaromatic heterocyclic group. Further, when M represents a single bond, $R^4$ and Y may bind to each other to form a ring together with the nitrogen atom to which they bind (the ring may contain one or more hetero atoms as ring-constituting atoms in addition to the nitrogen atom to which $R^4$ and Y bind, and may have one or more substituents on the ring).

When X represents a linking group selected from —NR$^5$—CO—, —NR$^5$—CS— and —NR$^5$—SO$_2$—, preferably used Y includes a linear or branched alkyl group having 1 to 6 carbon atoms, an aryl group, a heterocyclic group, a monoalkylamino group, a dialkylamino group, an azacycloalkyl group having 5 to 7 carbon atoms and the like. Specifically, examples include methyl group, ethyl group, propyl group, isopropyl group, butyl group, phenyl group, naphthyl group, quinolyl group, pyridyl group, benzimidazolyl group, benzotriazolyl group, monomethylamino group, dimethylamino group, pyrrolidino group, piperazino group, morpholino group and the like.

When X represents a linking group represented by —S—, —O— or —NR$^4$—, preferred examples of Y include an aryl group, a dialkylphosphoryl group, an aromatic heterocyclic group and a non-aromatic heterocyclic group. Specifically, preferred examples include tetrazolyl group, triazolyl group, imidazolyl group, oxazolyl group, thiazolyl group, diethylphosphoryl group, hydantoin ring, thiazolidinedione ring, oxazolidone ring, pyrrolodione ring and the like.

When X represents a single bond, Y represents an aromatic heterocyclic group or a 5- to 7-membered non-aromatic heterocyclic group. More specifically, preferred examples thereof include tetrazolyl group, triazolyl group, imidazolyl group, oxazolyl group, thiazolyl group, hydantoin ring, thiazolidinedione ring, oxazolidone ring, pyrrolodione ring and the like.

R$^1$ represents a substituent selected from the group consisting of a lower alkyl group, a lower alkenyl group, a lower alkynyl group and a lower acyl group, and these groups may contain a ring structure. A lower alkyl group or a lower acyl group may preferably be used as R$^1$. The aforementioned groups represented by R$^1$ may have one or more substituents. Examples of the substituent of the aforementioned groups represented by R$^1$ include, for example, a hydroxyl group, an alkoxy group, an alkylthio group, a carbamoyl group, a cyano group, a halogen atom and the like.

Preferred example of R$^1$ include, for example, methyl group, ethyl group, n-propyl group, isopropyl group, n-butyl group, sec-butyl group, tert-butyl group, cyclopropyl group, cyclopropylmethyl group, methoxymethyl group, methoxyethyl group, methylthiomethyl group, methylthioethyl group, cyanomethyl group, cyanoethyl group, propargylmethyl group, hydroxymethyl group, hydroxyethyl group, acetyl group, carbamoylmethyl group and the like. More preferably used examples include methyl group, ethyl group, n-propyl group, isopropyl group, n-butyl group, cyclopropyl group, cyclopropylmethyl group, methoxyethyl group, cyanomethyl group, cyanoethyl group, hydroxymethyl group, hydroxyethyl group, acetyl group, carbamoylmethyl group and the like.

R$^{21}$, R$^{22}$ and R$^{23}$ each independently represent a substituent selected from the group consisting of a hydrogen atom, a hydroxyl group, a lower alkyl group, a lower acyl group, a lower alkoxy group, a halogen atom, an amino group, a mono(lower alkyl)amino group, a di(lower alkyl)amino group, a lower acylamino group and an amido group. It is preferred that all of R$^{21}$, R$^{22}$ and R$^{23}$ represent a hydrogen atom. Alternatively, when any one of, or two or more of R$^{21}$, R$^{22}$ and R$^{23}$ are substituents other than hydrogen atom, preferably used substituents include a hydroxyl group, a lower alkyl group, a lower acyl group, a lower alkoxy group, a halogen atom and a di(lower alkyl)amino group, and more preferably used examples include a hydroxyl group, methyl group, methoxy group, a halogen atom, a carbamoyl group, an amino group, dimethylamino group and the like. The aforementioned groups represented by R$^{21}$, R$^{22}$ and R$^{23}$ may have one or more substituents. For example, they may have a halogen atom and the like.

In the general formula (IV), as R$^{41}$, R$^{51}$, R$^{52}$, R$^{53}$, R$^{63}$ and L', the groups explained as for R$^1$, R$^{21}$, R$^{22}$, R$^{23}$, R$^3$ and L mentioned above can be used. As A' in the general formula (IV), the 5- to 7-membered hydrocarbonic ring groups explained as for A can be used. A' may have one or more substituents selected from the group consisting of a hydroxyl group, a lower alkyl group, a lower acyl group, a lower alkoxy group, a halogen atom, an amino group, a mono(lower alkyl)amino group, a di(lower alkyl)amino group, a lower acylamino group and an amido group on the ring, and the lower alkyl group, lower acyl group and lower alkoxy group may have one or more substituents. The substituent existing on the ring of A' is preferably a hydroxyl group, an amino group, a mono(lower alkyl)amino group, a di(lower alkyl)amino group or a lower acylamino group.

Q represent a substituent selected from the group consisting of an alkyl group, an alkenyl group, an alkynyl group, an alkylalkenyl group, a cycloalkyl group, an alkylcycloalkylalkyl group, an aryl group, a heterocyclic group, an alkylcycloalkyl group, a cycloalkylalkyl group, and an alkylazacycloalkyl group, and the group represented by the aforementioned —M—X—Y (in the formula, M, X and Y have the same meanings as those defined above) can preferably be used as well as a lower alkyl group. For example, ethyl group, propyl group, isopropyl group, butyl group, sec-butyl group, tert-butyl group, cyclopropyl group, cyclopropylmethyl group and the like may be used as Q. The aforementioned groups represented by Q may have one or more substituents. Examples of such substituents include, for example, a hydroxyl group, a carbamoyl group, a sulfamoyl group, a carbamoylalkoxy group, a carbamoylalkylthio group, a sulfamoylalkoxy group, a sulfamoylalkylthio group, a dialkylphosphoryl group, a monoalkylphosphoryl group, phosphoryl group and the like.

In the general formula (XXI), A" represents a 5- to 7-membered hydrocarbon ring group. This hydrocarbonic ring group may contain one or more double bonds. As A", the 5- to 7-membered hydrocarbon ring groups specifically explained as for A can be used. For example, the hydrocarbon ring groups represented by the aforementioned formula (Ia), (Ib) or (Ic) are particularly preferred. On the ring of A, one or more substituents selected from the group consisting of a lower alkyl group, a lower alkoxy group, and a halogen atom may exist, and the lower alkyl group and lower alkoxy group may have one or more substituents. As the substituent existing on the ring of A, a lower alkyl group is preferred.

Preferred examples of the lower alkyl group or lower acyl group represented by R$^{101}$ include, for example, methyl group, ethyl group, n-propyl group, isopropyl group, cyclopropyl group, n-butyl group, isobutyl group, sec-butyl group, tert-butyl group, cyclobutyl group, cyclopropylmethyl group, methoxymethyl group, methoxyethyl group, methylthiomethyl group, methylthioethyl group, cyanomethyl group, cyanoethyl group, propargylmethyl group, hydroxymethyl group, hydroxyethyl group, acetyl group, carbamoylmethyl group and the like. More preferred examples include ethyl group, n-propyl group, isopropyl group, isobutyl group, cyclopropyl group, cyclopropylmethyl group and the like, and particularly preferred are isopropyl group and isobutyl group.

Among the alkyl group having a total carbon number of 1 to 20 represented by R$^{102}$, an alkyl group having a total carbon number of 1 to 10 is preferred, and a lower alkyl group is more preferred. Particularly preferred is methyl group. A preferred example of the alkyl group having a total carbon number of 1 to 20 represented by $R^{103}$ includes an alkyl group having a total carbon number of 1 to 20 and having one or more substituents which contain one or more hetero atoms selected from a nitrogen atom, an oxygen atom, and a sulfur atom (the alkyl moiety may preferably be a linear or cyclic lower alkyl group having 1 to 4 carbon atoms, and the total carbon number includes the carbon number of substituents).

Preferred examples of the substituents containing one or more hetero atoms selected from a nitrogen atom, an oxygen atom, and a sulfur atom, which exist on the alkyl group having a total carbon number of 1 to 20 represented by $R^{103}$, include hydroxyl group, an amino group, cyano group, a carbamoyl group, a sulfamoyl group, a lower alkoxy group, a lower alkylthio group, a lower alkylsulfonylamino group, a lower alkylcarbonyl amino group, a hydroxyalkyl group, a hydroxyalkyloxy group, an alkoxyalkyloxy group, a monoalkylamino group, a dialkylamino group, a lower alkylsulfonylaminoalkoxy group, a lower alkylcarbonylaminoalkoxy group, a lower alkylsulfonylaminoalkylthio group, a lower alkylcarbonylaminoalkylthio group and the like. Preferred examples also include a heterocyclic group such as tetrazolyl group, triazolyl group, imidazolyl group, pyridyl group, morpholinyl group, morpholino group, thiomorpholino group, piperazino group, piperazinyl group, piperidino group, piperidinyl group and pyrrolidinyl group, a heterocyclylthio group such as triazolylthio group and imidazolylthio group and the like. More preferred examples include a lower alkoxy group or pyridyl group, and particularly preferred are methoxy group, 3-pyridyl group and 4-pyridyl group.

$R^{102}$ and $R^{103}$ may bind to each other to form a ring together with the nitrogen atom to which they bind. This ring may have one or more hetero atoms preferably selected from the group consisting of nitrogen atom, oxygen atom and sulfur atom as ring-constituting atoms in addition to the nitrogen atom to which $R^{102}$ and and $R^{103}$ bind. One or more substituents may exist on the ring, and when two or more substituents exist, they may be the same or different. The ring to be formed is preferably a 5- to 8-membered ring, and a group represented by the aforementioned general formula (XXII) is particularly preferred.

$R^{104}$, $R^{105}$ and $R^{106}$ each independently represent a substituent selected from the group consisting of a hydrogen atom, a hydroxyl group, a lower alkyl group, a lower acyl group, a lower alkoxy group, a halogen atom, an amino group, a mono(lower alkyl)amino group, a di(lower alkyl) amino group, a lower acylamino group and an amido group (this substituent may have one or more substituents), and the groups specifically explained as for the above $R^{21}$, $R^{22}$ and $R^{23}$ can be used, respectively. It is preferred that all of $R^{104}$, $R^{105}$ and $R^{106}$ represent a hydrogen atom, and in this case, it is also preferred that either $R^{105}$ or $R^{106}$ represents a halogen atom, preferably a fluorine atom.

The compounds represented by the general formula (I) or the general formula (IV) may have one or two asymmetric carbons depending on the types of the substituents, and stereoisomers such as optically active isomers based on one or more asymmetric carbons and diastereoisomer based on two or more asymmetric carbons may exist. When the compounds represented by the general formula (I) or the general formula (IV) have an alkenyl group, its configuration may be either in Z or E.

The compound represented by the general formula (I) or the general formula (IV) may exist as a salt. Examples of the salt include acid addition salt such as inorganic acid salts and organic acid salts; base addition salts such as metal salts, ammonium salts and organic ammonium salts; amino acid addition salts and the like. Examples of the acid addition salts include, besides inorganic acid salts such as hydrochlorides, nitrates, hydrobromides, sulfates, hydrogensulfates, monohydrogenphosphates and dihydrogenphosphates, salts of organic acids such as aliphatic monocarboxylates, dicarboxylates, hydroxyalkanoates, hydroxylated dialkanoate, amino acid salts, aromatic carboxylates and aliphatic or aromatic sulfonates.

Examples of the organic acid salts include formates, acetates, propionates, benzoates, maleates, malonates, fumarates, phthalates, succinates, tartrates, citrates, mandelates, oxalates, methanesulfonates, p-toluenesulfonates, benzenesulfonates, lactates, malates, glycolates, aspartates, glutamates and the like. Examples of the metal salts include, for example, alkali metal salts such as lithium salts, sodium salts and potassium salts, alkaline earth metal salts such as magnesium salts and calcium salts, aluminum salts, zinc salts and the like. Examples of the ammonium salts include ammonium salts, tetramethylammonium salts and the like, and examples of the organic ammonium salts include salts obtained by addition of morpholine, piperidine and the like. Examples of the amino acid addition salts include, for example, salts obtained by addition of glycine, phenylalanine, glutamic acid, lysine and the like. Furthermore, the compounds represented by the general formula (I) or the general formula (IV) or salts thereof may exist as a hydrate or a solvate. A type of a solvent that forms the solvate is not particularly limited. Examples thereof include, for example, alcohols such as methanol, ethanol and isopropanol, ethers such as tetrahydrofuran and the like.

Any of the compounds of the general formula (I) in a free form and salts thereof, and hydrates thereof and solvates thereof falls within the scope of the present invention. Further, any of the aforementioned isomers of the compounds represented by the general formula (I) according to the present invention in a pure form, any mixtures of such isomers, racemates thereof and the like also falls within the scope of the present invention. As active ingredients of the medicaments of the present invention, the compounds represented by the general formula (I) in a pure form or physiologically acceptable salts thereof, or hydrates thereof or solvates thereof can be used. As active ingredients of the medicaments of the present invention, the aforementioned isomers in a pure form, any mixtures of the aforementioned isomers, racemates thereof and the like can also be used. Furthermore, biological equivalents and chemical equivalents of the compounds represented by the general formula (I) or the general formula (IV) may also be used as active ingredients of the medicaments of the present invention. For example, dimers, prodrugs and the like of the compounds can be used as active ingredients of the medicaments of the present invention.

Specific examples of the compounds represented by the general formula (I) or the general formula (IV) will be shown below. However, the compounds represented by the general formula (I) or the general formula (IV) are not limited to these examples.

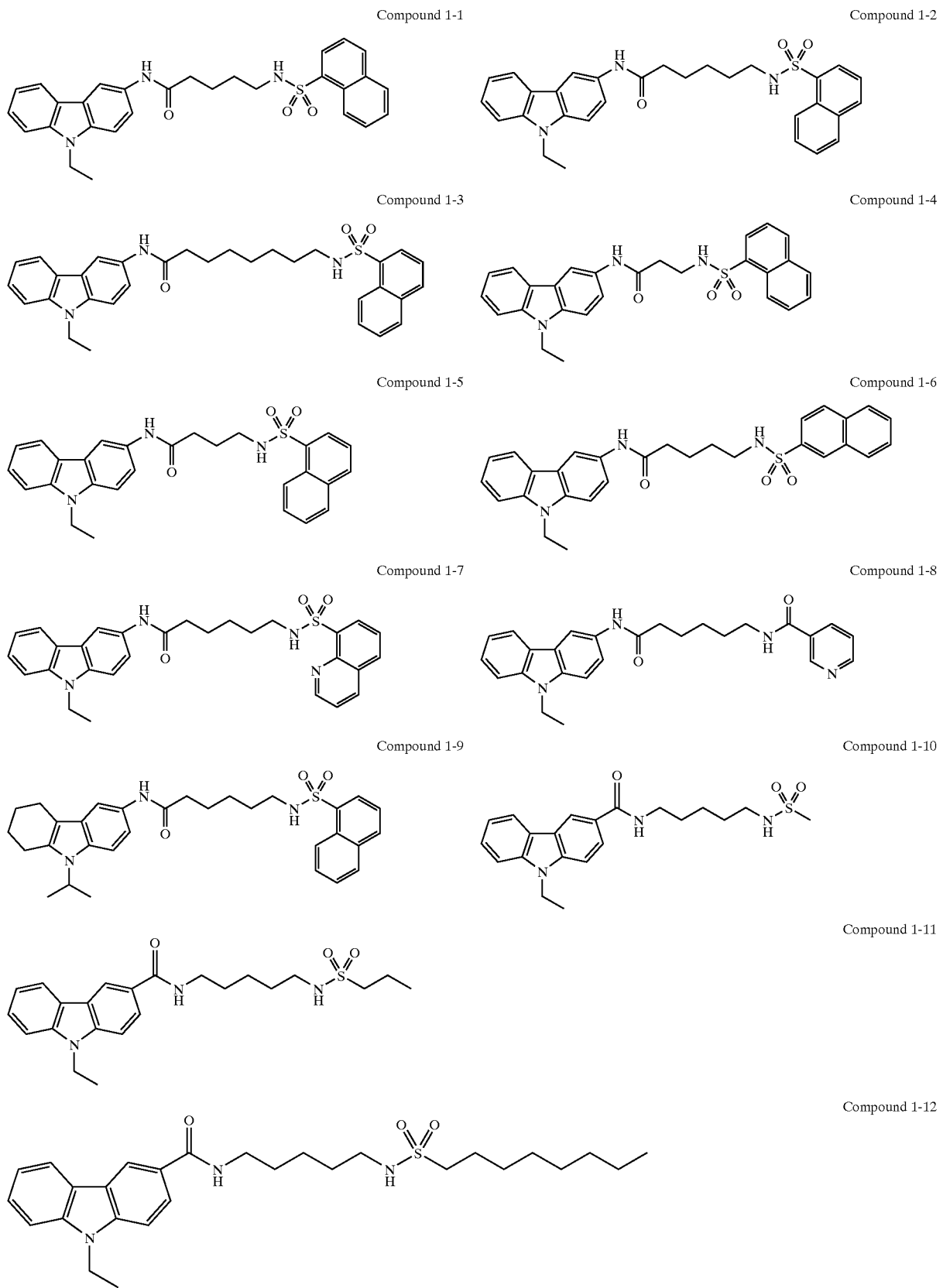

-continued
Compound 1-13
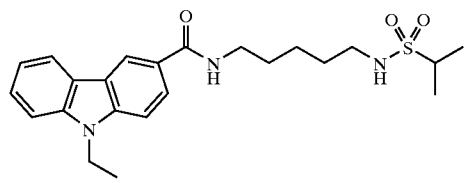
Compound 1-14
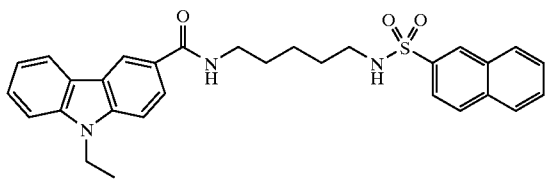
Compound 1-15
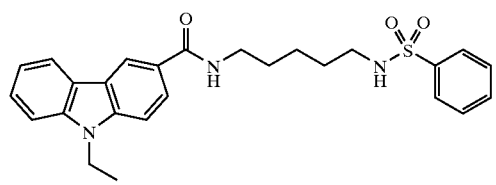
Compound 1-16
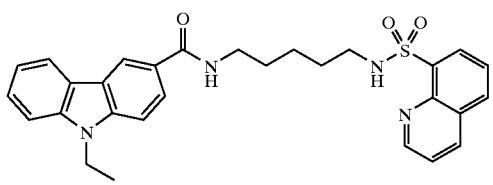
Compound 1-17
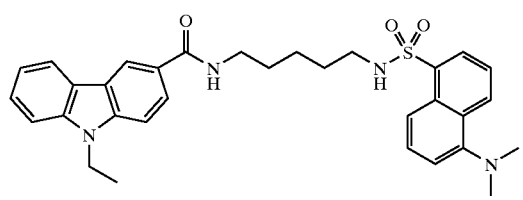
Compound 1-18
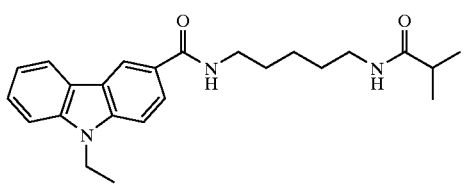
Compound 1-19
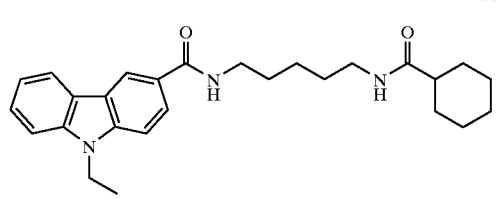
Compound 1-20
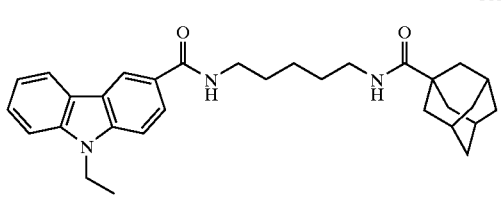
Compound 1-21
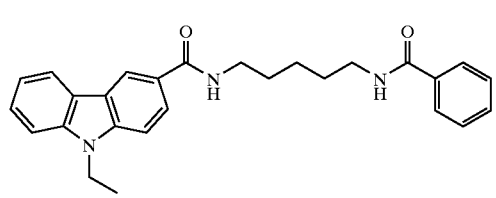
Compound 1-22
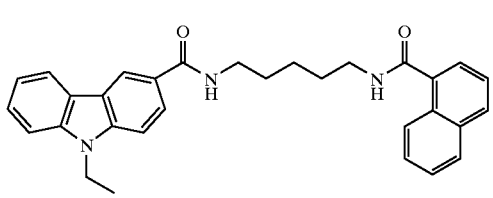
Compound 1-23
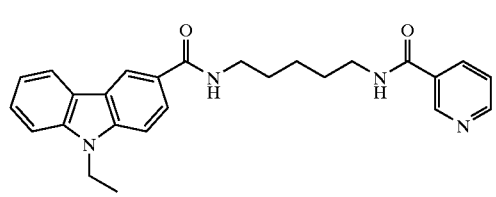
Compound 1-24
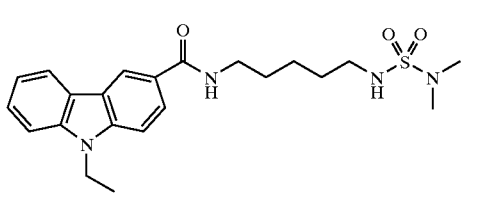
Compound 1-25
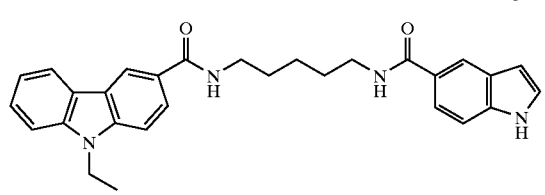
Compound 1-26
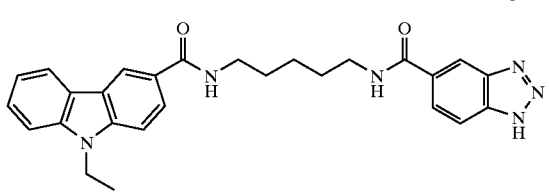

-continued

Compound 1-27

Compound 1-28

Compound 1-29

Compound 1-30

Compound 1-31

Compound 1-32

Compound 1-33

Compound 1-34

Compound 1-35

Compound 1-36

Compound 1-37

Compound 1-38

Compound 1-39

Compound 1-40

-continued
Compound 1-41
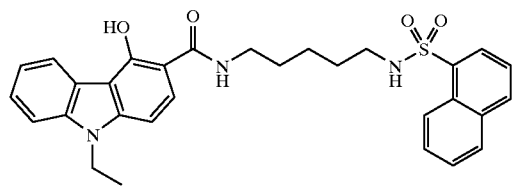
Compound 1-42
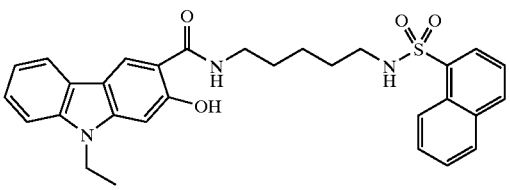
Compound 1-43
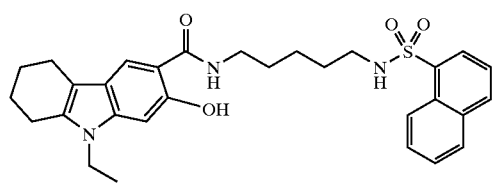
Compound 1-44
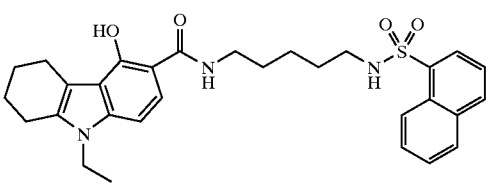
Compound 1-45
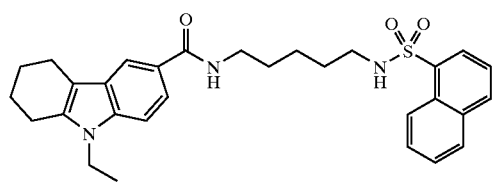
Compound 1-46
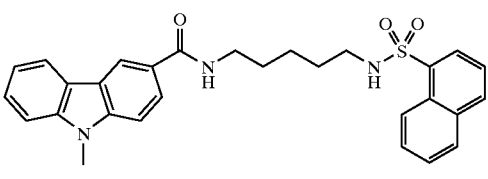
Compound 1-47
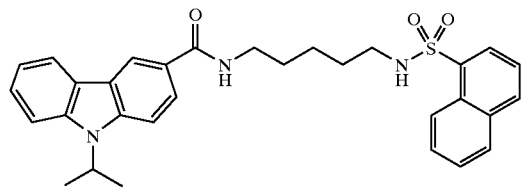
Compound 1-48
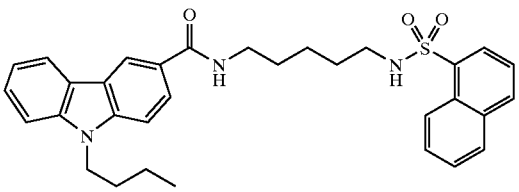
Compound 1-49
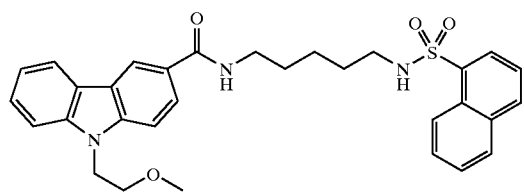
Compound 1-50
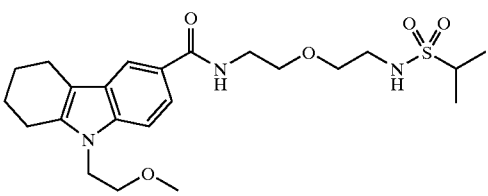
Compound 1-51
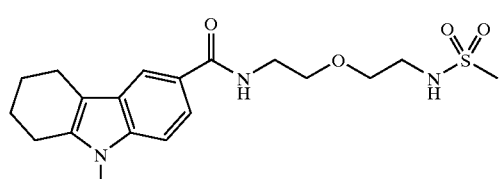
Compound 1-52
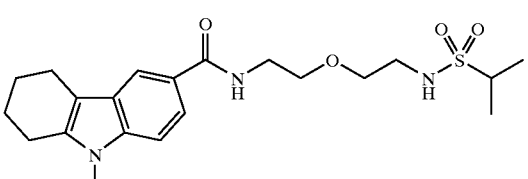
Compound 1-53
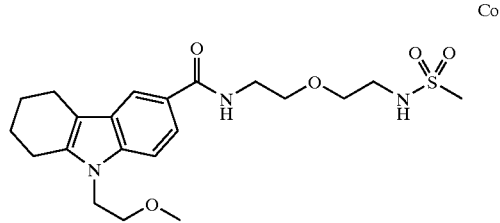
Compound 1-54
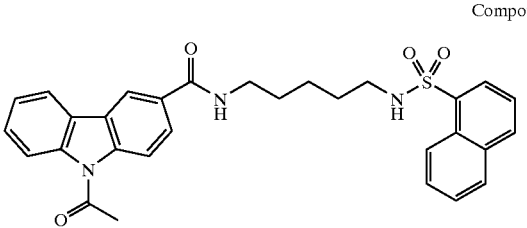

-continued
Compound 1-55
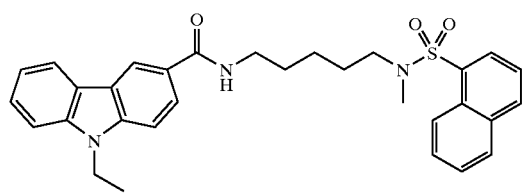
Compound 1-56
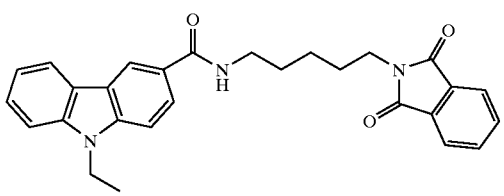
Compound 1-57
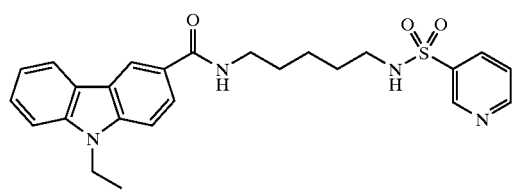
Compound 1-58
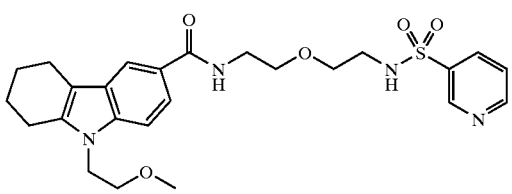
Compound 1-59
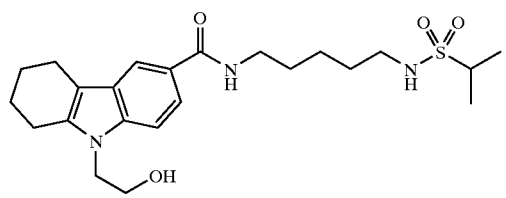
Compound 1-60
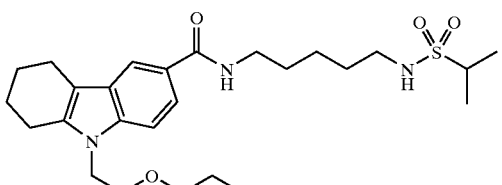
Compound 1-61
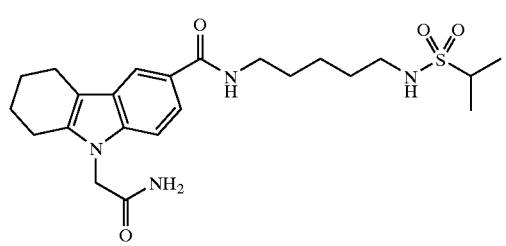
Compound 1-62
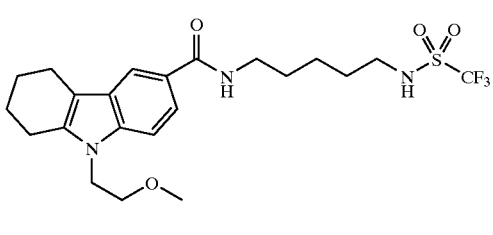
Compound 1-63
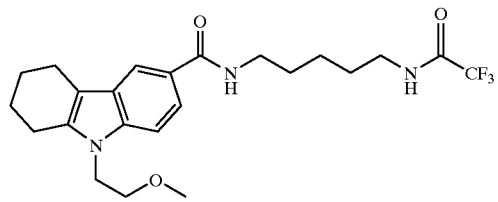
Compound 2-1
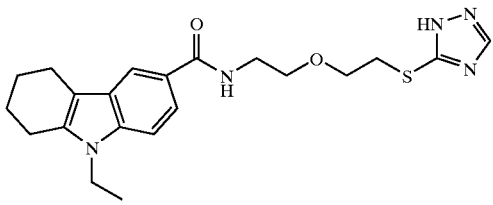
Compound 2-2
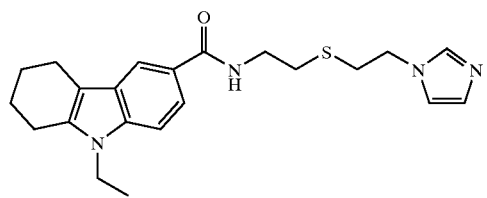
Compound 2-3
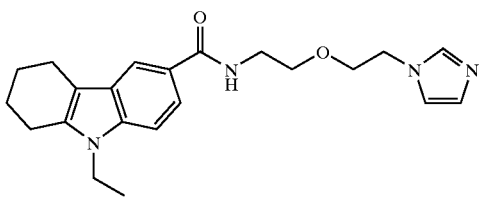
Compound 2-4
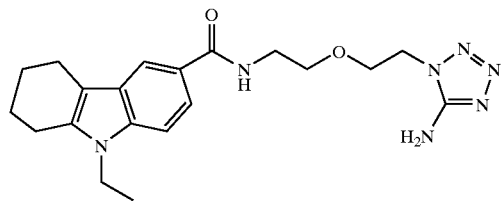
Compound 2-5
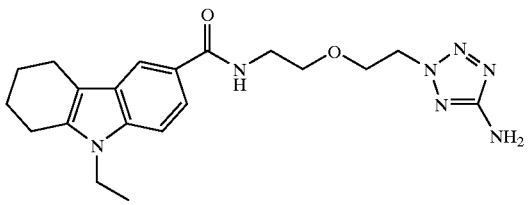

Compound 2-6

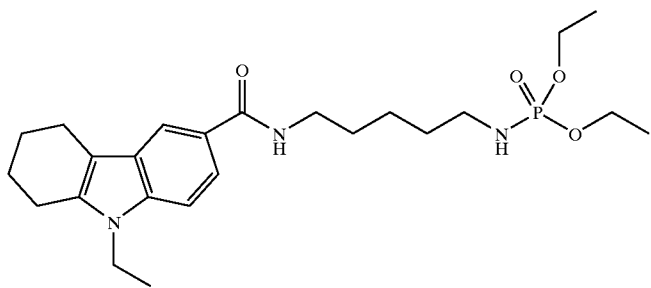

Specific examples of the compounds represented by the general formula (IV) other than those mentioned above will be shown below. However, the compounds represented by the general formula (IV) are not limited to these examples.

Compound 3-1

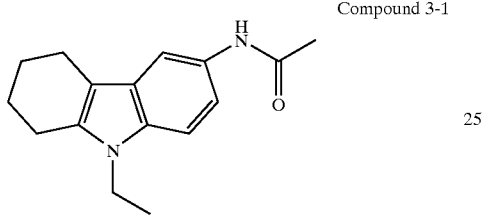

Compound 3-2

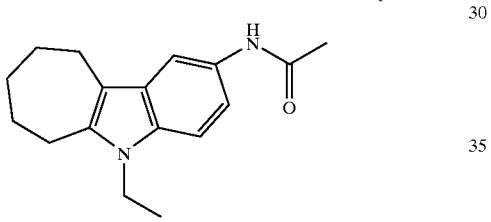

Compound 3-3

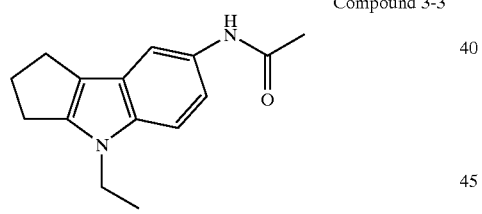

Compound 3-4

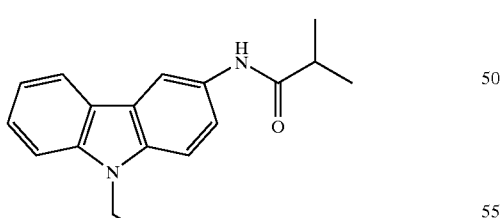

Compound 3-5

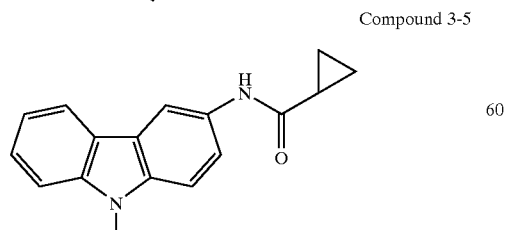

Compound 3-6

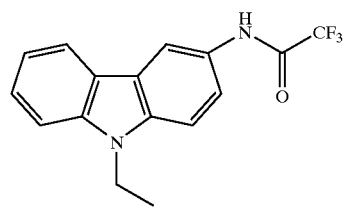

Compound 3-7

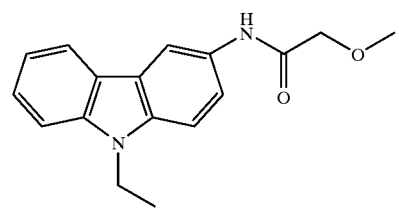

Compound 3-8

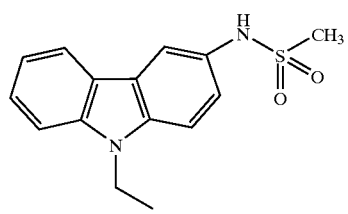

Compound 3-9

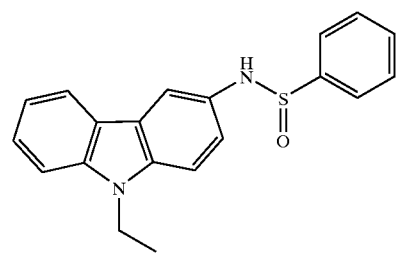

Specific examples of the compounds represented by the general formula (XXI) will be shown below. However, the compounds represented by the general formula (XXI) are not limited to these examples.

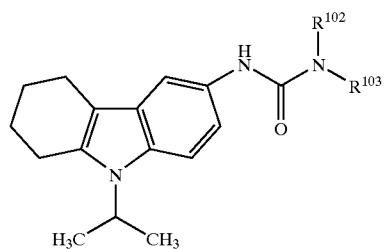

| Compound No. | $R^{102}$ | $R^{103}$ |
|---|---|---|
| Compound 4-1 | H | —CH₃ |
| Compound 4-2 | H | ～～OH |
| Compound 4-3 | H | ～～～OH |
| Compound 4-4 | H | ～～～CN |
| Compound 4-5 | H | ～～O～OH |
| Compound 4-6 | H | ～～～NHSO₂CH(CH₃)₂ |
| Compound 4-7 | H | ～-(2-pyridyl) |
| Compound 4-8 | H | ～-(3-pyridyl) |
| Compound 4-9 | H | ～-(4-pyridyl) |
| Compound 4-10 | H | ～～～-(1-imidazolyl) |
| Compound 5-1 | —CH₃ | —CH₃ |
| Compound 5-2 | —CH₃ | —CH₂CH(CH₃)₂ |
| Compound 5-3 | —CH₃ | ～～～CH₃ |
| Compound 5-4 | —CH₃ | ～～OH |
| Compound 5-5 | —CH₃ | ～～～N(CH₃)₂ |
| Compound 5-6 | —CH₃ | ～～～OH |
| Compound 5-7 | —CH₃ | ～～～OCH₃ |

-continued

| | | |
|---|---|---|
| Compound 5-8 | —CH₃ | pentyl-NH₂ |
| Compound 5-9 | —CH₃ | propyl-CN |
| Compound 5-10 | —CH₃ | propyl-O-CH₂CH₂-OH |
| Compound 5-11 | —CH₃ | methylcyclohexyl |
| Compound 5-12 | —CH₃ | trans-4-methylcyclohexanol |
| Compound 5-13 | —CH₃ | (tetrahydrofuran-2-yl)ethyl |
| Compound 5-14 | —CH₃ | 3-(piperidin-1-yl)propyl |
| Compound 5-15 | —CH₃ | 3-(4-methylpiperazin-1-yl)propyl |
| Compound 5-16 | —CH₃ | 3-(morpholin-4-yl)propyl |
| Compound 5-17 | —CH₃ | 2-(pyridin-4-yl)ethyl |
| Compound 5-18 | —CH₃ | 3-(pyridin-2-yl)propyl |
| Compound 5-19 | —CH₃ | 3-(pyridin-3-yl)propyl |
| Compound 5-20 | —CH₃ | 3-(pyridin-4-yl)propyl |
| Compound 5-21 | —CH₃ | 5-(phthalimid-2-yl)pentyl |
| Compound 5-22 | —CH₃ | 4-(imidazol-1-yl)butyl |

-continued

| Compound 5-23 | —CH₃ | 3-(propylthio)-4H-1,2,4-triazole |
| Compound 5-24 | —CH₃ | 3-(butylthio)-4H-1,2,4-triazole |
| Compound 5-25 | —CH₃ | 2-(propylthio)-1H-imidazole |
| Compound 5-26 | —CH₃ | 2-ethyl-1,3-propanediol group (CH₂CH(OH)CH₂OH with ethyl) |
| Compound 6-1 | —CH₂CH₂CH₃ | —(CH₂)₄OH |
| Compound 6-2 | —CH₂CH₂CH₂OH | —CH₂CH₂CH₂OH |
| Compound 6-3 | —CH₂CH₂CH₂OCH₃ | —CH₂CH₂CH₂OCH₃ |

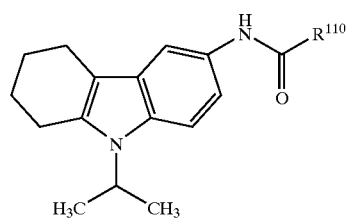

| Compound No. | R¹¹⁰ |
|---|---|
| Compound 7-1 | pyrrolidin-1-yl |
| Compound 7-2 | piperidin-1-yl |
| Compound 7-3 | azepan-1-yl |
| Compound 7-4 | 3-hydroxypyrrolidin-1-yl |
| Compound 7-5 | (2S)-2-(hydroxymethyl)pyrrolidin-1-yl |
| Compound 7-6 | (2R)-2-(hydroxymethyl)pyrrolidin-1-yl |

-continued
| | |
|---|---|
| Compound 7-7 | 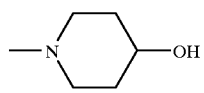 |
| Compound 7-8 | 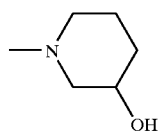 |
| Compound 7-9 | 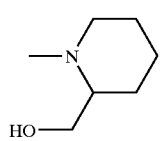 |
| Compound 7-10 | 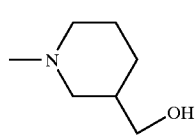 |
| Compound 7-11 | 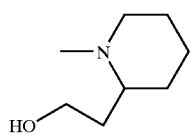 |
| Compound 7-12 | 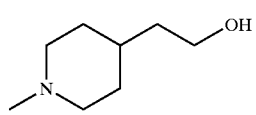 |
| Compound 7-13 | 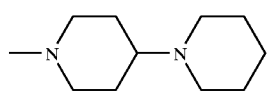 |
| Compound 7-14 | 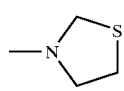 |
| Compound 7-15 | 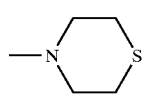 |
| Compound 7-16 | 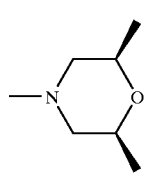 |
| Compound 7-17 | 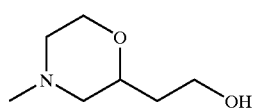 |
| Compound 7-18 | 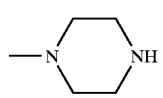 |
| Compound 7-19 | 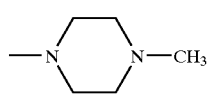 |

-continued
| | |
|---|---|
| Compound 7-20 | 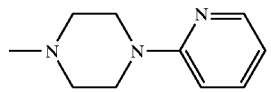 |
| Compound 7-21 | 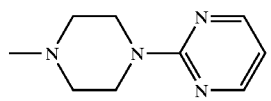 |
| Compound 7-22 | 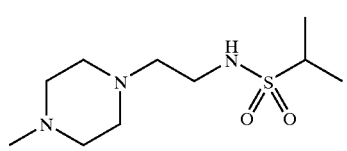 |
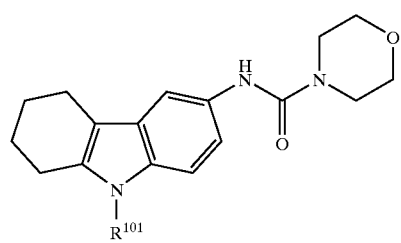
| Compound No. | $R^{101}$ |
|---|---|
| Compound 8-1 | —CH$_3$ |
| Compound 8-2 |  |
| Compound 8-3 | 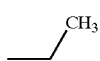 |
| Compound 8-4 | 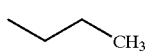 |
| Compound 8-5 | 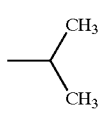 |
| Compound 8-6 | 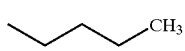 |
| Compound 8-7 | 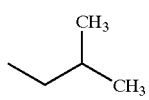 |
| Compound 8-8 | 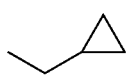 |
| Compound 8-9 | 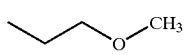 |
| Compound 8-10 | 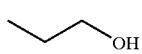 |
| Compound 8-11 | 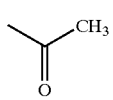 |

-continued
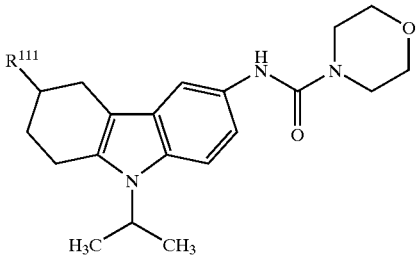
| Compound No. | R¹¹¹ |
|---|---|
| Compound 9-1 | —CH₃ |
| Compound 9-2 | —OCH₃ |
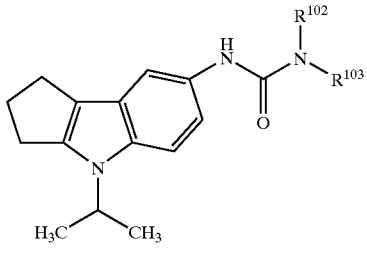
| Compound No. | R¹⁰² | R¹⁰³ |
|---|---|---|
| Compound 10-1 | —CH₃ | 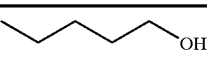 |
| Compound 10-2 | —CH₃ | 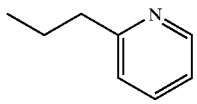 |
| Compound 10-3 | —CH₃ | 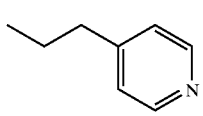 |
| Compound 10-4 | | 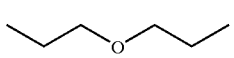 |
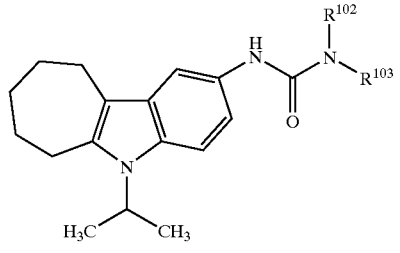
| Compound No. | R¹⁰² | R¹⁰³ |
|---|---|---|
| Compound 11-1 | —CH₃ | 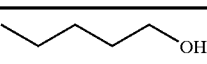 |
| Compound 11-2 | —CH₃ | 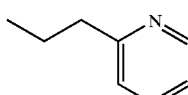 |
| Compound 11-3 | —CH₃ | 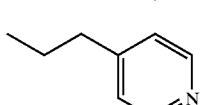 |

-continued

| | |
|---|---|
| Compound 11-4 | 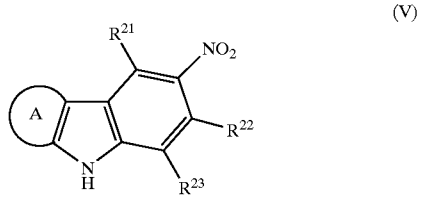 |

Compound 12-1

Compound 12-2

Compound 12-3

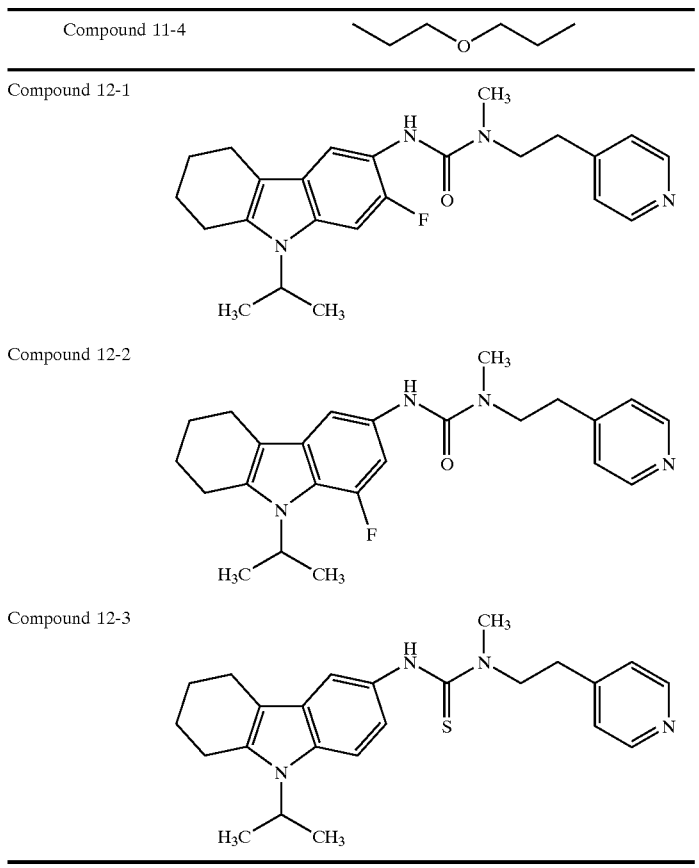

The compounds represented by the general formula (I) or the general formula (IV) can be prepared according to the following methods, for example. However, the methods for preparing the aforementioned compounds are not limited to the following methods.

<Preparation Method 1>

Method for preparing the compounds of the general formula (I) wherein L is —NR³—CO—, —NR³—CS— or —NR³—SO₂— and X is —NR⁵—CO—, —NR⁵—CS— or —NR⁵—SO₂—

A compound represented by the general formula (V):

(V)

$$\text{structure}$$

(in the formula, A, R²¹, R²² and R²³ have the same meanings as those defined above) can be reacted with a compound represented by the general formula: R¹X¹ (in the formula, R¹ has the same meaning as that defined above, and X¹ represents a leaving group) in an organic solvent in the presence of a base to prepare a compound represented by the general formula (VI):

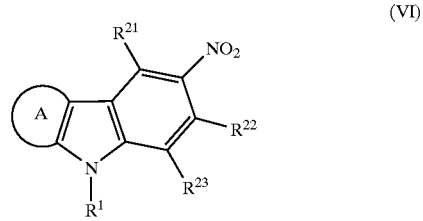

(VI)

(in the formula, A, R¹, R²¹, R²² and R²³ have the same meanings as those defined above).

As the leaving group X¹ of R¹X¹ used in the aforementioned reaction, a halogen atom, tosyl group or mesyl group is preferred. A type of the organic solvent used for the reaction is not particularly limited so long as the solvent is inert in the reaction. For example, generally used organic solvents such as acetonitrile, tetrahydrofuran, dimethylformamide, dimethylacetamide, dimethyl sulfoxide and acetone may be used. Examples of the base to be used include generally used bases such as sodium hydride, sodium hydroxide, potassium carbonate, sodium carbonate, sodium hydrogencarbonate and triethylamine. The reaction temperature is usually –20° C. to 100° C., preferably 0° C. to room temperature. The reaction time is usually 1 minute to 3 days, preferably from 1 hour to 1 day.

Subsequently, the nitro group of the compound represented by the general formula (VI) can be reduced to convert the compound into a compound represented by the general formula (VII):

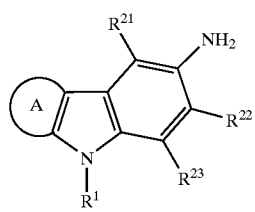

(VII)

(in the formula, A, $R^1$, $R^{21}$, $R^{22}$ and $R^{23}$ have the same meanings as those defined above). Various generally used methods may be applied as the reduction method. A typical example includes reduction using iron. As a preferred reaction solvent, acetic acid can be used. The reaction temperature is usually 0° C. to 100° C., preferably room temperature to 70° C. The reaction time is usually 1 minute to 3 days, preferably from 1 hour to 1 day.

Then, the compound represented by the general formula (VII) and a compound represented by the general formula: $X^2$—M—N($R^5$)($X^3$) (in the formula, $X^2$ represents —COOH, —COCl, —CSCl or —$SO_2$Cl, $X^3$ represents an amino protective group, and M and $R^5$ have the same meanings as those defined above) are condensed, and the amino protective group is deprotected. For the condensation reaction, when $X^2$ is —COOH, usual condensation methods such as the DCC condensation, DCC/HOBt method, WSC method, mixed acid anhydride method, CDI method DPPA method and the like can be used. The DCC condensation, DCC/HOBt method and WSC method are preferred. When $X^2$ is —COCl, —CSCl or —$SO_2$Cl, an applicable method includes a method of condensation performed in a generally used organic solvent such as tetrahydrofuran, dimethylformamide, dimethylacetamide and dichloromethane in the presence of a base such as potassium carbonate and triethylamine. The reaction temperature of the condensation reaction is usually -20° C. to 100° C., preferably 0° C. to room temperature. The reaction time is usually 10 minutes to 3 days, preferably from 1 hour to 1 day.

Various protective groups can be used as the amino protective group of $X^3$ (see, for example, Protective Groups in Organic Synthesis, T. W. Greene, John Wiley & Sons, Inc., 1981 etc.). For example, Boc group and the like are preferred. Depending on the used protective group, an appropriate method can be used for deprotection. For example, when Boc group is used, a method using a hydrochloric acid solution in dioxane and trifluoroacetic acid is preferred. The reaction temperature is usually -20° C. to 50° C., preferably -20° C. to room temperature. The reaction time is usually 10 minutes to 3 days, preferably 30 minutes to 3 hours.

When $R^3$ is not a hydrogen atom, a compound represented by the general formula (VII) is reacted with a compound represented by the general formula: $R^3X^1$ ($R^3$ has the same meaning as that defined above, and $X^1$ represents a leaving group) in an organic solvent in the presence of NaOH, and then the amino protective group is deprotected. In this case, a phthalimide group is preferred as the amino protective group represented by $X^3$, and this protective group can be deprotected by using hydrazine. Finally, a product obtained can be condensed with a compound represented by the general formula: $X^4$—Y (in the formula, $X^4$ represents —COOH, —COCl, —CSCl or —$SO_2$Cl, and Y has the same meaning as that defined above) to produce a compound represented by the general formula (I). As the condensation method, the aforementioned methods can be used. Further, a corresponding anhydride may also be used. If a compound of the general formula: $X^2$—M—X—Y is readily available (in the formula, $X^2$, M, X and Y have the same meanings as defined above), a compound of the general formula (VII) and a compound of the general formula $X^2$—M—X—Y can be condensed to obtain a compound of the general formula (I) (L is —$NR^3$—CO—, —$NR^3$—CS— or —$NR^3$—$SO_2$—, and X is —$NR^5$—CO—, —$NR^5$—CS— or —$NR^5SO_2$—). The order of the reactions of the aforementioned preparation method may be changed according to properties of a target compound.

<Preparation Method 2>

Method for preparing compounds represented by the general formula (IV) wherein L' is —$NR^{63}$—CO—, —$NR^{63}$—CS— or —$NR^{63}$—$SO_2$— and Q is a substituent selected from the group consisting of an alkyl group, an alkenyl group, an alkynyl group, an alkylalkenyl group, a cycloalkyl group, an alkylcycloalkylalkyl group, an aryl group, a heterocyclic group, an alkylcycloalkyl group, a cycloalkylalkyl group and an alkylazacycloalkyl group (the substituent may have one or more substituents)

A compound represented by the general formula (IV) can be produced by condensing a compound represented by the general formula (VII) with a compound represented by the general formula: $X^2$—Q (in the formula, $X^2$ has the same meaning as defined above) in a manner similar to that of Preparation method 1.

<Preparation Method 3>

Method for preparing compounds represented by the general formula (I) wherein L is —CO—$NR^3$— and X is —$NR^5$—CO—, —$NR^5$—CS— or —$NR^5$—$SO_2$—

A compound represented by the general formula (VIII):

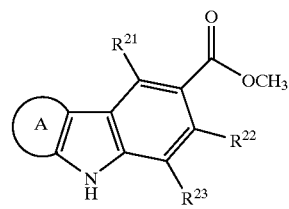

(VIII)

(in the formula, A, $R^{21}$, $R^{22}$ and $R^{23}$ have the same meanings as defined above) can be reacted with a compound represented by the general formula: $R^1X^1$ (in the formula, $R^1$ has the same meaning as that defined above, and $X^1$ represents a leaving group) in an organic solvent in the presence of a base to produce a compound represented by the general formula (IX):

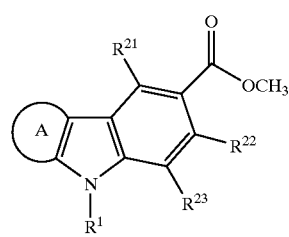

(IX)

(in the formula, A, $R^1$, $R^{21}$, $R^{22}$ and $R^{23}$ have the same meanings as those defined above). As the leaving group $X^1$ of $R^1X^1$ to be used, a halogen, tosyl group or mesyl group is preferred. A type of the organic solvent is not particularly limited so long as the solvent is inert it the reaction, and generally used organic solvents such as acetonitrile, tetrahydrofuran, dimethylformamide, dimethylacetamide, dimethyl sulfoxide and acetone may be used. Examples of the base to be used include generally used bases such as sodium hydride, sodium hydroxide, potassium carbonate, sodium carbonate, sodium hydrogencarbonate and triethylamine.

Subsequently, the product can be converted into a compound represented by general formula (X):

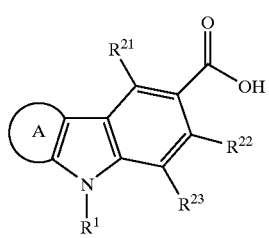

(X)

(in the formula, A, $R^1$, $R^{21}$, $R^{22}$ and $R^{23}$ have the same meanings as those defined above) by usual alkali hydrolysis. For the reaction, a generally used organic solvent such as tetrahydrofuran, methanol and ethanol, and 0.1 N to 2 N aqueous solution of, for example, sodium hydroxide, potassium hydroxide, potassium carbonate, sodium carbonate or the like may be used. The reaction temperature is usually −20° C. to 100° C., preferably 0° C. to room temperature. The reaction time is usually 10 minutes to 8 days, preferably 1 hour to 1 day.

Then, the compound of the general formula (X) is condensed with a compound represented by the general formula: $HR^3N$—M—$NR^5X^3$ (in the formula, $X^3$, M, $R^3$ and $R^5$ have the same meanings as those defined above), and the amino protective group is deprotected. The usual condensation methods exemplified above can be used as the condensation reaction, and the DCC condensation or the DCC/HOBt method is preferred. The reaction temperature of the condensation reaction is usually −20° C. to 100° C., preferably 0° C. to room temperature. The reaction time is usually 10 minutes to 3 days, preferably 1 hour to 1 day. Various protective groups can be used as the amino protective group of $X^3$. For example, Boc group or the like is preferred. Depending on the used protective group, an appropriate method can be used for deprotection. For example, where Boc group is used, the method using hydrochloric acid solution in dioxane and trifluoroacetic acid is preferred. The reaction temperature is usually −20° C. to 50° C., preferably −20° C. to room temperature. The reaction time is usually 10 minutes to 3 days, preferably 30 minutes to 3 hours.

Finally, a product obtained can be condensed with a compound represented by the general formula: $X^4$—Y (in the formula, $X^4$ represents —COOH, —COCl, —CSCl or —$SO_2Cl$, and Y has the same meaning as those defined above) to produce a compound of the general formula (I). As the condensation method, the aforementioned methods can be used, and a corresponding anhydride may also be used.

In connection with the aforementioned preparation method, the aforementioned condensation can also be conducted by using a compound of the general formula: $R^3HN$—M—X—Y (in the formula, $R^3$, M, X and Y have the same meanings as those defined above) to obtain a compound of the general formula (I) (where L is —CO—$NR^3$— and X is —$NR^3$—CO—, —$NR^3$—CS— or —$NR^3$—$SO_2$—). For the condensation reaction, usual DCC condensation, DCC/HOBt method or WSC method can be used. The reaction temperature is usually −20° C. to 100° C., preferably 0° C. to room temperature. The reaction time is usually 10 minutes to 3 days, preferably 1 hour to 1 day. Further, the order of the reactions of the aforementioned preparation method may be changed depending on properties of a target compound.

In the aforementioned production method, when A is a benzene ring, the carboxylic acid represented by the general formula (X) can also be produced by oxidizing an aldehyde represented by the general formula (XI):

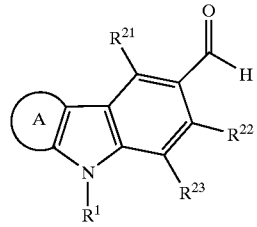

(XI)

(in the formula, A, $R^1$, $R^{21}$, $R^{22}$ and $R^{23}$ have the same meanings as those defined above). Various generally used oxidation methods can be used as the oxidation method, and the method using potassium permanganate in acetone is preferred. <Preparation Method 4>

Method for preparing compounds represented by the general formula (IV) wherein L' is —CO—$NR^{63}$— and Q is a substituent selected from the group consisting of an alkyl group, an alkenyl group, an alkynyl group, an alkylalkenyl group, a cycloalkyl group, an alkylcycloalkylalkyl group, an aryl group, a heterocyclic group, an alkylcycloalkyl group, a cycloalkylalkyl group and an alkylazacycloalkyl group (the substituent may have one or more substituents)

A compound represented by the general formula (IV) can be produced by reacting a compound represented by the general formula (XI) with a compound represented by the general formula: $R^3HN$—Q (in the formula, $R^3$ and Q have the same meanings as those defined above) in a manner similar to that of Preparation method 3.

<Preparation Method 5>

Method for preparing compounds represented by the general formula (I) wherein L is —NH—CO— or —CO—$NR^3$— and X is —S—, —O—, —$NR^4$— or a single bond A compound represented by the general formula (VII) obtained by Preparation method 1 described above and a compound represented as HOOC—M—OH (in the formula, M has the same meaning as that defined above) are condensed, or a compound represented by the general formula (X) obtained by Preparation method 3 and a compound represented as $HR^3N$—M—OH (in the formula, M has the same meaning as that defined above) are condensed to synthesize a compound represented by general formula (XII):

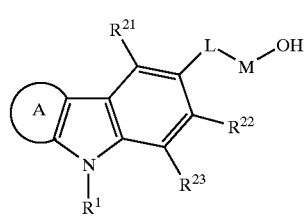

(XII)

(in the formula, A, $R^1$, $R^{21}$, $R^{22}$, $R^{23}$ and M have the same meanings as those defined above). For the condensation reaction, usual DCC condensation, DCC/HOBt method or WSC method can be used. The reaction temperature is usually −20° C. to 100° C., preferably 0° C. to room temperature. The reaction time is usually 10 minutes to 3 days, preferably 1 hour to 1 day.

Then, the compound represented by the general formula (XII) is converted into a compound represented by the general formula (XIII):

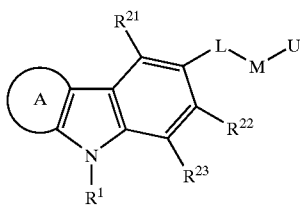

(XIII)

(in the formula, A, $R^1$, $R^{21}$, $R^{22}$, $R^{23}$ and M have the same meanings as those defined above, and U represents a leaving group). As the leaving group represented by U, tosyl group, mesyl group, a halogen atom or the like is preferred. The reaction conditions of usual tosylation can be applied when U is tosyl group, and the method using a reaction with tosyl chloride in pyridine is preferred. The reaction temperature is usually −20° C. to 100° C., preferably 0° C. to room temperature. The reaction time is usually 10 minutes to 3 days, preferably 1 hour to 1 day. When U is a halogen atom, conditions for usual halogenation can be used. For example, when U is a bromine atom, the method of using carbon tetrabromide and phosphine in dichloromethane at room temperature is preferred.

By reacting the compound represented by the general formula (XIII) and a compound represented as H—X—Y in an organic solvent in the presence of a base, a compound of the general formula (I) (wherein L is —NH—CO— or —CO—$NR^3$— and X is —S—, —O—, —$NR^4$— or a single bond) can be obtained. In this case, the reaction temperature is usually −20° C. to 100° C., preferably 0° C. to room temperature. The reaction time is usually 10 minutes to 3 days, preferably 1 hour to 1 day. As a preferred organic solvent, acetonitrile can be used, and preferred bases include triethylamine and potassium carbonate.

If a compound of the general formula: $X^2$—M—X—Y (in the formula, $X^2$, M, X and Y have the same meanings as those defined above) is readily available, a compound of the general formula (VII) and the compound of the general formula: $X^2$—M—X—Y can be condensed to obtain a compound of the general formula (I) (wherein L is —NH—CO— and X is —S—, —O—, —$NR^4$— or a single bond). Further, in connection with the aforementioned preparation method, a compound of the general formula (I) (wherein L is —NH—CO— or —CO—$NR^3$— and X is —S—, —O—, —$NR^4$— or a single bond) can also be obtained by condensation with a compound of the general formula: $R^3$HN—M—X—Y (in the formula, $R^3$, M, X and Y have the same meanings as those defined above). Further, the order of the reactions of the aforementioned production method may be changed depending on properties of a target compound.

<Preparation Method 6>

Method for preparing compounds represented by the general formula (I) where X is —$NR^4$— and Y is a dialkylphosphoryl group A compound represented by general formula (XIV):

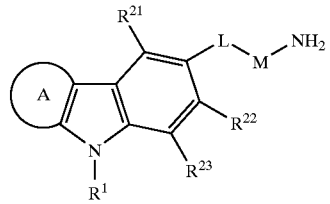

(XIV)

obtained by Preparation method 1 or Preparation method 3 described above can be reacted with Cl—Y (Y represents a dialkylphosphoryl group) to produce a compound represented by the general formula (I) where X is —$NR^4$— and Y is a dialkylphosphoryl group.

The reaction can be performed in an organic solvent in the presence of a base. The reaction temperature is usually −20° C. to 100° C., preferably 0° C. to room temperature. The reaction time is usually 10 minutes to 3 days, preferably 1 hour to 1 day. As a preferred organic solvent, acetonitrile can be used, and preferred bases include triethylamine and potassium carbonate. A compound represented by the general formula (XIV) can also be synthesized by tosylating a compound represented by the general formula (XII), converting the product into an azide, and subjecting the resultant to hydrogenolysis.

In Preparation methods 1 to 6, the substituents on the hydrocarbon ring group represented by A, $R^{21}$, $R^{22}$, $R^{23}$ and the like may be protected beforehand with suitable protective groups, if needed, and they may be deprotected by a suitable method in the final step or an intermediate step.

A compound represented by the general formula (XXI) encompassed by the general formula (I) can be prepared, for example, according to the following method. However, the methods for preparing the compound are not limited to the following methods.

<Preparation Method 7>

A compound represented by the general formula (XXII):

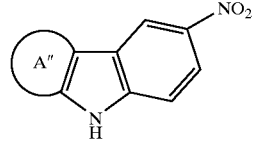

(XXIII)

(in the formula, A″ has the same meaning as that defined above), which can be prepared by the method described in Journal of Chemical Society, p.833 (1924) or the like, can be reacted with a compound represented by the general formula: $R^{101}$—$X^1$ (in the formula, $R^{101}$ has the same meaning as that defined above, and $X^1$ represents a leaving group) in an organic solvent in the presence of a base to produce a compound represented by the general formula (XXIV):

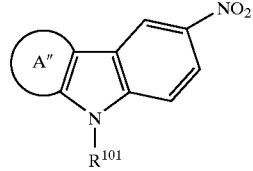

(XXIV)

(in the formula, A″ and $R^{101}$ have the same meanings as those defined above).

As the leaving group $X^1$ of $R^{101}$—$X^1$ used in the aforementioned reaction, a halogen atom, tosyl group or mesyl group is preferred. The type of the organic solvent used for the reaction is not particularly limited so long as the solvent is inert in the reaction. For example, generally used organic solvents such as acetonitrile, tetrahydrofuran, dimethylformamide, dimethylacetamide, dimethyl sulfoxide and acetone may be used. Examples of the base to be used include, for example, generally used bases such as sodium hydride, sodium hydroxide, potassium carbonate, sodium carbonate, sodium hydrogencarbonate and triethylamine. The reaction temperature is usually −20° C. to 100° C., preferably 0° C. to room temperature. The reaction time is usually 1 minute to 3 days, preferably 1 hour to 1 day.

Subsequently, the nitro group of the compound represented by the general formula (XXIV) can be reduced for convertion into a compound represented by the general formula (XXV):

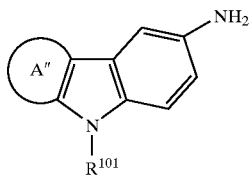

(XXV)

(in the formula, A" and $R^{101}$ have the same meanings as defined above). Various generally used methods can be used as the reduction method, and a typical method includes reduction using iron. Examples of preferred reaction solvents include acetic acid and isopropyl alcohol, and when isopropyl alcohol is used, the reaction can be performed in the presence of ammonium chloride. The reaction temperature is usually 0° C. to 100° C., preferably room temperature to 70° C. The reaction time is usually 1 minute to 3 days, preferably 1 hour to 1 day.

Then, the compound represented by the general formula (XXV) and phenyl chloroformate can be reacted in an organic solvent in the presence of a base to produce a compound represented by the general formula (XXVI):

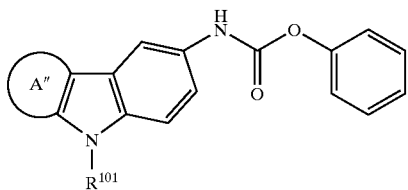

(XXVI)

(in the formula, A" and $R^{101}$ have the same meanings as those defined above). The condensation can be performed in a generally used organic solvent such as tetrahydrofuran, dimethylformamide, dimethylacetamide, dichloromethane and acetonitrile in the presence of a generally used base such as potassium carbonate and triethylamine. The reaction temperature of the condensation reaction is usually −20° C. to 100° C., preferably −20° C. to room temperature. The reaction time is usually 10 minutes to 3 days, preferably 1 hour to 1 day.

The compound of the general formula (XXVI) obtained above can be reacted with a compound represented by the general formula: $HN(R^{102})(R^{103})$ (in the formula, $R^{101}$ and $R^{103}$ have the same meanings as those defined above) in the presence or absence of an organic solvent and in the presence or absence of a base to obtain a compound represented by the general formula (XXI) of the present invention. As the organic solvent, generally used organic solvents such as tetrahydrofuran, dimethylformamide, dimethylacetamide, dichloromethane and acetonitrile or a mixed solvent thereof may be used. As the base, generally used bases such as potassium carbonate and triethylamine can be used. The reaction temperature of the condensation reaction is usually 0° C. to 200° C., preferably room temperature to 120° C. The reaction time is usually 10 minutes to 3 days, preferably 1 hour to 1 day.

A compound represented by the general formula (XXV) obtained by the aforementioned preparation method can also be condensed with a compound of the general formula: $(R^{102})(R^{103})N$—CO—$X^1$ (in the formula, $R^{102}$, $R^{103}$, and $X^1$ have the same meanings as those defined above) to obtain a compound of the general formula (XXI). Furthermore, it is also possible to reduce a compound represented by the general formula (XXIII) for conversion into an amino compound, and then condense the resulting compound with a compound represented by the general formula: defined above) to produce a compound represented by the general formula (XXVII):

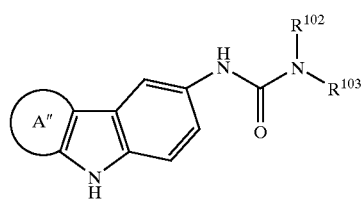

(XXVII)

(in the formula, $R^{102}$, $R^{103}$ and $X^1$ have the same meanings as those defined above), which can further be reacted in a final step with a compound represented by the general formula: $R^{101}$—$X^1$ (in the formula, $R^{101}$ has the same meaning as defined above, and $X^1$ represents a leaving group) in an organic solvent in the presence of a base to produce a compound represented by the general formula (XXI).

Methods for preparing typical compounds will be specifically explained in detail in the examples of the specification. Therefore, those skilled in the art will be able to produce any of the compounds represented by the aforementioned general formula (I) or (IV) based on explanations in the foregoing general preparations and examples by suitably choosing starting compounds, reagents, reaction conditions and the like, and appropriately modifying or altering the methods described in the examples as required. When the aforementioned reactions are performed, a reaction yield may be increased by suitably protecting a reactive functional group. A protective group can be suitably chosen depending on the type of the reactive functional group, and the choosing may become easier by referring to, for example, Protective Groups in Organic Synthesis, T. W. Greene, John Wiley & Sons, Inc., 1981 and the like.

The compounds of the present invention represented by the general formula (I) and the compounds represented by the general formula (IV) are characterized by having affinity for the Y type receptors of NPY, in particular, having selective affinity for the Y5 receptor. Therefore, the compounds of the present invention represented by the general formula (I) and the compounds represented by the general formula (IV) have a controlling action on the expression of NPY action and are useful for prophylactic and/or therapeutic treatment of various kinds of diseases in which NPY is involved, for example, cardiovascular diseases such as hypertension, kidney diseases, cardiac diseases and angiospasm, central system diseases such as hyperphagia, melancholia, epilepsy and dementia, metabolic diseases such as obesity, diabetes, hyperlipidemia and hormone abnormality, inappetence of cancer patients, glaucoma and the like. In particular, since the Y5 receptor mostly relates to control of ingestion, the aforementioned compounds have ingestion controlling action for hyperphagia and inappetence of cancer patients, and in addition, they are useful for prophylactic and/or therapeutic treatment of central system diseases such as melancholia, epilepsy and dementia, metabolic diseases such as obesity, diabetes, hypercholesterolemia, hyperlipidemia, arteriosclerosis and hormone abnormality and the like.

The medicaments provided by the present invention are characterized to comprise a substance selected from the group consisting of the compounds represented by the general formula (I) and physiologically acceptable salts thereof, and hydrates thereof and solvates thereof, or a substance selected from the group consisting of the compounds represented by the general formula (IV) and physiologically acceptable salts thereof, and hydrates thereof and solvates thereof as an active ingredient. The medicaments of the present invention can be administered orally or parenterally. Examples of parenteral administration routes include intrabronchial, intrarectal, subcutaneous, intramuscular, and intravenous administrations and the like. While the aforementioned substance, per se, may be administered as the medicament of the present invention, it is generally desirable to produce a pharmaceutical composition by using one or more kinds of additives for pharmaceutical preparations, and administer the composition to a patient as the medicament of the present invention. Examples of pharmaceutical preparations suitable for oral administration include, for example, tablets, granules, subtilized granules, powders, syrups, solutions, capsules, chewable tablets, suspensions and the like, and examples of pharmaceutical preparations suitable for parenteral administration include, for example, injections, drip infusions, inhalants, sprays, suppositories, transdermal preparations, transmucosal preparations, eye drops, ear drops, nose drops, patches and the like. It is also possible to provide liquid preparations such as injections and drip infusions as, for example, lyophilized powdery pharmaceutical preparations and dissolve or suspend the preparations in water or other suitable medium (for example, physiological saline, glucose infusion, buffer and the like) upon use.

The additives for pharmaceutical preparations can be suitably chosen depending on the form of the pharmaceutical composition and types thereof are not particularly limited. Examples thereof include, for example, stabilizers, surfactants, plasticizers, lubricants, solubilizers, buffers, sweetening agents, base materials, sorbents, corrigents, binders, suspending agents, brighteners, coating agents, flavoring agents and perfumes, wetting agents, wetting modifiers, fillers, antifoams, peptizing agents, refrigerants, colorants, sugar coating agents, isotonic agents, pH modifiers, softeners, emulsifiers, tackifiers, adhesion enhancers, viscous agents, thickening agents, vesicants, excipients, dispersing agents, propellants, disintegrating agents, disintegrating aids, aromatics, moisture-proofing agents, antiseptics, preservatives, soothing agents, solvents, dissolving agents, dissolving aids, fluidizing agents and the like, and two or more of these can be used in combination. Since specific examples of these additives for pharmaceutical preparations are explained in, for example, Japanese Pharmaceutical Excipients (Ed. by Japan Pharmaceutical Excipients Council, published by Yakuji Nippo, Ltd.), those skilled in the art can choose suitable additives for pharmaceutical preparations depending on a form of the pharmaceutical composition, and can produce the pharmaceutical composition in a desired form according to usual methods used in this field. In general, the aforementioned pharmaceutical composition can be prepared so as to contain the aforementioned substance as an active ingredient in an amount of 1.0 to 100% (W/W), preferably 1.0 to 60% (W/W).

More specifically, usable additives for pharmaceutical preparations include gelatin, lactose, sucrose, titanium oxide, starch, crystalline cellulose, hydroxypropylmethylcellulose, carboxymethylcellulose, corn starch, microcrystalline wax, white petrolatum, magnesium aluminometasilicate, anhydrous calcium phosphate, citric acid, tribasic sodium citrate, hydroxypropylcellulose, sorbitol, sorbitan esters of fatty acid, polyisobate, sucrose esters of fatty acid, polyoxyethylene hydrogenated castor oil, polyvinylpyrrolidone, magnesium stearate, light anhydrous silicic acid, talc, vegetable oil, benzyl alcohol, gum arabic, propylene glycol, polyalkylene glycol, cyclodextrin, and hydroxypropylcyclodextrin. However, the additives for pharmaceutical preparations are not limited to these examples.

Doses and administration frequencies of the medicaments of the present invention are not particularly limited, and suitable doses and administration frequencies can be determined depending on various factors such as purpose of administration, i.e., therapeutic or prophylactic purpose, type of a disease, the age, body weight and symptoms of a patient and the like. As for oral administration, the medicament can be administered once to several times a day in an amount of 0.1 to 100 mg/kg based on the weight of an active ingredient as a daily dose for an adult. As for parenteral administration, the medicament may preferably be administered once to several times a day in an amount of 0.001 to 10 mg/kg based on the weight of an active ingredient as a daily dose for an adult.

EXAMPLES

The present invention will be more specifically explained with reference to the following examples. However, the scope of the present invention is not limited to the following examples. The compound numbers used in the examples correspond to the compound numbers of the compounds specifically mentioned above.

Example 1

Synthesis of Compound 1-1

2.00 g of 5-amino-n-valeric acid was dissolved in 25 mL of 1 N aqueous sodium hydroxide, and the solution was added with of 3.87 g of 1-naphthalenesulfonyl chloride, and stirred at room temperature for 4 hours. After the reaction mixture was made acidic with 4 N hydrochloric acid, the mixture was diluted with water and extracted with ethyl acetate. The organic layer was washed with water and saturated brine and concentrated under reduced pressure. Then, the sulfonamide (0.73 g) obtained above and 0.50 g of 3-amino-9-ethylcarbazole were dissolved in 5.0 mL of dimethylformamide, added with 0.45 g of WSC (hydrochloride), and then stirred at room temperature for 3 hours. The reaction mixture was added with water and extracted with ethyl acetate, and the organic layer was successively washed with 1 N aqueous sodium hydroxide, 0.4 N hydrochloric acid and saturated brine, dried over anhydrous sodium sulfate, and concentrated under reduced pressure. The resulting residue was washed with chloroform and filtered to obtain 0.83 g of Compound 1-1.

$^1$H-NMR (300 MHz, DMSO-$d_6$) δ1.30 (t, 3H), 1.41 (m, 2H), 1.54 (m, 2H), 2.20 (t, 2H), 2.83 (m, 2H), 4.40 (q, 2H), 7.16 (dd, 1H), 7.4–7.8 (m, 7H), 7.9–8.3 (m, 5H), 8.36 (s, 1H), 8.66 (d, 1H), 9.80 (s, 1H)

FAB-MS (m/e) 500 (M+H)$^+$

The compounds of Example 2 to Example 7 were synthesized in the same manner as in Example 1 by using raw materials corresponding to each of the desired compounds instead of the raw materials used in Example 1.

Example 2

Compound 1-2

$^1$H-NMR (300 MHz, DMSO-$d_6$) δ1.2–1.6 (m, 6H), 1.30 (t, 3H), 2.20 (t, 2H), 2.79 (m, 2H), 4.40 (q, 2H), 7.16 (dd, 1H), 7.4–7.8 (m, 7H), 7.9–8.3 (m, 5H), 8.39 (s, 1H), 8.66 (d, 1H), 9.80 (s, 1H)

FAB-MS (m/e) 514 (M+H)$^+$

Example 3

Compound 1-3

$^1$H-NMR (300 MHz, DMSO-$d_6$) δ1.0–1.4 (m, 8H), 1.30 (t, 3H), 1.49 (m, 2H), 2.25 (t, 2H), 2.77 (m, 2H), 4.41 (q, 2H), 7.18 (dd, 1H), 7.4–7.8 (m, 7H), 7.9–8.3 (m, 5H), 8.40 (s, 1H), 8.66 (d, 1H), 9.84 (s, 1H)

FAB-MS (m/e) 541 (M+H)$^+$

Example 4

Compound 1-4

$^1$H-NMR (300 MHz, DMSO-$d_6$) δ1.29 (t, 3H), 2.53 (m, 2H), 3.11 (m, 2H), 4.39 (q, 2H), 7.17 (t, 1H), 7.4–7.8 (m, 7H), 7.9–8.3 (m, 5H), 8.34 (s, 1H), 8.68 (d, 1H), 9.92 (s, 1H)

FAB-MS (m/e) 472 (M+H)$^+$

Example 5

Compound 1-5

$^1$H-NMR (300 MHz, DMSO-$d_6$) δ1.30 (t, 3H), 1.70 (m, 2H), 2.30 (t, 2H), 2.85 (m, 2H), 4.40 (q, 2H), 7.17 (dd, 1H), 7.4–7.8 (m, 7H), 7.9–8.3 (m, 5H), 8.34 (s, 1H), 8.67 (d, 1H), 9.82 (s, 1H)

FAB-MS (m/e) 486 (M+H)$^+$

Example 6

Compound 1-6

$^1$H-NMR (300 MHz, DMSO-$d_6$) δ1.30 (t, 3H), 1.4–1.7 (m, 4H), 2.26 (t, 2H), 2.82 (m, 2H), 4.41 (q, 2H), 7.17 (dd, 1H), 7.4–7.9 (m, 8H), 8.0–8.2 (m, 4H), 8.37 (s, 1H), 8.42 (d, 1H), 9.83 (s, 1H)

FAB-MS (m/e) 500 (M+H)$^+$

Example 7

Compound 1-7

$^1$H-NMR (300 MHz, DMSO-$d_6$) δ1.2–1.7 (m, 6H), 1.35 (t, 3H), 2.27 (t, 2H), 2.84 (m, 2H), 4.26 (q, 2H), 6.44 (bs, 1H), 7.1–7.7 (m, 6H), 7.84 (s, 1H), 7.96 (dd, 2H), 8.20 (m, 1H), 8.27 (d, 1H), 8.40 (m, 1H), 8.96 (d, 1H)

FAB-MS (m/e) 515 (M+H)$^+$

Example 8

Synthesis of Compound 1-8

N-Boc-6-aminocaproic acid (7.58 g) prepared by the method described in a Journal of Medicinal Chemistry (J. Med. Chem., 35, p.272 (1993)) and 7.58 g of 3-amino-9-ethylcarbazole were dissolved in 75 mL of dimethylformamide, and the solution was added with 10.4 g WSC hydrochloride and stirred at room temperature for 3.5 hours. The reaction mixture was added with water and extracted with ethyl acetate. The organic layer was washed with 1 N aqueous sodium hydroxide, 10% aqueous citric acid and saturated brine, then dried over anhydrous magnesium sulfate and concentrated under reduced pressure. The residue was purified by silica gel chromatography (eluent: hexane/ethyl acetate=1/1) to obtain 10.3 g of 3-(N-Boc-6-aminocaproyl)amino-9-ethylcarbazole.

The resulting 3-(N-Boc-6-aminocaproyl)amino-9-ethylcarbazole (6.01 g) was dissolved in 60 mL of dioxane, and the solution was added with 60 mL of 4 N hydrochloric acid in dioxane, and stirred under ice cooling for 30 minutes and then at room temperature for 1.5 hours. The reaction mixture was added with ether, and the resulting residue was washed with ether and dissolved in water. The solution was made basic with 1 N sodium hydroxide and then extracted with ethyl acetate. The obtained organic layer was washed with saturated aqueous sodium chloride and dried over anhydrous magnesium sulfate, and the solvent was evaporated under reduced pressure to obtain 0.44 g of 6-aminocaproylamino-9-ethylcarbazole.

The resulting 6-aminocaproylamino-9-ethylcarbazole (530 mg) was dissolved in 18 mL of acetonitrile, added with 494 mg of sodium hydrogencarbonate and 255 mg of nicotinic acid chloride, and stirred at room temperature for 3 hours. The reaction mixture was added with water, neutralized with 10% aqueous citric acid and then extracted with ethyl acetate. The organic layer was dried over anhydrous magnesium sulfate, and the solvent was evaporated under reduced pressure. Then the residue was purified by silica gel chromatography (eluent: chloroform/methanol= 96/4) to obtain 236 mg of Compound 1-8.

$^1$H-NMR (300 MHz, CDCl$_3$) δ1.2–1.7 (m, 6H), 1.31 (t, 3H), 2.31 (t, 2H), 3.34 (m, 2H), 4.17 (q, 2H), 7.0–7.2 (m, 3H), 7.22–7.46 (m, 3H), 7.60 (brs, 1H), 7.87 (dd, 1H), 8.06 (dd, 1H), 8.20 (d, 1H), 8.51 (m, 1H), 8.59 (d, 1H), 9.01 (d, 1H)

FAB-MS (m/e) 428 M$^+$

Example 9

Synthesis of Compound 1-9

6-Nitro-1,2,3,4-tetrahydrocarbazole (5.04 g) prepared by the method described in Journal of Chemical Society, p.833 (1924) was dissolved in 50 mL of acetone, and the solution was added with 2.25 g of potassium hydroxide and 8.45 g of isopropyl iodide, warmed to 50° C. and stirred for 3 hours. The reaction mixture was added with water and the deposited precipitates were collected to obtain 2.60 g of N-isopropyl-6-nitro-1,2,3,4-tetrahydrocarbazole. The resulting N-isopropyl-6-nitro-1,2,3,4-tetrahydrocarbazole (2.60 g) was dissolved in 100 mL of acetic acid, and the solution was added with 2.75 g of iron powder, warmed to 50° C., and stirred for 3 hours. The reaction mixture was filtered and the filtrate was diluted by adding water. The reaction mixture was made basic with 1 N sodium hydroxide and extracted with dichloromethane. The organic layer was dried over anhydrous sodium sulfate, and the solvent was evaporated under reduced pressure. The residue was purified by silica gel chromatography (eluent: dichloromethane/ethyl acetate= 7/3) to obtain 1.35 g of N-isopropyl-6-amino-1,2,3,4-tetrahydrocarbazole.

Then, 5.43 g of 6-aminocaproic acid methyl ester hydrochloride, 6.78 g of 1-naphthalenesulfonyl chloride and 3.03 g of triethylamine were dissolved in 50 mL of dichloromethane and stirred for 12 hours. The reaction mixture was washed with 10% aqueous citric acid and then with saturated aqueous sodium hydrogencarbonate, and dried over anhydrous sodium sulfate. The solvent was evaporated under reduced pressure, and then the residue was purified by silica gel chromatography (eluent: hexane/ethyl acetate=7/3) to obtain 5.50 g of 6(1-naphthalenesulfonyl)aminocaproic acid methyl ester. The resulting 6-(1-naphthalenesulfonyl) aminocaproic acid methyl ester (3.35 g) was dissolved in methanol, and the solution was added with 20 mL of 1 N sodium hydroxide, and stirred for 3 hours. Then, the methanol was evaporated under reduced pressure, and the residue was made acidic with 1 N hydrochloric acid and extracted with ethyl acetate. The organic layer was dried over anhydrous sodium sulfate, and the solvent was evaporated under reduced pressure to obtain 3.02 g of 6-(1-naphthalenesulfonyl)aminocaproic acid.

The N-isopropyl-6-amino-1,2,3,4-tetrahydrocarbazole (228 mg) obtained above, 6-(1-naphthalenesulfonyl) aminocaproic acid (321 mg) obtained above, DCC (226 mg) and HOBt (153 mg) were dissolved in 3 mL of DMF, and stirred at room temperature for 12 hours. The reaction mixture was filtered, and the filtrate was added with 10% aqueous citric acid and extracted with ethyl acetate. The organic layer was washed with saturated aqueous hydrogencarbonate solution and dried over anhydrous sodium sulfate. The solvent was evaporated under reduced pressure, and the residue was purified by silica gel chromatography (eluent: hexane/ethyl acetate=7/3) to obtain 250 mg of Compound 1-9.

$^1$H-NMR (300 MHz, CDCl$_3$) δ1.1–1.6 (m, 6H), 1.52 (d, 6H), 1.7–2.0 (m, 4H), 2.15 (t, 2H), 2.54–2.76 (m, 4H), 2.86 (m, 2H), 4.52 (sep., 1H), 5.33 (t, 1H), 7.1–7.7 (m, 6H), 7.90 (d, 1H), 8.01 (d, 1H), 8.23 (d, 1H), 8.68 (d, 1H)

FAB-MS (m/e) 532 (M+H)$^+$

Example 10

Synthesis of Compound 1-10

50 g of N-ethylcarbazole-3-carboxaldehyde was dissolved in 1 L of acetone, and the solution was added with 70.6 g of potassium permanganate under ice cooling, stirred for 3 hours, then added with 100 mL of methanol and filtered. The filtrate was evaporated under reduced pressure, and the residue was dissolved in aqueous sodium hydrogencarbonate. Then, the solution was made acidic by adding concentrated hydrochloric acid, and the deposited precipitates were collected to obtain 33 g of N-ethylcarbazole-3-carboxylic acid.

The resulting N-ethylcarbazole-3-carboxylic acid (4.78 g) and ωN-Boc-amino-pentylamine (4.04 g) prepared by the method described in Journal of Medicinal Chemistry, 40, p.2643 (1997), DCC (4.32 g) and HOBt (3.06 g) were dissolved in 50 mL of DMF, and the solution was stirred at room temperature for 6 hours. The reaction mixture was filtered, and the filtrate was added with 10% aqueous citric acid and extracted with ethyl acetate. The organic layer was washed with saturated aqueous hydrogencarbonate solution and dried over anhydrous sodium sulfate. The solvent was evaporated under reduced pressure, and the residue was dissolved in 100 mL of dioxane and added with 100 mL of 4 N hydrochloric acid in dioxane, and stirred at room temperature for 30 minutes. The reaction mixture was added with hexane and the deposited precipitates were collected to obtain 4.02 g of N-ethyl-3-(ω-aminopentylaminocarbonyl)-carbazole.

The resulting N-ethyl-3-(ω-aminopentylaminocarbonyl)-carbazole (198 mg) and potassium carbonate (310 mg) were dissolved in 2 mL of DMF, added with methanesulfonyl chloride (45 mL), and stirred at room temperature for 3 hours. The reaction mixture was added with water and extracted with dichloromethane, and then the organic layer was washed with 10% aqueous citric acid, water and saturated aqueous sodium chloride, and dried over anhydrous sodium sulfate. The solvent was evaporated under reduced pressure, and the residue was recrystallized from a mixture of ethyl acetate and hexane to obtain 85 mg of Compound 1-10.

$^1$H-NMR (300 MHz, CDCl$_3$) δ1.3–1.9 (m, 6H), 1.50 (t, 3H), 2.98 (s, 3H), 3.29 (m, 2H), 3.58 (m, 2H), 4.39 (q, 2H), 4.50 (t, 1H), 6.34 (t, 1H), 7.20–7.30 (m, 1H), 7.4–7.6 (m, 3H), 7.92 (dd, 1H), 8.16 (d, 1H), 8.58 (d, 1H)

FAB-MS (m/e) 401 M$^+$

The compounds of Example 11 to Example 24 were synthesized in the same manner as in Example 10 by using raw materials corresponding to each of the desired compounds instead of the raw materials used in Example 10.

Example 11

Compound 1-11

$^1$H-NMR (300 MHz, CDCl$_3$) δ1.04 (t, 3H, J=7.4Hz), 1.4–1.9 (m, 10H), 1.44 (t, 3H), 2.9–3.0 (m, 2H), 3.2–3.4 (m, 2H), 3.53 (m, 2H), 4.38 (q, 2H), 4.48 (brs, 1H), 6.44 (brs, 1H), 7.2–7.6 (m, 4H), 7.90 (dd, 1H), 8.15 (d, 1H), 8.57 (d, 1H)

FAB-MS (m/e) 430 (M+H)$^+$

Example 12

Compound 1-12

$^1$H-NMR (300 MHz, CDCl$_3$) δ0.87 (t, 3H), 1.4–1.7 (m, 15H), 1.44 (t, 3H), 2.90 (m, 2H), 3.13 t (m, 2H), 3.53 (m, 2H), 4.3–4.5 (m, 3H), 6.4 (brs, 1H), 7.2–7.6 (m, 4H), 7.94 (dd, 1H), 8.18 (d, 1H), 8.57 (d, 1H)

FAB-MS (m/e) 500 (M+H)$^+$

Example 13

Compound 1-13

$^1$H-NMR (300 MHz, CDCl$_3$) δ1.3–1.9 (m, 6H), 1.36 (d, 6H), 1.43 (t, 3H), 3.1–3.24 (m, 3H), 3.52 (m, 2H), 4.3–4.5 (m, 3H), 6.50 (br, 1H), 7.2–7.6 (m, 4H), 7.92 (dd, 1H), 8.12 (d, 1H), 8.57 (d, 1H)

FAB-MS (m/e) 430 (M+H)$^+$

Example 14

Compound 1-14

$^1$H-NMR (300 MHz, CDCl$_3$) δ1.3–1.7 (m, 6H), 1.42 (t, 3H), 3.06 (br, 2H), 3.48 (m, 2H), 4.38 (q, 2H), 4.9 (br, 1H), 6.35 (br, 1H), 7.2–7.7 (m, 6H), 7.8–8.0 (m, 5H), 8.18 (d, 1H), 8.43 (d, 1H), 8.56 (d, 1H)

FAB-MS (m/e) 514 (M+H)$^+$

Example 15

Compound 1-15

$^1$H-NMR (300 MHz, CDCl$_3$) 1.4–1.8 (m, 6H), 1.44 (t, 3H), 3.02 (m, 2H), 3.49 (m, 2H), 4.38 (q, 2H), 4.9 (br, 1H), 6.40 (br, 1H), 7.2–7.6 (m, 7H), 7.8–8.0 (m, 3H), 8.18 (d, 1H), 8.57 (d, 1H)

FAB-MS (m/e) 464 (M+H)$^+$

Example 16

Compound 1-16

$^1$H-NMR (300 MHz, CDCl$_3$) δ1.4–1.8 (m, 6H), 1.45 (t, 3H), 2.90 (m, 2H), 3.42 (m, 2H), 4.39 (q, 2H), 6.3 (br, 1H), 6.40 (br, 1H), 7.2–7.7 (m, 6H), 7.92 (dd, 1H), 8.08 (dd, 1H), 8.18 (dd, 1H), 8.28 (dd, 1H), 8.48 (dd, 1H), 8.54 (d, 1H), 9.04 (dd, 1H)

FAB-MS (m/e) 515 (M+H)$^+$

Example 17

Compound 1-17

$^1$H-NMR (300 MHz, CDCl$_3$) δ1.2–1.5 (m, 6H), 1.38 (t, 3H), 2.8–2.9 (m, 2H), 2.84 (s, 6H), 3.33 (m, 2H), 4.30 (q, 2H), 5.34 (t, 1H), 6.56 (t, 1H), 7.1–7.5 (m, 7H), 7.92 (dd, 1H), 8.07 (d, 1H), 8.20 (d, 1H), 8.33 (d), 8.58 (d, 1H)

FAB-MS (m/e) 557 (M+H)$^+$

Example 18

Compound 1-18

$^1$H-NMR (300 MHz, CDCl$_3$) δ1.11 (d, 6H), 1.4–1.7 (m, 6H), 1.45 (t, 3H), 2.34 (sep., 1H), 3.29 (m, 2H), 3.54 (m, 2H), 4.39 (q, 3H), 5.65 (br, 1H), 6.42 (br, 1H), 7.2–7.6 (m, 4H), 7.91 (dd, 1H), 8.14 (d, 1H), 8.58 (d, 1H)

FAB-MS (m/e) 394 (M+H)$^+$

Example 19

Compound 1-19

$^1$H-NMR (300 MHz, CDCl$_3$) δ1.0–1.8 (m, 16H), 1.40 (t, 3H), 2.0–2.1 (m, 1H), 3.29 (m, 2H), 3.41 (m, 2H), 4.38 (q, 2H), 5.64 (t, 1H), 6.48 (t, 1H), 7.2–7.6 (m, 4H), 7.94 (dd, 1H) 8.18 (d, 1H), 8.60 (d, 1H)

FAB-MS (m/e) 434 (M+H)$^+$

Example 20

Compound 1-20

$^1$H-NMR (300 MHz, CDCl$_3$) δ1.4–2.0 (m, 21H), 1.45 (t, 3H), 3.27 (m, 2H), 3.52 (m, 2H), 4.36 (q, 2H), 5.70 (br, 1H), 6.60 (br, 1H), 7.2–7.6 (m, 4H), 7.94 (dd, 1H), 8.18 (d, 1H), 8.59 (d, 1H)

FAB-MS (m/e) 486 (M+H)$^+$

Example 21

Compound 1-21

$^1$H-NMR (300 MHz, CDCl$_3$) δ1.4–1.9 (m, 6H), 1.45 (t, 3H), 3.45–3.60 (m, 4H), 4.39 (q, 2H), 6.40 (br, 1H), 6.42 (br, 1H), 7.2–7.6 (m, 7H), 7.70–7.80 (m, 2H), 7.90 (dd, 1H), 8.12 (d, 1H), 8.56 (d, 1H)

FAB-MS (m/e) 428 (M+H)$^+$

Example 22

Compound 1-22

$^1$H-NMR (300 MHz, CDCl$_3$) δ1.41 (t, 3H), 1.5–1.9 (m, 6H), 3.50–3.60 (m, 4H), 4.30 (q, 2H), 6.30 (br, 1H), 6.42 (br, 1H), 7.1–7.6 (m, 8H), 7.80–7.90 (m, 3H), 8.06 (d, 1H), 8.28 (dd, 1H), 8.51 (d, 1H)

FAB-MS (m/e) 478 (M+H)$^+$

Example 23

Compound 1-23

$^1$H-NMR (300 MHz, CDCl$_3$) δ1.43 (t, 3H), 1.5–1.6 (m, 2H), 1.6–1.8 (m, 4H), 3.45–3.60 (m, 4H), 4.36 (q, 2H), 6.60 (t, 1H), 7.08 (t, 1H), 7.2–7.3 (m, 2H), 7.37 (d, 1H), 7.43 (d, 1H), 7.50 (dd), 7.86 (dd, 1H), 8.08 (d, 1H), 8.16 (ddd, 1H), 8.53 (d, 1H), 8.61 (d, 1H), 9.10 (d, 1H)

FAB-MS (m/e) 429 (M+H)$^+$

Example 24

Compound 1-24

$^1$H-NMR (300 MHz, CDCl$_3$) δ1.35–1.50 (m, 2H), 1.36 (t, 3H), 1.50–1.70 (m, 4H), 2.74 (s, 6H), 3.10 (m, 2H), 3.46 (m, 2H), 4.28 (q, 2H), 4.90 (br, 1H), 6.78 (br, 1H), 7.21 (dd, 1H), 7.31 (d,1H), 7.37 (d, 1H), 7.46 (dd, 1H), 7.92 (dd, 1H), 8.08 (d, 1H), 8.59 (d, 1H)

FAB-MS (m/e) 431 (M+H)$^+$

Example 25

Synthesis of Compound 1-25

N-Ethyl-3-(ω-aminopentylaminocarbonyl)-carbazole (162 mg) obtained by the method of Example 10, indole-5-carboxylic acid (95 mg), DCC (103 mg) and HOBt (77 mg) were dissolved in 3 mL of DMF and the solution was stirred at room temperature for 24 hours. The reaction mixture was filtered, and the filtrate was added with 10% aqueous citric acid and extracted with dichloromethane. Then, the organic layer was washed with saturated aqueous hydrogencarbonate solution and dried over anhydrous sodium sulfate, and then the solvent was evaporated under reduced pressure. The residue was purified by silica gel chromatography (eluent: hexane/ethyl acetate=7/3) to obtain 250 mg of Compound 1-25.

$^1$H-NMR (300 MHz, CDCl$_3$) δ1.43 (t, 3H), 1.5–1.6 (m, 2H), 1.64–1.80 (m, 4H), 3.50–3.60 (m, 4H), 4.58 (q, 2H), 6.37 (br, 1H), 6.45 (br, 1H), 6.54 (br, 1H), 7.20–7.38 (m, 4H), 7.42 (d,1H), 7.49 (ddd, 1H), 7.63 (dd, 1H), 7.89 (dd, 1H), 8.08 (d, 1H), 8.11 (d, 1H), 8.42 (br, 1H), 8.58 (d, 1H)

FAB-MS (m/e) 467 (M+H)$^+$

The compound of Example 26 was synthesized in the same manner as in Example 25 by using raw materials corresponding to the desired compound instead of the raw materials used in Example 25.

Example 26

Compound 1-26

$^1$H-NMR (300 MHz, CD$_3$OD) δ1.41 (t, 3H), 1.46–1.82 (m, 6H), 3.40–3.52 (m, 4H), 4.30 (q, 2H), 7.22 (ddd, 1H), 7.44–7.56 (m,3H), 7.78 (d, 1H), 7.88 (dd, 1H), 7.93 (dd, 1H), 8.04 (d, 1H), 8.35 (s, 1H), 8.57 (d, 1H)

FAB-MS (m/e) 469 (M+H)$^+$

Example 27

Synthesis of Compound 1-27

Under ice cooling, 5.29 g of aminoethylthioethylamine was added dropwise with 120 mL of acetonitrile solution in which 1.00 g of 1-naphthalenesulfonyl chloride was dissolved, and the mixture was stirred at room temperature for two days. The reaction mixture was evaporated under reduced pressure, and then the residue was added with 500 mL of water and extracted with dichloromethane. The organic layer was dried over anhydrous sodium sulfate, and then the solvent was evaporated under reduced pressure to obtain 1.50 g of 1-naphthalenesulfonylaminoethylthioethylamine.

The resulting 1-naphthalenesulfonylaminoethylthioethylamine (600 mg), N-ethylcarbazole-3-carboxylic acid (459 mg) obtained by the method of Example 10, WSC hydrochloride (560 mg) and triethylamine (0.30 mL) were dissolved in 3 mL of DMF and stirred at room temperature for 1 hour. The reaction mixture was added with water and extracted with ethyl acetate, and then the organic layer was washed with 10% aqueous citric acid and saturated aqueous sodium chloride and dried over anhydrous sodium sulfate. The solvent was evaporated under reduced pressure, and the residue was purified by silica gel chromatography (eluent: hexane/ethyl acetate=7/3) to obtain 600 mg of Compound 1-27.

$^1$H-NMR (300 MHz, CDCl$_3$) δ1.40 (t, 3H), 2.50–2.65 (m, 4H), 3. 11 (q, 2H), 3.51 (q, 2H), 4.32 (q, 2H), 5.81 (t, 1H), 6.74 (t, 1H), 7.20–7.64 (m,7H), 7.82–7.91 (m, 2H), 7.88 (dd, 1H), 8.01 (d, 1H), 8.23 (d, 1H), 8.53 (d, 1H), 8.68 (d, 1H)

FAB-MS (m/e) 532 (M+H)$^+$

The compounds of Example 28 to Example 34 were synthesized in the same manner as in Example 27 by using raw materials corresponding to each of the desired compounds instead of the raw materials used in Example 27.

Example 28

Compound 1-28

$^1$H-NMR (300 MHz, CDCl$_3$) δ1.42 (t, 3H), 3.15 (q, 2H), 3.30–3.40 (m, 4H), 3.54 (q, 2H), 4.35 (q, 2H), 5.54 (t, 1H), 6.66 (t, 1H), 7.20–7.60 (m, 7H), 7.86–7.96 (m, 2H), 7.88 (dd, 1H), 8.06 (d, 1H), 8.23 (d, 1H), 8.56 (d, 1H), 8.68 (dd, 1H)

FAB-MS (m/e) 516 (M+H)$^+$

Example 29

Compound 1-29

$^1$H-NMR (300 MHz, CDCl$_3$) δ1.35 (t, 3H), 2.80–2.90 (m, 4H), 3.05–3.15 (m, 2H), 3.56–3.66 (m, 2H), 4.26 (q, 2H), 7.18 (dd, 1H), 7.28 (d, 1H), 7.36 (d, 1H), 7.40–7.56 (m, 6H), 7.84–7.91 (m, 2H), 7.86 (dd, 1H), 7.88 (d, 1H), 8.06 (d, 1H), 8.22 (dd, 1H), 8.63 (d, 1H), 8.68 (dd, 1H)

FAB-MS (m/e) 515 (M+H)$^+$

Example 30

Compound 1-30

$^1$H-NMR (300 MHz, CDCl$_3$) δ1.39 (t, 3H), 2.41 (t, 2H), 2.49 (t, 2H), 2.99 (t, 2H), 3.49 (m, 2H), 4.32 (q, 2H), 6.80 (t, 1H), 7.18 (dd, 1H), 7.32–7.50 (m, 6H), 7.86 (dd, 1H), 7.92–8.00 (m, 2H), 8.16 (d, 1H), 8.24 (d, 1H), 8.60–8.68 (m, 2H)

FAB-MS (m/e) 529 (M+H)$^+$

Example 31

Compound 1-31

$^1$H-NMR (300 MHz, CDCl$_3$) δ1.36 (t, 2H), 1.40–1.60 (m 4H), 2.92 (m, 2H), 3.34 (m, 2H), 4.28 (q, 2H), 5.71 (t, 1H), 6.56 (t, 1H), 7.20 (dd, 1H), 7.27 (d, 1H), 7.30–7.70 (m, 6H), 7.80–7.90 (m, 2H), 8.03 (d, 1H), 8.18 (d, 1H), 8.24 (d, 1H), 8.51 (d, 1H), 8.68 (dd, 1H)

FAB-MS (m/e) 500 (M+H)$^+$

Example 32

Compound 1-32

$^1$H-NMR (300 MHz, CDCl$_3$) δ1.2–1.7 (m, 6H), 1.44 (t, 31), 2.92 (m, 2H), 3.38 (m, 2H), 4.38 (q, 2H), 5.04 (t, 1H), 6.31 (bs, 1H), 7.26 (m, 1H), 7.4–7.7 (m, 6H), 7.91 (m, 2H), 8.03 (d, 1H), 8.18 (d, 1H), 8.25 (d, 1H), 8.56 (d, 1H), 8.66 (dd, 1H)

FAB-MS (m/e) 514 (M+H)$^+$

Example 33

Compound 1-33

$^1$H-NMR (300 MHz, DMSO-d$_6$) δ1.1–1.5 (m, 8H), 1.32 (t, 3H), 2.79 (m, 2H), 3.20 (m, 2H), 4.48 (q, 2H), 7.26 (t, 1H), 7.52 (dd, 1H), 7.60–7.80 (m, 5H), 7.90–8.40 (m, 2H), 8.06–8.18 (m, 2H), 8.18–8.24 (m, 2H), 8.40 (t, 1H), 8.60–8.72 (m, 2H)

FAB-MS (m/e) 528 (M+H)$^+$

Example 34

Compound 1-34

$^1$H-NMR (300 MHz, CDCl$_3$) δ1.22 (d, 3H), 1.24–1.58 (m, 6H), 1.45 (t, 3H), 2.92 (m, 2H), 4.28 (sep. 1H), 4.42 (q, 2H), 5.02 (t, 1H), 5.86 (d, 1H), 7.26 (ddd, 1H), 7.4–7.7 (m, 6H), 7.910–7.96 (m, 2H), 8.03 (d, 1H), 8.18 (d, 1H), 8.26 (d, 1H), 8.58 (d, 1H), 8.68 (dd, 1H)

FAB-MS (m/e) 528 (M+H)$^+$

Example 35

Synthesis of Compound 1-35

6.04 g of trans-4-aminomethylcyclohexanecarboxylic acid was dissolved in 1 N aqueous sodium hydroxide, and the solution was added with 8.71 g of 1-naphthalenesulfonyl chloride and stirred at room temperature for 3 hours. The reaction mixture was made acidic with 4 N hydrochloric acid and diluted with water, and the deposited solid was washed with water. This solid was taken by filtration to obtain 10.1 g of a sulfonamide. The resulting sulfonamide (2.57 g) was dissolved in 20 mL of toluene, and the solution was added with 1.6 mL of diphenyl phosphorylazide and 1.0 mL of triethylamine and stirred at 70° C. for 2 hours. The reaction mixture was concentrated under reduced pressure, and then purified by silica gel column chromatography (methanol/chloroform=1/50) to obtain 1.09 g of an isocyanate.

The resulting isocyanate was dissolved in 40 mL of toluene, added dropwise with 1.5 mL of concentrated hydrochloric acid and then refluxed with heating at 120° C. to 130° C. for 2 hours. The deposited white solid was washed with water, dried, then dissolved in 15 mL of dimethylformamide. The solution was added with 0.76 g of (9-ethylcarbazole)-3-carboxylic acid and WSC hydrochloride and stirred at room temperature for 30 minutes. The reaction mixture was added with water and extracted with ethyl acetate, and the organic layer was washed with water, 0.1 N aqueous sodium hydroxide and saturated brine, and dried over anhydrous sodium sulfate. This organic layer was concentrated, and the resulting residue was purified by silica gel column chromatography (ethyl acetate/hexane=1/2) to obtain 0.31 g of Compound 1-35.

$^1$H-NMR (300 MHz, CDCl$_3$) δ0.8–1.0 (m, 2H), 1.0–1.3 (m, 3H), 1.35 (t, 3H), 1.6–2.0 (m, 4H), 2.70 (m, 2H), 3.83 (m, 1H), 4.27 (q, 2H), 5.48 (bs, 1H), 5.63 (bs, 1H), 7.1–7.7 (m, 8H), 7.8–8.3 (m, 5H), 8.69 (m, 1H)

FAB-MS (m/e) 540 (M+H)$^+$

Example 36

Synthesis of Compound 1-36

Under ice cooling, 7.91 g of 1,5-diaminopentane was added dropwise with 240 mL of acetonitrile solution in which 1.75 g of 1-naphthalenesulfonyl chloride was dissolved, and the mixture was stirred at room temperature for 1 hour. The reaction mixture was evaporated under reduced pressure, and the residue was added with 500 mL of water and extracted with dichloromethane. The organic layer was dried over anhydrous magnesium sulfate, and the solvent was evaporated under reduced pressure to obtain 1.90 g of 5-(1-naphthalenesulfonyl)aminopentylamine.

Synthesis of (9-ethyl-4-methoxycarbazole)-3-carboxylic acid

Under a nitrogen flow, 150 mg of potassium hydride was added with 10 mL of tetrahydrofuran, 240 mg of methyl formate and 9-ethyl-tetrahydrocarbazol-4-one (850 mg) obtained by the method described in Heterocycles, 5, p.585 (1997) and the mixture was refluxed for 5 hours. The reaction mixture was added with water, washed with ethyl acetate, neutralized with hydrochloric acid and then extracted with ethyl acetate. The organic layer was dried over anhydrous magnesium sulfate, and the solvent was evaporated under reduced pressure. Then, the residue was dissolved in 3 mL of toluene, added with 910 mg of DDQ and stirred at room temperature for 10 minutes. Insoluble solids were removed by filtration, and the filtrate was evaporated under reduced pressure. Then, the residue was purified by silica gel chromatography (chloroform) to obtain 518 mg of (9-ethyl-4-hydroxycarbazole)-3-aldehyde.

The resulting (9-ethyl-4-hydroxycarbazole)-3-aldehyde (500 mg) was dissolved in 5 mL of acetone, added with 870 mg of potassium carbonate and 260 mg of methyl iodide, and the mixture was stirred at room temperature for 2 hours. The reaction mixture was added with water and extracted with ethyl acetate, and the organic layer was dried over anhydrous magnesium sulfate. Then, the solvent was evaporated under reduced pressure to obtain 501 mg of (9-ethyl-4-methoxycarbazole)-3-aldehyde.

The resulting (9-ethyl-4-methoxycarbazole)-3-aldehyde (502 mg) was dissolved in 1 mL of acetone, and the solution was added with 600 mg of potassium permanganate and stirred for 2 hours and 30 minutes. Insoluble solids were removed by filtration, and the filtrate was evaporated under reduced pressure. Then, the residue was dissolved in 1 N aqueous sodium hydroxide. The aqueous solution was washed with ethyl acetate, then made acidic with hydrochloric acid and extracted with ethyl acetate. The organic layer was dried over anhydrous magnesium sulfate, and the solvent was evaporated under reduced pressure. The residue was recrystallized from ethyl acetate to obtain 348 mg of (9-ethyl-4-methoxycarbazole)-3-carboxylic acid.

378 mg of the resulting 5-(1-naphthalenesulfonyl) aminopentylamine and 348 mg of (9-ethyl-4-methoxycarbazole)-3-carboxylic acid were dissolved in 3 mL of dimethylformamide, and the solution was added with 247 mg of WSC hydrochloride and stirred at room temperature for 3 hours. Then, the reaction mixture was added with water and extracted with ethyl acetate, and the organic layer was successively washed with water and saturated brine. The solvent was concentrated under reduced pressure, and the resulting residue was purified by silica gel column chromatography (ethyl acetate/hexane=1/2) to obtain 96 mg of Compound 1-36.

$^1$H-NMR (300 MHz, CDCl$_3$) δ1.2–1.6 (m, 6H), 1.44 (t, 3H), 2.92 (m, 2H), 3.38 (m, 2H), 4.02 (s, 3H), 4.35 (q, 2H), 5.24 (bs, 1H), 7.2–7.6 (m, 7H), 7.9–8.3 (m, 6H), 8.67 (m, 1H)

FAB-MS (m/e) 544 (M+H)$^+$

Example 37

Compound 1-37

To 300 mL of water, 11.3 g of 3-hydroxy-4-carboxyphenylhydrazine, 21 g of sodium acetate and 67.7 mL of cyclohexanone were added, and the mixture was heated at 100° C. for 30 minutes. The solid in the reaction mixture was taken by filtration, and washed with water and hexane to obtain 11.8 g of a hydrazone. Then, 200 mL of trifluoroacetic acid was added to the resulting hydrazone (11.8 g). The reaction mixture was refluxed for 8 hours, and poured into water, and the deposited solid was taken by filtration to obtain a 1:1 mixture (7.82 g) of 5-hydroxytetrahydrocarbazole-6-carboxylic acid and 7-hydroxytetrahydrocarbazole-6-carboxylic acid.

Then, the resulting mixture (2.05 g) was dissolved in 60 mL of acetone, added with 3.0 g of potassium hydroxide and 7 mL of methyl iodide, and the mixture was refluxed for 4 hours. The reaction mixture was evaporated under reduced pressure, and the residue was added with water and extracted with ethyl acetate. The organic layer was dried over anhydrous magnesium sulfate, and the solvent was evaporated under reduced pressure. The residue was purified by silica gel column chromatography (ethyl acetate/hexane=12/85 to 25/75) to obtain 1.27 g of 5-ethoxytetrahydrocarbazole-6-carboxylic acid ethyl ester and 0.77 g of 7-ethoxytetrahydrocarbazole-6-carboxylic acid ethyl ester. The resulting 7-ethoxytetrahydrocarbazole-6-carboxylic acid ethyl ester was converted into a carboxylic acid by alkali hydrolysis. Compound 1-37 was obtained in the same manner as in Example 36 except that the 7-ethoxytetrahydrocarazole-6-carboxylic acid obtained was used.

$^1$H-NMR (300 MHz, CDCl$_3$) δ1.2–1.5 (m, 12H), 1.7–2.0 (m, 4H), 2.6–2.7 (m, 4H), 2.90 (m, 2H), 3.33 (m, 2H), 4.00 (q, 2H), 4.19 (q, 2H), 5.08 (t, 1H), 6.71 (s, 1H) 7.5–7.6 (m, 3H), 7.90 (dd, 1H), 8.02 (d, 1H), 8.14 (t, 1H), 8.24 (d, 1H), 8.37 (s, 1H), 8.66

FAB-MS (m/e) 561 M$^+$

Example 38

Compound 1-38

The 7-ethoxytetrahydrocarbazole-6-carboxylic acid obtained in Example 37 was dissolved in 8 mL of toluene, and the solution was added with 2.14 g of chloranil and refluxed for 2 hours and 30 minutes. The reaction mixture was filtered, and the filtrate was concentrated under reduced pressure and purified by silica gel column chromatography (ethyl acetate) to obtain 336 mg of 9-ethyl-5-ethoxycarbazole-6-carboxylic acid. Compound 1-38 was obtained in the same manner as in Example 36 except that the 9-ethyl-5-ethoxycarbazole-6-carboxylic acid obtained was used.

$^1$H-NMR (300 MHz, CDCl$_3$) δ1.2–1.7 (m, 12H), 2.92 (m, 2H), 3.38 (m, 2H), 4.24–4.40(m, 4H), 4.86 (t, 1H), 6.81 (s, 1H), 7.2–7.6 (m, 7H), 7.90 (dd, 1H), 8.02 (d, 1H), 8.14 (t, 1H), 8.24 (dd, 1H), 8.66 (d, 1H)

FAB-MS (m/e) 558 (M+H)$^+$

Example 39

Compound 1-39

Compound 1-39 was obtained in the same manner as in Example 37 except that the 5-ethoxytetrahydrocarbazole-6-carboxylic-acid ethyl ester obtained in Example 37 was used.

$^1$H-NMR(300 MHz, CDCl$_3$) δ1.2–1.7 (m, 6H), 1.42 (t, 3H), 1.55 (t, 3H), 2.92 (m, 2H), 3.38 (m, 2H), 4.22 (q, 2H), 4.37 (q, 2H), 5.07 (bs, 1H), 7.22 (dd, 1H), 7.3–7.7 (m, 6H), 7.92 (dd, 1H1), 8.02–8.16 (m, 3H), 8.25 (dd, 1H), 8.66 (dd, 1H)

FAB-MS (m/e) 558 (M+H)$^+$

Example 40

Compound 1-40

5-Ethoxytetrahydrocarbazole-8-carboxylic acid was obtained in the same manner as in Example 37 except that the 5-ethoxytetrahydrocarbazole-6-carboxylic acid ethyl ester obtained in Example 37 was used, and then Compound 1-40 was obtained in the same manner as in Example 38.

$^1$H-NMR (300 MHz, CDCl$_3$) δ1.2–1.5 (m, 6H), 1.26 (t, 3H), 1.42 (t, 3H), 1.8–2.0 (m, 4H), 2.71 (m, 1H), 2.91 (m, 4H), 3.32 (m, 2H), 4.02 (q, 2H), 4.12 (q, 2H), 5.06 (bs, 1H), 7.09 (d, 1H), 7.5–7.6 (m, 3H), 7.8–8.1 (m, 4H), 8.25 (dd, 1H), 8.67 (dd, 1H)

FAB-MS (m/e) 562 (M+H)$^+$

Example 41

Compound 1-41

Compound 1-36 (63 mg) obtained by the method of Example 36 was dissolved in 2 mL of dichloromethane and cooled to –78° C. To this solution, 1.2 mL of 1.0 M boron tribromide solution in dichloromethane was added dropwise and stirred for 30 minutes. Then, the reaction mixture was added with water and extracted with dichloromethane, and the organic layer was washed with saturated brine. The solvent was concentrated under reduced pressure, and the resulting residue was purified by silica gel column chromatography (ethyl acetate/hexane=1/2) to obtain 30 mg of Compound 1-41.

$^1$H-NMR (300 MHz, CDCl$_3$) δ1.2–1.6 (m, 6H), 1.43 (t, 3H), 2.90 (m, 2H), 3.30 (m, 2H), 4.29 (q, 2H), 4.98 (t, 1H), 6.35 (bs, 1H), 6.79 (d, 1H), 7.2–7.7 (m, 8H), 7.91 (d, 1H), 8.04 (d, 1H), 8.24 (d, 1H), 8.42 (d, 1H), 8.65 (d, 1H)

FAB-MS (m/e) 530 (M+H)$^+$

The compounds of Example 42 to Example 44 were synthesized in the same manner as in Example 41 by using raw materials corresponding to each of the desired compounds instead of the raw materials used in Example 41.

Example 42

Compound 1-42

$^1$H-NMR (300 MHz, CDCl$_3$) δ1.2–1.7 (m, 6H), 1.42 (t, 3H), 2.94 (m, 2H), 3.36 (m, 2H), 4.24 (q, 2H), 4.79 (bs, 1H), 6.55 (bs, 1H), 6.86 (s, 1H), 7.1–7.7 (m, 6H), 7.9–8.1 (m, 2H), 8.11 (s, 1H), 8.26 (dd, 1H), 8.65 (d, 1H)

FAB-MS (m/e) 530 (M+H)$^+$

Example 43

Compound 1-43

$^1$H-NMR (300 MHz, CDCl$_3$) δ1.2–1.7 (m, 6H), 1.42 (t, 3H), 1.80–2.00 (m, 4H), 2.63 (m, 4H), 2.89 (m, 2H), 3.28 (m, 2H), 3.93 (q, 2H), 4.89 (t, 1H), 6.43 (t, 1H), 6.77 (s, 1H), 7.45 (s, 1H), 7.5–7.7 (m, 3H), 7.92 (dd, 1H), 8.05 (d, 1H), 8.25 (dd, 1H), 8.65 (d, 1H)

FAB-MS (m/e) 534 (M+H)$^+$

Example 44

Compound 1-44

$^1$H-NMR (300 MHz, CDCl$_3$) δ1.2–1.7 (m, 9H), 1.7–2.0 (m, 4H), 2.6–2.7 (m, 2H), 2.92 (m, 2H), 2.94–3.02 (m, 2H), 3.28 (m, 2H), 4.02 (q, 2H), 4.75 (br, 1H), 6.10 (br, 1H), 6.68 (d, 1H), 6.98 (d, 1H), 7.4–7.7 (m, 3H), 7.92 (dd, 1H), 8.06 (dd, 1H), 8.28 (dd, 1H), 8.68 (dd, 1H)

FAB-MS (m/e) 534 (M+H)$^+$

Example 45

Synthesis of Compound 1-45

1,2,3,4-Tetrahydrocarbazole-6-carboxylic acid methyl ester (460 mg) prepared by the method described in Journal of Chemical Society, p.809 (1926) was dissolved in 2.5 mL of DMF, and the solution was added with 0.3 mL of ethyl iodide and 120 mg of sodium hydride and stirred at room temperature at 50° C. for 2 hours under a nitrogen flow. Then, the reaction mixture was added with water, neutralized with 2 N hydrochloric acid and extracted with ethyl acetate. The organic layer was washed with water and dried over anhydrous sodium sulfate, and the solvent was evaporated under reduced pressure. The residue was purified by silica gel chromatography (eluent: dichloromethane) to obtain 490 mg of N-ethyl-1,2,3,4-tetrahydrocarbazole-6-carboxylic acid methyl ester.

Then, 480 mg of the N-ethyl-1,2,3,4-tetrahydrocarbazole-6-carboxylic acid methyl ester was dissolved in 5 mL of methanol, added with 4 mL of 4 N aqueous sodium hydroxide, and stirred at room temperature for 2 hours. Subsequently, the reaction mixture was cooled and then neutralized with hydrochloric acid, and the deposited precipitates were collected to obtain 400 mg of N-ethyl-1,2,3,4-tetrahydrocarbazole-6-carboxylic acid. The obtained N-ethyl-1,2,3,4-tetrahydrocarbazole-6-carboxylic acid (73 mg), 6-(1-naphthalenesulfonyl)-aminopentylamine (100 mg) obtained in Example 36 and WSC (68 mg) were dissolved in 2 mL of DMF and the mixture was stirred at room temperature for 4 hours. The reaction mixture was added with water and extracted with ethyl acetate. Then, the organic layer was washed with water and dried over anhydrous sodium sulfate, and the solvent was evaporated under reduced pressure. The residue was purified by silica gel chromatography (eluent: chloroform/ethyl acetate=95/5) to obtain 50 mg of Compound 1-45.

$^1$H-NMR (300 MHz, CDCl$_3$) δ1.2–1.5 (m, 6H), 1.33 (t, 3H), 1.7–2.0 (m, 4H), 2.65–2.57 (m, 4H), 2.91 (m, 2H), 3.31 (m, 2H), 4.09 (q, 2H), 4.88 (t, 1H), 6.11 (t, 1H), 7.2–7.3 (m, 1H), 7.5–7.7 (m, 4H), 7.9–8.0 (m, 2H), 8.08 (dd, 1H), 8.25 (d, 1H), 8.68 (dd, 1H)

FAB-MS (m/e) 518 (M+H)$^+$

The compounds of Example 46 to Example 53 were synthesized in the same manner as in Example 45 by using raw materials corresponding to each of the desired compounds instead of the raw materials used in Example 45.

Example 46

Compound 1-46

$^1$H-NMR (300 MHz, CDCl$_3$) δ1.20–1.34 (tt, 2H), 1.4–1.6 (m, 4H), 2.94 (m, 2H), 3.39 (m, 2H), 3.88 (s, 3H), 4.90 (t, 1H), 6.25 (t, 1H), 7.20–7.35 (m, 1H), 7.38–7.45 (m, 2H), 7.48–7.66 (m, 4H), 7.90–7.96 (m, 2H), 8.06 (dd, 1H), 8.14 (dd, 1H), 8.26 (dd, 1H), 8.55 (d, 1H), 8.67 (dd, 1H)

FAB-MS (m/e) 499 M$^+$

Example 47

Compound 1-47

$^1$H-NMR (300 MHz, CDCl$_3$) δ1.20–1.34 (m, 2H), 1.4–1.6 (m, 4H), 1.70 (d, 6H), 2.92 (m, 2H), 3.39(m, 2H), 4.95 (t, 1H), 5.01 (sep., 1H), 6.26 (t, 1H), 7.20–7.35 (m, 1H), 7.4–7.7 (m, 6H), 7.86–7.96 (m, 2H), 8.04 (d, 1H), 8.15 (d, 1H), 8.26 (dd, 1H), 8.56 (d, 1H), 8.67 (dd, 1H)

FAB-MS (m/e) 528 (M+H)$^+$

Example 48

Compound 1-48

$^1$H-NMR (300 MHz, CDCl$_3$) δ0.95 (t, 3H), 1.2–1.6 (m, 8H), 1.60 (m, 2H), 2.92 (m, 2H), 3.41(m, 2H), 3.80 (t, 2H), 4.91 (t, 1H), 6.24 (t, 1H), 7.20–7.35 (m, 1H), 7.4–7.7 (m, 6H), 7.88–7.96 (m, 2H), 8.05 (d, 1H), 8.14 (d, 1H), 8.26 (dd, 1H), 8.55 (d, 1H), 8.67 (dd, 1H)

FAB-MS (m/e) 542 (M+H)$^+$

Example 49

Compound 1-49

$^1$H-NMR (300 MHz, CDCl$_3$) δ1.20–1.40 (m, 2H), 1.4–1.6 (m, 4H), 2.96 (m, 2H), 3.40 (m, 2H), 3.80 (t, 2H), 4.51 (t, 2H), 5.05 (t, 1H), 6.38 (t, 1H), 7.20–7.30 (m, 1H), 7.45–7.70 (m, 6H), 7.90–8.00 (m, 2H), 8.06 (d, 1H), 8.14 (d, 1H), 8.27 (dd, 1H), 8.58 (d, 1H), 8.69 (dd, 1H)

FAB-MS (m/e) 544 (M+H)$^+$

Example 50

Compound 1-60

$^1$H-NMR (300 MHz, CDCl$_3$) δ1.36 (d, 6H), 1.80–2.00 (m, 4H), 2.70–2.80 (m, 4H), 3.18 (sep. 1H), 3.28 (s, 3H), 3.36 (m, 2H), 3.62 (t, 4H), 3.69 (m, 4H), 4.20 (t, 3H), 4.58 (brs, 1H), 6.58 (brs, 1H), 7.28 (d, 1H), 7.58 (dd, 1H), 7.96 (d, 1H)

FAB-MS (m/e) 465 M$^+$

Example 51

Compound 1-51

$^1$H-NMR (300 MHz, CDCl$_3$) δ1.33 (t, 3H), 1.80–2.00 (m, 4H), 2.70–2.80 (m, 4H), 2.94 (s, 3H), 3.34 (m, 2H), 3.63 (t, 2H), 3.69(m, 4H), 4.09 (q, 2H), 4.91 (brs, 1H), 6.56 (brs, 1H), 7.27 (d, 1H), 7.59 (dd, 1H), 7.97 (d, 1H)

FAB-MS (m/e) 407 M$^+$

Example 52

Compound 1-52

$^1$H-NMR (300 MHz, CDCl$_3$) δ1.35 (d, 6H), 1.80–2.00 (m, 4H), 2.70–2.80 (m, 4H), 3.16 (sep. 1H), 3.33 (m, 2H), 3.63 (t, 4H), 3.69 (m, 4H), 4.08 (q, 2H), 4.58 (t, 1H), 6.64 (brs, 1H), 7.27 (d, 1H), 7.59 (dd, 1H), 7.97 (d, 1H)

FAB-MS (m/e) 435 M$^+$

Example 53

Compound 1-53

$^1$H-NMR (300 MHz, CDCl$_3$) δ1.80–2.00 (m, 4H), 2.70–2.80 (m, 4H), 2.94 (s, 3H), (s, 3H), 3.29 (s, 3H), 3.33 (m, 2H), 3.60–3.74 (m, 8H), 4.20 (t, 2H), 4.92 (brs, 1H), 6.59 (brs, 1H), 7.29 (d, 1H), 7.60 (dd, 1H), 7.96 (d, 1H)

FAB-MS (m/e) 437 M$^+$

Example 54

Synthesis of 3-(1-naphthylsulfonylaminopentylaminocarbonyl) carbazole

Carbazole-3-carboxylic acid methyl ester (450 mg) was dissolved in 7 mL of methanol, and the solution was added with 2.5 mL of 2 N aqueous sodium hydroxide, and stirred at 60° C. for 3 hours. Subsequently, the reaction mixture was cooled and then neutralized with hydrochloric acid, and the deposited precipitates were collected to obtain 410 mg of carbazole-3-carboxylic acid. The resulting carbazole-3-carboxylic acid (205 mg), 6-(1-naphthalenesulfonyl)aminopentylamine (292 mg) obtained in the example and WSC (192 mg) were dissolved in 5 mL of DMF and stirred at room temperature for 3 hours. The reaction mixture was added with water and extracted with ethyl acetate. Then, the organic layer was washed with water and dried over anhydrous sodium sulfate, and the solvent was evaporated under reduced pressure. The residue was purified by silica gel chromatography (eluent: chloroform/methanol=95/5) to obtain 123 mg of the compound, 3-(1-naphthylsulfonylaminopentylaminocarbonyl)carbazole.

$^1$H-NMR (300 MHz, DMSO-d$_6$) δ1.16–1.30 (m, 2H), 1.3–1.48 (m, 4H), 2.79 (m, 2H), 3.15(m, 2H), 7.21 (ddd, 1H), 7.39 (ddd, 1H), 7.46–7.54 (m, 2H), 7.60–7.74 (m, 3H), 7.89 (dd, 1H), 7.94 (t, 1H), 8.06–8.16 (m, 3H), 8.21 (dd, 1H), 8.31 (t, 1H), 8.62 (d, 1H), 8.66 (dd, 1H) 11.54 (s, 1H)

FAB-MS (m/e) 486 (M+H)$^+$

Example 55

Synthesis of Compound 1-54

The 3-(1-naphthylsulfonylaminopentylaminocarbonyl)carbazole (70 mg) obtained by the method of Example 54 was dissolved in a mixture of 0.3 mL of dimethylacetamide and 1.0 mL of acetonitrile, and the solution was added with 0.030 mL of triethylamine and 0.010 mL of acetyl chloride, and stirred at room temperature for 5 hours under a nitrogen flow. The reaction mixture was added with water, extracted with ethyl acetate and dried over anhydrous sodium sulfate, and the solvent was evaporated under reduced pressure. The residue was purified by silica gel chromatography (eluent: dichloromethane/ethyl acetate=9/1) to obtain 56 mg of Compound 1-54.

$^1$H-NMR (300 MHz, CDCl$_3$) δ1.13–1.30 (m, 2H), 1.3–1.48 (m, 4H), 2.06 (s, 3H), 2.84 (m, 2H), 3.73(t, 2H), 4.64 (t, 1H), 7.27–7.36 (m, 1H), 7.44–7.70 (m, 6H), 7.72 (dd, 1H), 7.94 (d, 1H), 8.08 (d, 1H), 8.11 (d, 1H), 8.22 (d, 1H), 8.42–8.48 (m, 2H), 8.63 (dd, 1H)

FAB-MS (m/e) 528 (M+H)$^+$

Example 56

Synthesis of Compound 1-55

Compound 1-32 (256 mg) obtained by the method of Example 32 was dissolved in 2 mL of DMF, added with 112 mg of methyl iodide and 690 mg of potassium carbonate, and stirred at 60° C. for 3 hours. The reaction mixture was added with 10% aqueous citric acid and extracted with dichloromethane. The organic layer was washed with saturated aqueous hydrogencarbonate solution, and dried over anhydrous sodium sulfate. The solvent was evaporated under reduced pressure, and the residue was purified by silica gel chromatography (eluent: dichloromethane/ethyl acetate=9/1) to obtain 169 mg of Compound 1-55.

$^1$H-NMR (300 MHz, CDCl$_3$) δ1.32–1.54 (m, 3H), 1.44 (t, 3H), 1.58–1.70 (m, 4H), 2.85 (s, 3H), 3.25 (t, 2H), 3.46 (m, 2H), 4.37 (q, 2H), 6.52 (t, 1H), 7.26 (dd, 1H), 7.4–7.7 (m, 6H), 7.92 (d,1H), 7.98 (dd, 1H), 8.05 (d, 1H), 8.13–8.24 (m, 2H), 8.62 (d, 1H), 8.74 (d, 1H)

FAB-MS (m/e) 528 (M+H)$^+$

Example 57

Synthesis of Compound 1-56

The N-ethyl-3-(ω-aminopentylaminocarbonyl)-carbazole (162 mg) obtained by the method of Example 10 and phthalic anhydride (74 mg) were dissolved in 3 mL of chloroform and the mixture was stirred under a reflux condition for 5 hours. Then, the solvent was evaporated under reduced pressure, and the residue was left at 100° C. for 5 hours under reduced pressure. The resulting residue was purified by silica gel chromatography (eluent: dichloromethane/ethyl acetate=8/2) to obtain 20 mg of Compound 1-56.

$^1$H-NMR (300 MHz, CDCl$_3$) δ1.4–1.55 (m, 2H), 1.42 (t, 3H), 1.60–1.80 (m, 4H), 3.51 (m, 2H), 3.72 (t, 2H), 4.37 (q, 2H), 6.44 (t, 1H), 7.26 (ddd, 1H), 7.34–7.46 (m, 2H), 7.45 (ddd, 1H), 7.62 (dd, 2H), 7.76 (dd, 2H), 7.91 (dd, 2H), 8.12 (d, 1H), 8.56 (d, 1H)

FAB-MS (m/e) 454 (M+H)$^+$

The compounds of Example 58 to Example 64 were synthesized in the same manner as in Example 45 by using raw materials corresponding to each of the desired compounds instead of the raw materials used in Example 45.

Example 58

Compound 1-57

$^1$H-NMR (300 MHz, CDCl$_3$) δ1.40–1.50 (t+m, 5H), 1.55–1.70 (m, 4H), 3.00–3.10 (m, 2H), 3.47–3.68 (m, 2H), 4.38 (q, 2H), 5.70 (br, 1H), 6.50 (br, 1H), 7.26 (s, 1H), 7.38–7.55 (m, 4H), 7.93 (d, 1H), 8.14 (d, 1H), 8.21 (d, 1H), 8,57–8.63 (m, 1H), 8.75–8.78 (m, 1H), 9.08–9.14 (m, 1H)

FAB-MS (m/e) 465 (M+H)$^+$

Example 59

Compound 1-58

$^1$H-NMR (300 MHz, CDCl$_3$) δ1.85–2.05 (m, 4H), 2.68–2.78 (m, 4H), 3.21 (q, 2H), 3.28 (s, 3H), 3.53–3.67 (m, 8H), 4.18 (t, 2H), 5.80 (br, 1H), 6.67 (br, 1H), 7.25–7.40 (m, 2H), 7.59 (d, 1H), 7.97 (s, 1H), 8.12 (d, 1H), 8.65–8.80 (m, 1H), 9.00–9.20 (m, 1H)

FAB-MS (m/e) 501 (M+H)$^+$

Example 60

Compound 1-59

$^1$H-NMR (300 MHz, CDCl$_3$) δ1.36 (d, 6H), 1.4–1.9 (m, 6H), 1.80–2.00 (m, 4H), 2.70–2.80 (m, 4H), 3.1–3.2 (m, 3H), 3.49 (m, 2H), 3.92 (t, 2H), 4.18 (br, 1H), 4.21 (t, 2H), 6.28 (br, 1H), 7.29 (d, 1H), 7.56 (dd, 1H), 7.94 (d, 1H)

FAB-MS (m/e) 450 (M+H)$^+$

Example 61

Compound 1-60

$^1$H-NMR (300 MHz, CDCl$_3$) δ1.36 (d, 6H), 1.4–1.9 (m, 6H),1.80–2.00 (m, 4H), 2.27–2.80 (m, 4H), 3.05–3.20 (m, 3H), 3.40–3.55 (m, 4H), 3.60 (t, 2H), 3.73 (t, 2H), 4.23 (t, 2H), 4.34 (br, 1H), 6.34 (br, 1H), 7.29 (d, 1H), 7.56 (dd, 1H), 7.93 (d, 1H)

FAB-MS (m/e) 494 (M+H)$^+$

Example 62

Compound 1-61

$^1$H-NMR (300 MHz, CDCl$_3$) δ1.36 (d, 6H), 1.4–1.9 (m, 6H),1.80–2.00 (m, 4H), 2.65–2.80 (m, 4H), 3.1–3.2 (m, 3H), 3.49 (m, 2H), 4.48 (t, 1H), 4.66 (s, 2H), 5.33 (br, 1H), 5.59 (br, 1H), 6.41 (br, 1H), 7.19 (d, 1H), 7.60 (dd, 1H), 7.99 (d, 1H)

FAB-MS (m/e) 463 (M+H)$^+$

Example 63

Compound 1-62

$^1$H-NMR (300 MHz, CDCl$_3$) δ1.8–2.0 (m, 4H), 2.72 (m, 4H), 3.27 (s, 3H), 3.43 (m, 2H), 3.5–3.7 (m, 8H), 4.18 (t, 2H), 6.65 (m, 1H), 6.93 (m, 1H), 7.25 (d, 1H), 7.56 (dd, 1H) 7.94 (d, 1H)

FAB-MS (m/e) 492 (M+H)$^+$

Example 64

Compound 1-63

$^1$H-NMR (300 MHz, CDCl$_3$) δ1.8–2.0 (m, 4H), 2.72 (m, 4H), 3.28 (s, 3H), 3.5–3.8 (m, 10H), 4.21 (t, 2H), 6.52 (m, 1H), 7.18 (m, 1H), 7.29 (d, 1H), 7.57 (dd, 1H), 7.96 (d, 1H)

FAB-MS (m/e) 455 M$^+$

Example 65

Synthesis of Compound 2-1

9-Ethyl-1,2,3,4-tetrahydrocarbazole-6-carboxylic acid (2.30 g) and 1.00 g of 2-(2-aminoethoxy)ethanol were dissolved in 30 mL of dimethylformamide, and the mixture was added with 1.81 g of WSC (hydrochloride), stirred at room temperature for 1.6 hour, and then the reaction was stopped by adding water. The organic layer was extracted with ethyl acetate, washed three times with water and once with saturated brine, and concentrated under reduced pressure. The obtained residue was purified by silica gel column chromatography (methanol/dichloromethane=5/95) to obtain 1.86 g of an alcohol.

Then, 1.55 g of the resulting alcohol was dissolved in 10 mL of pyridine, added with 1.07 g of toluenesulfonyl chloride and stirred at room temperature for 3 hours. The reaction was stopped with water, and the organic layer was extracted with ethyl acetate, washed once with 1 N hydrochloric acid, three times. with water and once with saturated brine, and concentrated under reduced pressure to obtain 1.79 g of a tosylate. 91 mg of the tosylate and 19 mg of 3-mercapto-1,2,4-triazole was dissolved in 3 ml of acetonitrile, and the mixture was added with 0.034 mL of triethylamine and heated at 90–100° C. for 9 hours. After the reaction was stopped with water, the organic layer was extracted with ethyl acetate and purified by preparative TLC (ethyl acetate only) to obtain Compound 2-1 (18 mg).

$^1$H-NMR (300 MHz, CDCl$_3$) δ1.30 (t, 3H), 1.8–2.0 (m, 4H), 2.70 (b, 4H), 3.28 (t, 2H),3.66 (bs, 4H), 3.76 (t, 2H), 4.05 (q, 2H), 6.90 (b, 1H), 7.24 (d, 1H), 7.60 (dd, 1H), 8.00 (s, 1H), 8.04 (d, 1H)

FAB-MS (m/e) 414 (M+1)

The compounds of Example 66 and Example 67 were synthesized in the same manner as in Example 65 by using raw materials corresponding to each of the desired compounds instead of the raw materials used in Example 65.

Example 66

Compound 2-2

$^1$H-NMR (300 MHz, CDCl$_3$) δ1.32 (t, 3H), 1.8–2.1 (m, 4H), 2.20 (m, 2H), 2.7–2.8 (m, 4H), 2.71 (t, 2H), 2.92 (t, 2H), 3.60 (m, 2H), 4.08 (q, 2H), 4.16 (t, 2H), 6.63 (t, 1H), 6.96 (s, 1H), 7.06 (s, 1H), 7.26 (d, 1H), 7.56 (s, 1H), 7.57 (dd, 1H), 7.95 (d, 1H)

FAB-MS (m/e) 397 (M+1)

Example 67

Compound 2-3

$^1$H-NMR (300 MHz, CDCl$_3$) δ1.31 (t, 3H), 1.8–2.0 (m, 4H), 2.70 (m, 4H), 3.12 (t, 2H), 3.70 (m, 6H), 4.07 (q, 2H), 6.85 (m, 1H), 7.02 (s, 2H), 7.24 (d, 1H), 7.60 (dd, 1H), 7.99 (d, 1H)

FAB-MS (m/e) 412 (M)

Example 68

Synthesis of Compound 2-4 and Compound 2-5

Compound 2-4 and Compound 2-5 were obtained in a manner similar to that of Example 65 by using 5-amino-1H-tetrazole instead of 3-mercapto-1,2,4-triazole. Compound 2-4 and Compound 2-5 were separated and purified by preparative TLC (ethyl acetate).

Compound 2-4

$^1$H-NMR (300 MHz, CDCl$_3$) δ1.33 (t, 3H), 1.7–2.0 (m, 4H), 2.72 (m, 4H), 3.67 (m, 4H), 3.83 (t, 2H), 4.10 (q, 2H), 4.31 (t, 2H), 5.22 (bs, 1H), 6.56 (t, 1H), 7.26 (d, 1H), 7.53 (dd, 1H), 7.94 (d, 1H)

FAB-MS (m/e) 398 (M+1)

Compound 2-5

$^1$H-NMR (300 MHz, CDCl$_3$) δ1.33 (t, 3H), 1.7–2.0 (m, 4H), 2.72 (m, 4H), 3.65 (m, 4H), 3.97 (t, 2H), 4.0–4.2 (m, 4H), 4.61 (t, 1H), 6.70 (t, 1H), 7.28 (d, 1H), 7.56 (dd, 1H), 7.99 (d, 1H)

FAB-MS (m/e) 398 (M+1)

Example 69

Synthesis of Compound 2-6

1.27 g of the tosylate obtained in Example 65 was dissolved in 8 mL of dimethylformamide, and the solution was added with 0.51 g of sodium azide and allowed to react over an oil bath at 100° C. for 1.5 hours. The reaction was stopped by adding water to the reaction mixture, and the reaction mixture was extracted with ethyl acetate. The organic layer was washed twice with water and once with saturated brine and then concentrated under reduce pressure to obtain an azide. This azide compound was dissolved in 15 mL of ethanol, added with 150 mg of 10% palladium/activated carbon, and after substitution of hydrogen for the atmosphere in the reaction vessel (ordinary pressure), stirred at room temperature for 5 hours. The reaction solution was filtered, and the filtrate was concentrated under reduced pressure. The resulting residue was purified by silica gel column chromatography (methanol/dichloromethane=15/85) to obtain 0.56 g of amine.

In an amount of 140 mg of the resulting amine was dissolved in 5 ml of acetonitrile, and the solution was added with 117 mg of potassium carbonate and 0.08 mL of diethyl chlorophosphate, and stirred at room temperature for 5 hours. The reaction was stopped by adding water to the reaction mixture, and then the reaction mixture was extracted with ethyl acetate. The organic layer was washed with saturated brine and then concentrated under reduced pressure, and the resulting residue was purified by preparative TLC (methanol/chloroform=1/9) to obtain Compound 2-6 (79 mg).

$^1$H-NMR (300 MHz, CDCl$_3$) δ1.2–1.4 (m, 9H), 1.8–2.0 (m, 4H), 2.70 (m, 4H), 3.0–3.2 (m, 3H), 3.55 (t, 2H), 3.68 (b, 4H), 4.0–4.2 (m, 6H), 6.65 (m, 1H), 7.25 (d, 1H), 7.58 (dd, 1H), 7.98 (d, 1H)

FAB-MS (m/e) 466 (M)

Example 70

Synthesis of N-isopropyl-6-nitro 1,2,3,4-tetrahydrocarbazole

6-Nitro-1,2,3,4-tetrahydrocarbazole (5.04 g) prepared by the method described in Journal of Chemical Society, p.833 (1924) was dissolved in 50 mL of acetone, and the solution was added with 2.25 g of potassium hydroxide and 8.45 g of isopropyl iodide, warmed to 50° C., and stirred for 3 hours. Water was added to the reaction mixture, and the deposited precipitates were collected to obtain 2.60 g of N-isopropyl-6-nitro-1,2,3,4-tetrahydrocarbazole.

Example 71

Synthesis of N-isopropyl-6-amino-1,2,3,4-tetrahydrocarbazole

The N-isopropyl-6-nitro-1,2,3,4-tetrahydrocarbazole (2.60 g) was dissolved in 100 mL of acetic acid, and the solution was added with 2.75 g of iron powder, warmed to 50° C. and stirred for 3 hours. The reaction mixture was filtered, and the filtrate was diluted by addition of water. The reaction mixture was made basic with 1 N sodium hydroxide solution, and extracted with dichloromethane. The organic layer was dried over anhydrous sodium sulfate, and then the solvent was evaporated under reduced pressure. The residue was purified by silica gel chromatography (eluent:

dichloromethane/ethyl acetate=7/3) to obtain 1.35 g of N-isopropyl-6-amino-1,2,3,4-tetrahydrocarbazole.

Example 72

Synthesis of N-isopropyl-6-phenoxycarbonylamino-1,2,3,4-tetrahydrocarbazole

The N-isopropyl-6-amino-1,2,3,4-tetrahydrocarbazole (9.84 g) and 5.05 g of triethylamine were dissolved in 100 mL of dichloromethane, and added dropwise with 7.85 g of phenyl chloroformate. The reaction mixture was stirred at room temperature for 3 hours, then washed with 10% aqueous citric acid and then with saturated aqueous sodium hydrogencarbonate, and dried over anhydrous sodium sulfate. After the solvent was evaporated under reduced pressure, the residue was purified by silica gel chromatography (eluent: hexane/ethyl acetate=8/2) and recrystallized from a mixture of hexane and ethyl acetate, to obtain 2.27 g of N-isopropyl-6-phenoxycarbonylamino-1,2,3,4-tetrahydrocarbazole.

Example 73

Synthesis of Compound 4-1

The N-isopropyl-6-phenoxycarbonylamino-1,2,3,4-tetrahydrocarbazole (88 mg) was dissolved in 3 mL of a mixture of dichloromethane and acetonitrile (1/1), and the solution was added with 40% solution of methylamine (96 mg) in methanol, and stirred under a reflux condition for 8 hours. The reaction mixture was left standing at room temperature, and the deposited crystals were collected and washed with acetonitrile to obtain 63 mg of Compound 4-1.

$^1$H-NMR (300 MHz, CDCl$_3$) δ1.60 (d, 6H), 1.8–2.0 (m, 4H), 2.68–2.82 (m+d, 7H), 4.62 (sep. 1H), 6.10 (br, 1H), 6.96 (dd, 1H), 7.34 (d, 1H), 7.41 (d, 1H)

FAB-MS (m/e) 285 (M)$^+$

Example 74

Synthesis of Compound 4-2

The N-Isopropyl-6-phenoxycarbonylamino-1,2,3,4-tetrahydrocarbazole (88 mg) was dissolved in dichloromethane, and the solution was added with 31 mg of hydroxyethylamine, and stirred under a reflux condition for 8 hours. The reaction mixture was left stand at room temperature, and the deposited crystals were collected and washed with acetonitrile to obtain 35 mg of Compound 4-2.

$^1$H-NMR (300 MHz, CDCl$_3$) δ1.60 (d, 6H), 1.8–2.0 (m, 4H), 2.66–2.82 (m, 4H), 3.38 (m, 2H), 3.71 (t, 2H), 4.62 (sep. 1H), 5.12 (t, 1H), 6.28 (br, 1H), 6.96 (dd, 1H), 7.36 (d, 1H), 7.41 (d, 1H)

FAB-MS (m/e) 315 (M)$^+$

Example 75

Synthesis of Compound 4-3

Compound 4-3 was synthesized in a manner similar to that of Example 74 except that hydroxybutylamine was used instead of the hydroxyethylamine mentioned in the description of Example 74.

$^1$H-NMR (300 MHz, CDCl$_3$) δ1.50–1.80 (m+d, 10H), 1.8–2.0 (m, 4H), 2.66–2.82 (m, 4H), 3.26 (m, 2H), 3.66 (m, 2H), 4.62 (sep. 1H), 6.15 (br, 1H), 6.96 (dd, 1H), 7.32 (d, 1H), 7.41 (d, 1H)

FAB-MS (m/e) 343 (M)$^+$

Example 76

Synthesis of Compound 4-4

Compound 4-4 was synthesized in a manner similar to that of Example 74 except that 4-aminobutyronitrile was used instead of the hydroxyethylamine mentioned in the description of Example 74.

$^1$H-NMR (300 MHz, CDCl$_3$) δ1.59 (d, 6H), 1.6–2.0 (m, 6H), 2.37 (t, 2H), 2.7–2.8 (m, 4H), 3.31 (t, 2H), 4.61 (m, 1H), 6.92 (dd, 1H), 7.30 (d, 1H), 7.42 (d, 1H)

FAB-MS (m/e) 338 (M)$^+$

Example 77

Synthesis of Compound 4-5

Compound 4-5 was synthesized in a manner similar to that of Example 74 except that hydroxyethoxyethylamine was used instead of the hydroxyethylamine mentioned in the description of Example 74.

$^1$H-NMR (300 MHz, CDCl$_3$) δ1.57 (d, 6H), 1.8–2.0 (m, 4H), 2.6–2.8 (m, 4H), 3.42 (t, 2H), 3.54 (m, 4H), 3.66 (m, 2H), 4.59 (m, 1H), 6.95 (dd, 1H), 7.33 (d, 1H), 7.38 (d, 1H)

FAB-MS (m/e) 359 (M)$^+$

Example 78

Synthesis of Compound 4-6

Compound 4-6 was synthesized in a manner similar to that of Example 74 except that isopropylsulfonylbutylamine was used instead of the hydroxyethylamine mentioned in the description of Example 74.

$^1$H-NMR (300 MHz, CDCl$_3$) δ1.60 (d, 6H), 1.52–1.68 (m+d, 10H), 1.8–2.0 (m, 4H), 2.66–2.82 (m, 4H), 3.10–3.26 (m, 4H), 4.56 (t, 1H), 4.62 (sep., 1H), 4.75 (br, 1H), 6.15 (br, 1H), 6.96 (dd, 1H), 7.32 (d, 1H), 7.41 (d, 1H)

FAB-MS (m/e) 448 (M)$^+$

Example 79

Synthesis of Compound 4-7

Compound 4-7 was synthesized in a manner similar to that of Example 74 except that 2-picolylamine was used instead of the hydroxyethylamine mentioned in the description of Example 74.

$^1$H-NMR (300 MHz, CDCl$_3$) δ1.57 (d, 6H), 1.8–2.0 (m, 4H), 2.64–2.78 (m, 4H), 4.50–4.62 (m, 3H), 5.93 (br, 1H), 6.61 (br, 1H), 6.98 (dd, 1H), 7.17 (ddd, 1H), 7.32–7.40 (m, 3H), 7.67 (ddd, 1H), 8.46 (dd, 1H)

FAB-MS (m/e) 363 (M+H)$^+$

Example 80

Synthesis of Compound 4-8

Compound 4-8 was synthesized in a manner similar to that of Example 74 except that 3-picolylamine was used instead of the hydroxyethylamine mentioned in the description of Example 74.

$^1$H-NMR (300 MHz, CDCl$_3$) δ1.57 (d, 6H), 1.8–2.0 (m, 4H), 2.64–2.78 (m, 4H), 4.42 (d, 2H), 4.56 (sep., 1H), 5.09 (t, 1H), 6.25 (br, 1H), 6.94 (dd, 1H), 7.20–7.26 (m, 1H), 7.32 (d, 1H), 7.38 (d, 1H), 7.65–7.68 (m, 1H), 8.4–68.49 (m, 2H)

FAB-MS (m/e) 363 (M+H)$^+$

Example 81

Synthesis of Compound 4-9

Compound 4-9 was synthesized in a manner similar to that of Example 74 except that 4-picolylamine was used instead of the hydroxyethylamine mentioned in the description of Example 74.

$^1$H-NMR (300 MHz, CDCl$_3$) δ1.57 (d, 6H), 1.8–2.0 (m, 4H), 2.64–2.78 (m, 4H), 4.43 (d, 2H), 4.56 (sep., 1H), 5.24 (t, 1H), 6.41 (br, 1H), 6.98 (dd, 1H), 7.24 (d, 2H), 7.36 (d, 1H), 7.39 (d, 1H), 8.50 (d, 2H)

FAB-MS (m/e) 363 (M+H)$^+$

Example 82

Synthesis of Compound 4-10

Compound 4-10 was synthesized in a manner similar to that of Example 74 except that imidazolylmethylamine was used instead of the hydroxyethylamine mentioned in the description of Example 74.

$^1$H-NMR (300 MHz, CDCl$_3$) δ1.57 (d, 6H), 1.8–2.1 (m, 6H), 2.65 (m, 2H), 2.73 (m, 2H), 3.19 (dq, 2H), 4.00 (t, 2H), 4.58 (m, 1H), 5.02 (m, 1H), 6.46 (bs, 1H), 6.92 (s, 1H), 6.93 (dd, 1H), 7.03 (s, 1H), 7.34 (d, 1H), 7.36 (d, 1H), 7.63 (s, 1H)

FAB-MS (m/e) 379 (M)$^+$

Example 83

Synthesis of Compound 5-1

The N-isopropyl-6-amino-1,2,3,4-tetrahydrocarbazole (228 mg) obtained in Example 71, 161 mg of dimethylaminocarbonyl chloride and 152 mg of triethylamine were dissolved in 2 mL of dichloromethane, and the mixture was stirred overnight at room temperature. The reaction mixture was concentrated under reduced pressure, and then added with ethyl acetate, and the organic layer was washed with 10% aqueous citric acid and then with saturated aqueous sodium hydrogencarbonate and dried over anhydrous sodium sulfate. The solvent was evaporated under reduced pressure, and the residue was purified by silica gel chromatography (eluent: dichloromethane/ethyl acetate=8/2) and recrystallized from a mixed solution of dichloromethane and hexane to obtain 78 mg of Compound 5-1.

$^1$H-NMR (300 MHz, CDCl$_3$) δ1.57 (d, 6H), 1.80–2.00 (m, 4H), 2.64–2.74 (m, 4H), 3.04 (s, 6H), 4.56 (sep., 1H), 6.25 (br, 1H), 7.02 (dd, 1H), 7.31 (d, 2H), 7.46 (d, 1H)

FAB-MS (m/e) 299 (M)$^+$

Example 84

Synthesis of Compound 5-2

Synthesis was performed in a manner similar to that of Example 74 except that N-methylisopropylamine was used instead of the hydroxyethylamine mentioned in the description of Example 74.

$^1$H-NMR (300 MHz, CDCl$_3$) δ1.18 (d, 6H) 1.54 (d, 6H), 1.80–2.00 (m, 4H), 2.60–2.80 (m, 4H), 2.86 (s, 3H), 4.46–4.68 (m, 2H), 6.40 (br, 1H), 7.02 (dd, 1H), 7.30 (d, 2H), 7.46 (d, 1H)

FAB-MS (m/e) 327 (M)$^+$

Example 85

Synthesis of Compound 5-3

Synthesis was performed in a manner similar to that of Example 74 except that N-methylbutylamine was used instead of the hydroxyethylamine mentioned in the description of Example 74.

$^1$H-NMR (300 MHz, CDCl$_3$) δ0.94 (t, 3H), 1.25–1.45 (m, 2H), 1.57–1.70 (m+d, 8H), 1.80–2.00 (m, 4H), 2.60–2.80(m, 4H), 3.01 (s, 3H), 3.38 (t, 2H), 4.55 (sep., 1H), 628 (br, 1H), 7.02 (dd, 1H), 7.32 (d, 2H), 7.48 (d, 1H)

FAB-MS (m/e) 341 (M)$^+$

Example 86

Synthesis of Compound 5-4

Synthesis was performed in a manner similar to that of Example 74 except that N-methylhydroxyethylamine was used instead of the hydroxyethylamine mentioned in the description of Example 74.

$^1$H-NMR (300 MHz, CDCl$_3$) δ1.52 (d, 6H), 1.80–2.00 (m, 4H), 2.60–2.75 (m, 4H), 3.04 (s, 3H), 3.50 (t, 2H), 3.80 (t, 2H), 4.55 (sep., 1H), 7.02 (dd, 1H), 7.10 (br, 1H), 7.31 (d, 2H), 7.44 (d, 1H)

FAB-MS (m/e) 329 (M)$^+$

Example 87

Synthesis of Compound 5-5

Synthesis was performed in a manner similar to that of Example 74 except that N,N,N'-trimethylethylenediamine was used instead of the hydroxyethylamine mentioned in the description of Example 74.

$^1$H-NMR (300 MHz, CDCl$_3$) δ1.54 (d, 6H), 1.65–1.90 (m, 6H), 2.28 (S, 6H), 2.39 (t, 2H), 2.60–2.75 (m, 4H), 2.91 (s, 3H), 3.39 (t, 2H), 4.52 (sep, 1H), 7.01 (dd, 1H), 7.27 (d, 1H), 7.57 (d, 1H), 9.36 (br, 1H)

FAB-MS (m/e) 370 (M)$^+$

Example 88

Synthesis of Compound 5-6

Synthesis was performed in a manner similar to that of Example 74 except that 4-methylaminobutanol was used instead of the hydroxyethylamine mentioned in the description of Example 74.

$^1$H-NMR (300 MHz, CDCl$_3$) δ1.55 (d, 6H), 1.60–2.00 (m, 8H), 2.60–2.80 (m, 4H), 3.00 (s, 3H), 3.41 (t, 2H), 3.70 (t, 2H), 4.54 (sep, 1H), 6.50 (br, 1H), 7.03 (dd, 1H), 7.30(d, 1H), 7.46 (d, 1H)

FAB-MS (m/e) 358 (M+H)$^+$

Example 89

Synthesis of Compound 5-7

4-Amino-1-butanol (8.0 g) was dissolved in 150 mL of methanol, and the solution was cooled over ice and slowly added with 39 g of di-t-butyl dicarbonate. The reaction mixture was stirred at room temperature for 1 hour and concentrated, and starting point components were removed by silica gel column chromatography (MeOH:CHCl$_3$=1:20). The resulting Boc compound (9.0 g) was placed in a 500-mL three-neck flask, and after nitrogen substitution, the compound was added with 100 mL of anhydrous tetrahydrofuran and 4.4 g of lithium aluminum hydride and the mixture was stirred for 9.5 hours over an oil bath at 60° C. After the reaction mixture was cooled with ice, the reaction was stopped with methanol and solids were removed by filtration, and then the filtrate was concentrated. The residue was further added with methanol (100 mL), cooled with ice, and slowly added with 9.8 g di-t-butyl dicarbonate. The reaction mixture was stirred for 5 hours at room temperature. The mixture was concentrated and added with water to remove insoluble solids by filtration, and then the organic layer was extracted with ethyl acetate. The organic layer was washed once with water and once with saturated brine and concentrated under reduced pressure. The residue was purified by silica gel column chromatography (methanol:chloroform) to obtain 4.25 g of N-Boc-N-methylaminobutanol.

The resulting N-Boc-N-methyl amino butanol (4.00 g) was placed in a 200-mL threeneck flask, and after nitrogen substitution, the compound was dissolved in 35 mL of anhydrous tetrahydrofuran. The solution was added with 60% sodium hydride (1.77 g), and stirred at room temperature for 30 minutes. Then, the reaction mixture was added dropwise with 1.87 mL of methyl iodide and stirred on an oil bath at 50° C. for 1.5 hours. The reaction was stopped with water, and the organic layer was extracted with ethyl acetate, washed once with water and once with saturated brine, and concentrated under reduced pressure. The residue was purified by silica gel column chromatography (ethyl acetate/hexane=1/4) to obtain 4.25 g of N-Boc-N-methyl-N-methoxybutylamine.

Then, the resulting methoxy compound (956 mg) was dissolved in 10 mL of dioxane, and the solution was added with 20 mL of 4 N hydrochloric acid solution in dioxane, and stirred at room temperature for 2 hours. The reaction mixture was neutralized with triethylamine, filtered and concentrated under reduced pressure. The residue was dissolved in 20 mL of chloroform solution, added with the N-isopropyl-6-phenoxycarbonylamino-1,2,3,4-tetrahydrocarbazole (95 mg) obtained in Example 72 and refluxed with heating for 1 hour. The solvent was evaporated, and the residue was purified by silica gel column chromatography (ethyl acetate/hexane=4/6) to obtain 202 mg of Compound 5-7.

$^1$H-NMR (300 MHz, CDCl$_3$) δ1.55 (d, 6H), 1.6–2.0 (m, 8H), 2.6–2.8 (m, 4H), 3.00 (s, 3H), 3.36 (s, 3H), 3.40 (t, 2H), 3.47 (t, 2H), 4.54 (m, 1H), 6.63 (bs, 1H), 7.04 (dd, 1H), 7.30 (d, 1H), 7.45 (d, 1H)

MS (m/e) 371 (M) FAB-MS (m/e) 370 (M)$^+$

Example 90

Synthesis of Compound 5-8

Compound 5-6 (195 mg) synthesized in Example 88 was dissolved in 5 mL of pyridine, and the solution was added with 50.6 μl of methanesulfonyl chloride and stirred at room temperature for 20 minutes. The reaction was stopped with water, and the reaction mixture was extracted with ethyl acetate. The organic layer was washed twice with 1 N hydrochloric acid, once with water and once with saturated brine, and concentrated under reduced pressure.

The residue was dissolved in 5 mL of dimethylformamide without purification, and the solution was added with 106 mg of sodium azide and heated on an oil bath at 90° C. for 30 minutes. The reaction was stopped by addition of water and the reaction mixture was extracted with ethyl acetate. Then, the organic layer was washed three times with water and once with saturated brine, and concentrated under reduced pressure. The residue was purified by silica gel column chromatography (chloroform) to obtain an azide (205 mg). The obtained azide (205 mg) was dissolved in 6 mL of ethanol and added with 40 mg of 10% palladium carbon to perform hydrogen substitution (ordinary pressure). After the reaction mixture was stirred for 2.5 hour at room temperature, insoluble solids were removed by filtration and the solvent of the filtrate was evaporated. The residue was purified by silica gel column chromatography (methanol/chloroform=1/9 to 15/85) to obtain 138 mg of Compound 5-8.

$^1$H-NMR (300 MHz, CDCl$_3$) δ1.3–1.6 (m, 4H), 1.52 (d, 6H), 1.8–2.0 (m, 4H), 2.43 (m, 2H), 2.6–2.7 (m, 4H), 2.93 (s, 3H), 3.24 (t, 2H), 4.53 (m, 1H), 6.80 (br, 1H), 7.05 (dd, 1H), 7.32 (d, 1H), 7.41 (d, 1H), 8.01 (b, 2H)

FAB-MS (m/e) 357 (M+H) FAB-MS (m/e) 370 (M)$^+$

Example 91

Synthesis of Compound 5-9

Synthesis was performed in a manner similar to that of Example 74 except that 3-methylaminopropionitrile was used instead of the hydroxyethylamine mentioned in the description of Example 74.

$^1$H-NMR (300 MHz, CDCl$_3$) δ1.55 (d, 6H), 1.80–2.00 (m, 4H), 2.65–2.80 (m, 6H), 3.20 (s, 3H), 3.71 (t, 2H), 4.58 (sep., 1H), 6.39 (br, 1H), 7.02 (dd, 1H), 7.32 (d, 2H), 7.44 (d, 1H)

FAB-MS (m/e) 338 (M)$^+$

Example 92

Synthesis of Compound 5-10

2-(2-Aminoethoxy)ethanol (4.19 g) was dissolved in 10 mL of toluene and the solution was added with 2.84 mL of benzyloxycarbonyl chloride. After the reaction mixture was stirred at room temperature for 1 hour, the solvent was evaporated under reduced pressured and the residue was diluted with water. The diluted reaction mixture was extracted with ethyl acetate, and the organic layer was washed with water and saturated brine and concentrated under reduced pressure. The residue was purified by silica gel column chromatography (methanol/chloroform=1/20) to obtain 2.61 g of benzyloxycarbonylamino compound.

Then, the resulting benzyloxycarbonylamino compound (0.96 g) was placed in a 200-mL three-neck flask, and after nitrogen substitution, the compound was dissolved in 4 mL of anhydrous tetrahydrofuran. The solution was cooled with ice, and then slowly added with 310 mg of lithium aluminum hydride. The mixture was then heated to 60° C. and stirred for 30 minutes. After the reaction was stopped with methanol and solids were removed by filtration, the reaction mixture was dried over anhydrous magnesium sulfate and concentrated under reduced pressure. The residue without purification was dissolved in 10 mL of chloroform, and the solution was added with the N-isopropyl-6-phenoxycarbonylamino-1,2,3,4-tetrahydrocarbazole (150 mg) obtained in Example 3, and refluxed with heating for 12 hours. The reaction mixture was concentrated under reduced pressure and the residue was purified by silica gel column chromatography (methanol/chloroform=1/99 to 2/99) and then by silica gel thin layer chromatography (methanol/chloroform=5/95) to obtain 132 mg of Compound 5-10.

$^1$H-NMR (300 MHz, CDCl$_3$) δ1.57 (d, 6H), 1.8–2.0 (m, 4H), 2.6–2.8 (m, 4H), 3.03 (s,3H), 3.59 (t, 2H), 3.72 (m, 4H), 3.83 (m, 2H), 4.57 (m, 1H), 7.03 (dd, 1H), 7.32 (d, 1H), 7.48 (d, 1H)

FAB-MS (m/e) 373 (M)$^+$

Example 93

Synthesis of Compound 5-11

Synthesis was performed in a manner similar to that of Example 92 except that cyclohexylamine was used instead of the 2-(2-aminoethoxy)ethanol mentioned in the description of Example 92.

¹H-NMR (300 MHz, CDCl₃) δ1.55 (d, 6H), 1.3–2.0 (m, 14H), 2.6–2.7 (m, 4H), 2.88 (s,3H), 4.15 (m, 1H), 4.56 (m, 1H), 6.24 (bs, 1H), 7.01 (dd, 1H), 7.30 (d, 1H), 7.52 (d, 1H)

MS (m/e) 367 (M)⁺

Example 94

Synthesis of Compound 5-12

Synthesis was performed in a manner similar to that of Example 92 except that trans-4-aminocyclohexanol was used instead of the 2-(2-aminoethoxy)ethanol mentioned in the description of Example 92.

¹H-NMR (300 MHz, CDCl₃) δ1.55 (d, 6H), 1.4–2.1 (m, 12H), 2.6–2.7 (m, 4H), 2.86 (s,3H), 3.59 (m, 1H), 4.24 (m, 1H), 4.55 (m, 1H), 6.24 (bs, 1H), 7.01 (dd, 1H), 7.30 (d, 1H), 7.50 (d, 1H)

MS (m/e) 383 (M)⁺

Example 95

Synthesis of Compound 5-13

Synthesis was performed in a manner similar to that of Example 74 except that N-methyltetrahydrofurfurylamine was used instead of the hydroxyethylamine mentioned in the description of Example 74.

¹H-NMR (300 MHz, CDCl₃) δ1.54–2.0 (m+d, 10H), 2.65–2.80 (m, 4H), 3.03 (s, 3H), 3.30 (dd, 1H), 3.61 (dd, 1H), 3.82–3.90 (m, 1H), 3.92–4.01 (m, 1H), 4.08–4.16 (m, 1H), 4.52 (sep., 1H), 6.98 (dd; 1H), 7.28 (d, 1H), 7.50 (d, 1H), 8.05 (brs, 1H)

FAB-MS (m/e) 369 (M)⁺

Example 96

Synthesis of Compound 5-14

Synthesis was performed in a manner similar to that of Example 74 except that (2-piperidinoethyl)-N-methylamine obtained by the method described in Tetrahedron, 48, p.1999 (1992) was used instead of the hydroxyethylamine mentioned in the description of Example 74.

¹H-NMR (300 MHz, CDCl₃) δ1.40–1.54 (m, 2H), 1.55 (d, 6H), 1.56–1.70 (m, 4H), 1.78–2.00 (m, 4H), 2.45–2.60 (m, 6H), 2.60–2.80 (m, 4H), 2.98 (s, 3H), 3.39 (t, 2H), 4.54 (sep, 1H), 7.09 (dd, 1H), 7.30 (d, 1H), 7.44 (d, 1H), 9.48 (brs, 1H)

FAB-MS (m/e) 397 (M+H)⁺

Example 97

Synthesis of Compound 5-15

Synthesis was performed in a manner similar to that of Example 74 except that (2-(4-N-methylpiperazino)ethyl)-N-methylamine obtained by the method described in Tetrahedron, 48, p.1999 (1992) was used instead of the hydroxyethylamine mentioned in the description of Example 74.

¹H-NMR (300 MHz, CDCl₃) δ1.55 (d, 6H), 1.75–1.95 (m, 4H), 2.31 (S, 3H), 2.40–2.80 (m, 14H), 2.98 (s, 3H), 3.41 (t, 2H), 4.54 (sep., 1H), 7.12 (dd, 1H), 7.31 (d, 1H), 7.43 (d, 1H), 8.98 (br, 1H)

FAB-MS (m/e) 412 (M+H)⁺

Example 98

Synthesis of Compound 5-16

Synthesis was performed in a manner similar to that of Example 74 except that (2-morpholinoethyl)-N-methylamine obtained by the method described in Tetrahedron, 48, p.1999 (1992) was used instead of the hydroxyethylamine mentioned in the description of Example 74.

¹H-NMR (300 MHz, CDCl₃) δ1.55 (d, 6H), 1.75–1.95 (m, 4H), 2.55–2.80 (m, 10H), 2.99 (s, 3H), 3.43 (t, 2H), 3.70–3.80 (m, 4H), 4.54 (sep., 1H), 7.06 (dd, 1H), 7.31 (d, 1H), 7.45 (d, 1H), 8.72 (brs, 1H)

FAB-MS (m/e) 399 (M+H)⁺

Example 99

Synthesis of Compound 5-17

Synthesis was performed in a manner similar to that of Example 92 except that 2-aminomethylpyridine was used instead of the 2-(2-aminoethoxy)ethanol mentioned in the description of Example 92.

¹H-NMR (300 MHz, CDCl₃) δ1.56 (d, 6H), 1.8–2.0 (m, 4H), 2.6–2.8 (m, 4H), 3.04 (s,3H), 4.56 (m, 1H), 4.64 (s, 2H), 6.36 (bs, 1H), 7.03 (dd, 1H), 7.24 (d, 1H), 7.32 (d, 1H), 7.46 (d, 1H), 8.58 (d, 2H)

FAB-MS (m/e) 376 (M)⁺

Example 100

Synthesis of Compound 5-18

Synthesis was performed in a manner similar to that of Example 74 except that 2-(2-methylaminoethyl)-pyridine was used instead of the hydroxyethylamine mentioned in the description of Example 74.

¹H-NMR (300 MHz, CDCl₃) δ1.55 (d, 6H), 1.75–2.00 (m, 4H), 2.60–2.80 (m, 4H), 2.98 (S, 3H), 3.15 (t, 2H), 3.86 (t, 2H), 4.54 (sep, 1H), 7.05 (dd, 1H), 7.18 (ddd, 1H), 7.23 (d, 1H), 7.30 (d, 1H), 7.47 (d, 1H), 7.63 (td, 1H), 7.80 (brs, 1H), 8.62 (dd, 1H)

FAB-MS (m/e) 391 (M+H)⁺

Example 101

Synthesis of Compound 5-19

Synthesis was performed in a manner similar to that of Example 74 except that 3-(2-methylaminoethyl)-pyridine obtained by the method described in Journal of Heterocycle Chemistry, 27, p.147 (1990) was used instead of the hydroxyethylamine mentioned in the description of Example 74.

¹H-NMR (300 MHz, CDCl₃) δ1.54 (d, 6H), 1.78–1.98 (m, 4H), 2.65–2.75 (m, 4H), 2.86 (t, 2H), 2.94 (s, 3H), 3.60 (t, 3H), 4.56 (sep, 1H), 6.40 (br, 1H), 6.98 (dd, 1H), 7.15–7.30 (m, 3H), 7.48 (d, 1H), 7.66 (ddd, 1H), 7.788 (brs, 1H), 8.64 (dd, 1H)

FAB-MS (m/e) 391 (M+H)⁺

Example 102

Synthesis of Compound 5-20

Synthesis was performed in a manner similar to that of Example 74 except that 4-(2-methylaminoethyl)-pyridine was used instead of the hydroxyethylamine mentioned in the description of Example 74.

¹H-NMR (300 MHz, CDCl₃) δ1.55 (d, 6H), 1.75–2.00 (m, 4H), 2.65–2.80 (m, 4H), 2.92 (t, 2H), 2.96 (S, 3H), 3.64 (t, 2H), 4.56 (sep, 1H), 6.18 (brs, 1H), 6.89 (dd, 1H), 7.20 (d, 2H), 7.31 (d, 1H), 7.40 (d, 1H), 8.52 (d, 2H)

FAB-MS (m/e) 391 (M+H)⁺

Example 103

Synthesis of Compound 5-21

Compound 5-6 (195 mg) obtained by the method described in Example 88 was dissolved in 5 mL of pyridine, and the solution was added with 50.6 µl of methanesulfonyl chloride, and stirred at room temperature for 2.5 hours. The reaction was stopped with water, and the reaction mixture was extracted with ethyl acetate. The organic layer was washed twice with 1 N hydrochloric acid, once with water and once with saturated brine and concentrated under reduced pressure. The residue without purification was dissolved in 5 mL of dimethylformamide, and the solution was added with 111 mg of phthalimide potassium salt, and stirred at room temperature for 1.5 hours. The reaction was stopped with water, and the reaction mixture was extracted with ethyl acetate. The organic layer was washed twice with water and once with saturated brine and then concentrated under reduced pressure. The residue was purified by silica gel column chromatography (chloroform) to obtain 153 mg of Compound 5-21.

$^1$H-NMR (300 MHz, CDCl$_3$) δ1.55 (d, 6H), 1.6–2.0 (m, 8H), 2.6–2.7 (m, 4H), 3.01 (s, 3H), 3.44 (t, 2H), 3.75 (t, 2H), 4.54 (m, 1H), 6.43 (bs, 1H), 7.07 (dd, 1H), 7.27 (d, 1H), 7.48 (d, 1H), 7.70 (m, 2H), 7.83 (m, 2H)

FAB-MS (m/e) 486 (M)$^+$

Example 104

Synthesis of Compound 5-22

1-(3-Aminopropyl)imidazole (5.00 g) was dissolved in 40 mL of acetonitrile, and the solution was added with 5.03 g of sodium hydrogencarbonate and cooled with ice. The reaction mixture was slowly added with 6.55 mL of benzyloxycarbonyl chloride and stirred at room temperature for 1 hour. Then, the solvent was evaporated under reduced pressure and the residue was diluted with water. The reaction mixture was diluted with water and extracted with ethyl acetate, and the organic layer was washed with water and saturated brine and concentrated under reduced pressure. The resulting residue was purified by silica gel column chromatography (methanol/chloroform=1/20) to obtain a benzyloxycarbonylamino compound (9.28 g).

Then, the resulting benzyloxycarbonylamino compound (1.31 g) was placed in a 200-mL three-neck flask and nitrogen substitution was performed. The compound was added with anhydrous tetrahydrofuran (15 mL), and the solution was cooled with ice and slowly added with 336 mg of lithium aluminum hydride, and then heated at 60° C. for 30 minutes with stirring. After the reaction was stopped with methanol and insoluble solids were removed by filtration, the reaction mixture was dried over anhydrous magnesium sulfate and concentrated under reduced pressure. The residue without purification was dissolved in 30 mL of chloroform, and refluxed for 1.5 hours with heating together with 230 mg of N-isopropyl-6-phenoxycarbonylamino-1,2,3,4-tetrahydrocarbazole. The reaction mixture was concentrated under reduced pressure, and the residue was purified by silica gel column chromatography (methanol/chloroform=1/20) to obtain 220 mg of Compound 5-22.

$^1$H-NMR (300 MHz, CDCl$_3$) δ1.58 (d, 6H), 1.8–2.0 (m, 4H), 2.10 (m, 2H), 2.72 (m, 4H), 3.01 (s, 3H), 3.48 (t, 2H), 4.04 (t, 2H), 4.58 (m, 1H), 6.30 (bs, 1H), 7.00 (s, 1H), 7.05 (dd, 1H), 7.09 (s, 1H), 7.35 (d, 1H), 7.46 (d, 1H), 7.54 (s, 1H)

FAB-MS (m/e) 394 (M+H)$^+$

Example 105

Synthesis of Compound 5-23

2-Aminoethanol (7.2 mL) was dissolved in of 20 mL of toluene, and the solution was cooled with ice and slowly added dropwise with a mixture of benzyloxycarbonyl chloride (7.2 mL) and toluene (40 mL). The reaction mixture was stirred for 1 hour, then washed twice with water and once with saturated brine, and then dried over anhydrous magnesium sulfate and concentrated under reduced pressure. The resulting residue was recrystallized from a mixture of hexane/ethyl acetate=1/1 to obtain a benzyloxycarbonylamino compound (8.20 g).

The resulting benzyloxycarbonylamino compound (5.40 g) was dissolved in 30 mL of pyridine, and the solution was cooled with ice and added with 6.33 g of tosyl chloride, and then stirred for 1.5 hours. The reaction was stopped with water, and the reaction mixture was extracted with ethyl acetate. The organic layer was washed twice with 1 N hydrochloric acid, once with water and once with saturated brine and then concentrated under reduced pressure. The deposited solid was purified by washing with ethyl acetate to obtain a tosylate (5.40 g).

Subsequently, the resulting tosylate (2.26 g) was dissolved in 15 mL of acetonitrile, and the solution was added successively with 654 mg of 3-mercapto-1,2,4-triazole and 1.35 mL of triethylamine, and heated at 80° C. for 7 hours. After the solvent was evaporated, the residue was added with water and extracted with ethyl acetate. The organic layer was washed with saturated brine, dried over anhydrous magnesium sulfate, and concentrated under reduced pressure. The residue was purified by silica gel column chromatography (methanol/chloroform=1/50) to obtain a triazole-substituted compound (1.39 mg).

The resulting triazole-substituted compound (552 mg) was placed in a 200-mL three-neck flask. After nitrogen substitution, the compound was cooled with ice and added with 15 mL of anhydrous tetrahydrofuran and 151 mg of lithium aluminum hydride, and then stirred over an oil bath at 70° C. for 3 hours. The reaction mixture was left stand for cooling, and then the mixture was added with ethyl acetate, and further added with a small amount of water and filtered. The filtrate was dried over anhydrous magnesium sulfate and concentrated under reduced pressure. The residue was dissolved in 20 mL of chloroform, and the solution was added with 75 mg of N-isopropyl-6-phenoxycarbonylamino-1,2,3,4-tetrahydrocarbazole and heated under reflux for 1 hour. The solvent was evaporated, and the residue was purified by silica gel column chromatography (methanol/chloroform=3/97 to 5/96) to obtain 116 mg of Compound 5-23.

$^1$H-NMR (300 MHz, CDCl$_3$) δ1.56 (d, 6H), 1.8–2.0 (m, 4H), 2.6–2.8 (m, 4H), 3.13 (s, 3H), 3.30 (t, 2H), 3.67 (t, 2H), 4.55 (m, 1H), 7.08 (dd, 1H), 7.33 (d, 1H), 7.40 (d, 1H), 8.00 (s, 1H)

FAB-MS (m/e) 412 (M)$^+$

Example 106

Synthesis of Compound 5-24

Synthesis was performed in the same manner as in Example 105 except that 3-amino-1-propanol was used instead of the 2-aminoethanol mentioned in the description of Example 105.

Example 107

Synthesis of Compound 5-25

Synthesis was performed in the same manner as in Example 105 except that 2-mercaptoimidazole was used instead of the 3-mercapto-1,2,4-triazole mentioned in the description of Example 105.

$^1$H-NMR (300 MHz, CDCl$_3$) δ1.56 (d, 6H), 1.8–2.0 (m, 4H), 2.6–2.8 (m, 4H), 3.09 (s, 3H), 3.10 (t, 2H), 3.69 (t, 2H), 4.57 (m, 1H), 7.04 (s, 2H), 7.11 (dd, 1H), 7.34 (d, 1H), 7.43 (d, 1H)

MS (m/e) 412 (M+H)$^+$

Example 108

Synthesis of Compound 5-26

Synthesis was performed in the same manner as in Example 74 except that 3-methylamino-1,2-propanediol was used instead of the hydroxyethylamine mentioned in the description of Example 74.

$^1$H-NMR (300 MHz, CDCl$_3$) δ1.56 (d, 6H), 1.8–2.0 (m, 4H), 2.6–2.8 (m, 4H), 3.09 (s, 3H), 3.34 (d, 2H), 3.50 (br, 2H), 3.84 (m, 1H), 4.55 (sep., 1H), 6.98 (dd, 1H), 7.26 (d, 1H), 7.38 (d, 1H)

MS (m/e) 359 (M)$^+$

Example 109

Synthesis of Compound 6-1

Synthesis was performed in the same manner as in Example 74 except that 4-ethylaminobutanol was used instead of the hydroxyethylamine mentioned in the description of Example 74.

$^1$H-NMR (300 MHz, CDCl$_3$) δ1.38 (t, 3H), 1.56 (d, 6H), 1.60–2.00 (m, 8H). 2.60–2.80 (m, 4H), 3.32–3.46 (m, 4H), 3.68 (t, 2H), 4.58 (sep, 1H), 6.60 (br, 1H), 7.08 (dd, 1H), 7.32(d, 1H), 7.48 (d, 1H)

FAB-MS (m/e) 372 (M+H)$^+$

Example 110

Synthesis of Compound 6-2

Synthesis was performed in the same manner as in Example 74 except that diethanolamine was used instead of the hydroxyethylamine mentioned in the description of Example 74.

$^1$H-NMR (300 MHz, CDCl$_3$) δ1.56 (d, 6H), 1.80–2.00 (m, 4H), 2.60–2.80 (m, 4H), 3.48 (t, 4H), 3.78 (t, 4H), 4.08 n (br, 2H), 4.56 (sep., 1H), 7.06 (dd, 1H), 7.32(d, 1H), 7.40 (d, 1H), 8.28 (s, 1H)

FAB-MS (m/e) 359 (M)$^+$

Example 111

Synthesis of Compound 6-3

Synthesis was performed in the same manner as in Example 74 except that di(2-methoxyethyl)amine was used instead of the hydroxyethylamine mentioned in the description of Example 74.

$^1$H-NMR (300 MHz, CDCl$_3$) δ1.54 (d, 6H), 1.75–2.00 (m, 4H), 2.60–2.80 (m, 4H), 3.40 (s, 6H), 3.55–3.70 (m 8H), 4.54 (sep, 1H), 6.94 (dd, 1H), 7.30 (d, 1H), 7.44 (d 1H), 8.14 (br, 1H)

FAB-MS (m/e) 387 (M)$^+$

Example 112

Synthesis of Compound 7-1

Synthesis was performed in the same manner as in Example 74 except that pyrrolidine was used instead of the hydroxyethylamine mentioned in the description of Example 74.

$^1$H-NMR (300 MHz, CDCl$_3$) δ1.55 (d, 6H), 1.80–2.00 (m, 8H), 2.60–2.80 (m, 4H), 3.40–3.50 (m, 4H), 4.55 (sep., 1H), 6.14 (br, 1H), 7.04 (dd, 1H), 7.30 (d, 1H), 7.50 (d, 1H)

FAB-MS (m/e) 325 (M)$^+$

Example 113

Synthesis of Compound 7-2

Synthesis was performed in the same manner as in Example 74 except that piperidine was used instead of the hydroxyethylamine mentioned in the description of Example 74.

$^1$H-NMR (300 MHz, CDCl$_3$) δ1.50–2.00 (m+d, 16H), 2.60–2.80 (m, 4H), 3.50–3.80 (m, 4H), 4.55 (sep, 1H), 6.15 (br, 1H), 7.04 (dd, 1H), 7.31(d, 1H), 7.48 (d, 1H)

FAB-MS (m/e) 340 (M+H)$^+$

Example 114

Synthesis of Compound 7-3

Synthesis was performed in the same manner as in Example 74 except that hexamethyleneimine was used instead of the hydroxyethylamine mentioned in the description of Example 74.

$^1$H-NMR (300 MHz, CDCl$_3$) δ1.55 (d, 6H), 1.60–2.00 (m, 12H), 2.60–2.80 (m, 4H), 3.50–3.60 (m, 4H), 4.55 (sep, 1H), 6.28 (br, 1H), 7.03 (dd, 1H), 7.31(d, 1H), 7.48 (d, 1H)

FAB-MS (m/e) 353 (M)$^+$

Example 115

Synthesis of Compound 7-4

Synthesis was performed in the same manner as in Example 74 except that 3-pyrrolidinol was used instead of the hydroxyethylamine mentioned in the description of Example 74.

$^1$H-NMR (200 MHz, CDCl$_3$) δ1.50–2.00 (m+d, 14H), 2.60–2.80 (m, 4H), 3.45–3.80 (m, 4H), 4.20 (br, 1H), 4.55 (sep, 1H), 6.20 (br, 1H), 7.04 (dd, 1H), 7.32(d, 1H), 7.40 (d, 1H)

FAB-MS (m/e) 340 (M–H)$^+$

Example 116

Synthesis of Compound 7-5

Synthesis was performed in the same manner as in Example 74 except that (s)-(+)-2-pyrrolidinemethanol was used instead of the hydroxyethylamine mentioned in the description of Example 74.

$^1$H-NMR (200 MHz, CDCl$_3$) δ1.50–1.80 (m+d, 7H), 1.80–2.00 (m, 7H), 2.60–2.80 (m, 4H), 3.45–3.80 (m, 4H),

---

$^1$H-NMR (300 MHz, CDCl$_3$) δ1.54 (d, 6H), 1.7–1.9 (m, 6H), 2.6–2.8 (m, 4H), 2.99 (s, 3H), 3.53 (t, 2H), 3.62 (t, 2H), 3.96 (b, 1H), 4.54 (m, 1H), 6.70 (bs, 1H), 7.03 (dd, 1H) 7.30–7.40 (m, 2H), 7.41 (d, 1H)

MS (m/e) 427 (M+H)$^+$ 4.20 (br, 1H), 4.55 (sep., 1H), 6.20 (br, 1H), 7.04 (dd, 1H), 7.32(d, 1H), 7.40 (d, 1H)

FAB-MS (m/e) 354 (M−H)$^+$

Example 117

Synthesis of Compound 7-6

Synthesis was performed in the same manner as in Example 74 except that (R)-(−)-2-pyrrolidinemethanol was used instead of the hydroxyethylamine mentioned in the description of Example 74.

$^1$H-NMR (200 MHz, CDCl$_3$) δ1.50–1.80 (m+d, 7H), 1.80–2.00 (m, 7H), 2.60–2.80 (m 4H), 3.45–3.80 (m, 4H), 4.20 (br, 1H), 4.55 (sep, 1H), 6.70 (br, 1H), 7.05 (dd, 1H), 7.32(d, 1H), 7.41 (d, 1H)

FAB-MS (m/e) 354 (M−H)$^+$

Example 118

Synthesis of Compound 7-7

Synthesis was performed in the same manner as in Example 74 except that 4-hydroxypiperidine was used instead of the hydroxyethylamine mentioned in the description of Example 74.

$^1$H-NMR (300 MHz, CDCl$_3$) δ1.50–1.80 (m+d, 8H), 1.80–2.00 (m, 6H), 2.60–2.80 (m, 4H), 3.10–3.20 (m, 2H), 3.80–4.00 (m, 3H), 4.55 (sep., 1H), 6.34 (br, 1H), 6.99 (dd, 1H), 7.32(d, 1H), 7.41 (d, 1H)

FAB-MS (m/e) 355 (M)$^+$

Example 119

Synthesis of Compound 7-8

Synthesis was performed in the same manner as in Example 74 except that 3-hydroxypiperidine was used instead of the hydroxyethylamine mentioned in the description of Example 74.

$^1$H-NMR (300 MHz, CDCl$_3$) δ1.50–1.80 (m+d, 8H), 1.80–2.00 (m, 6H), 2.60–2.80 (m, 4H), 3.30–3.50 (m, 3H), 3.39 (dd, 2H), 3.57 (m, 1H), 4.54 (sep., 1H), 6.34 (br, 1H), 6.99 (dd, 1H), 7.32(d, 1H), 7.41 (d, 1H)

FAB-MS (m/e) 354 (M−H)$^+$

Example 120

Synthesis of Compound 7-9

Synthesis was performed in the same manner as in Example 74 except that 2-piperidinemethanol was used instead of the hydroxyethylamine mentioned in the description of Example 74.

$^1$H-NMR (300 MHz, CDCl$_3$) δ1.50–1.80 (m+d, 12H), 1.80–2.00 (m, 4H), 2.60–2.80 (m, 4H), 2.80–3.00 (m, 1H), 3.58 (dd, 1H), 3.92 (m, 2H), 4.30–4.40 (br, 1H), 4.54 (sep, 1H), 6.98 (dd, 1H), 7.29(d, 1H), 7.35 (d, 1H)

FAB-MS (m/e) 369 (M)$^+$

Example 121

Synthesis of Compound 7-10

Synthesis was performed in the same manner as in Example 74 except that 3-piperidinemethanol was used instead of the hydroxyethylamine mentioned in the description of Example 74.

$^1$H-NMR (300 MHz, CDCl$_3$) δ1.50–1.80 (m, 11H), 1.80–2.00 (m, 4H), 2.60–2.80 (m, 4H), 3.35–3.50 (m, 2H), 3.50–3.62 (m, 4H), 4.55 (sep., 1H),6.60 (br, 1H), 7.02 (dd, 1H), 7.31 (d, 1H), 7.41 (d, 1H)

FAB-MS (m/e) 369 (M)$^+$

Example 122

Synthesis of Compound 7-11

Synthesis was performed in the same manner as in Example 74 except that 2-piperidineethanol was used instead of the hydroxyethylamine mentioned in the description of Example 74.

$^1$H-NMR (200 MHz, CDCl$_3$) δ1.50–2.00 (m+d, 18H), 2.60–2.80 (m+t, 6H), 3.50–4.00 (m, 3H), 4.58 (m, 2H), 6.85 (br, 1H), 7.06 (dd, 1H), 7.36(d, 1H), 7.40 (d, 1H)

FAB-MS (m/e) 384 (M)$^+$

Example 123

Synthesis of Compound 7-12

Synthesis was performed in the same manner as in Example 74 except that 4-piperidineethanol was used instead of the hydroxyethylamine mentioned in the description of Example 74.

$^1$H-NMR (200 MHz, CDCl$_3$) δ1.20–2.00 (m+d, 17H), 2.60–2.80 (m+t, 6H), 3.70–4.00 (m, 2H), 4.00–4.20 (m, 2H), 4.56 (sep, 1H), 6.45 (br, 1H), 7.06 (dd, 1H), 7.36(d, 1H), 7.40 (d, 1H)

FAB-MS (m/e) 384 (M+H)$^+$

Example 124

Synthesis of Compound 7-13

Synthesis was performed in the same manner as in Example 74 except that 4-piperidinopiperidine was used instead of the hydroxyethylamine mentioned in the description of Example 74.

$^1$H-NMR (300 MHz, CDCl$_3$) δ1.45–2.00 (d, 20H), 2.45–2.60 (m, 5H), 2.66 (t, 2H), 2.72 (t, 2H), 2.86 (ddd, 2H), 4.15 (ddd, 2H), 4.55 (sep, 1H), 6.34 (br, 1H), 6.99 (dd, 1H), 7.31(d, 1H), 7.41 (d, 1H)

FAB-MS (m/e) 423 (M+H)$^+$

Example 125

Synthesis of Compound 7-14

Synthesis was performed in the same manner as in Example 74 except that isothiazolidine was used instead of the hydroxyethylamine mentioned in the description of Example 74.

$^1$H-NMR (300 MHz, CDCl$_3$) δ1.55 (d, 6H), 1.80–2.00 (m, 4H), 2.60–2.80 (m, 4H), 3.11 (t, 2H), 3.79 (t, 2H), 4.55 (sep., 1H), 4.58 (s, 2H), 6.25 (br, 1H), 7.02 (dd, 1H), 7.32 (d, 1H), 7.44 (d, 1H)

FAB-MS (m/e) 343 (M)$^+$

Example 126

Synthesis of Compound 7-15

Synthesis was performed in the same manner as in Example 74 except that thiomorpholine was used instead of the hydroxyethylamine mentioned in the description of Example 74.

$^1$H-NMR (300 MHz, dmso-d$_6$) δ1.48 (d, 6H), 1.80–2.00 (m, 4H), 2.54–2.60 (m, 6H), 2.70–2.75 (m, 2H ), 3.70–3.75

(m, 4H), 4.55 (sep., 1H), 7.04 (dd, 1H), 7.33 (d, 1H), 7.38 (d, 1H), 8.29 (s, 1H)

FAB-MS (m/e) 357 (M)$^+$

Example 127

Synthesis of Compound 7-16

Synthesis was performed in the same manner as in Example 74 except that 2,6-dimethylmorpholine was used instead of the hydroxyethylamine mentioned in the description of Example 74.

$^1$H-NMR (300 MHz, CDCl$_3$) δ1.21 (d, 6H), 1.55 (d, 6H), 1.80–2.00 (m, 4H), 2.60–2.80 (m, 4H), 3.30–3.50 (m, 2H), 3.64 (d, 1H), 3.65 (d, 1H), 4.56 (sep, 1H), 6.40 (br, 1H), 7.06 (dd, 1H), 7.34(d, 1H), 7.41 (d, 1H)

FAB-MS (m/e) 368 (M–H)$^+$

Example 128

Synthesis of Compound 7-17

Synthesis was performed in the same manner as in Example 74 except that 2-hydroxyethylmorpholine was used instead of the hydroxyethylamine mentioned in the description of Example 74.

$^1$H-NMR (300 MHz, dmso-d$_6$) δ1.50–1.75 (m+d, 8H), 1.75–2.00 (m, 4H), 2.33 (br, 1H), 2.60–2.75 (m, 5H), 2.80–3.04 (m, 1H), 3.45–3.60 (m, 2H), 3.65–3.90 (m, 5H), 4.55 (sep., 1H), 6.64 (br, 1H), 6.99 (dd, 1H), 7.31 (d, 1H), 7.39 (d, 1H)

FAB-MS (m/e) 385 (M)$^+$

Example 129

Synthesis of Compound 7-18

Synthesis was performed in the same manner as in Example 74 except that piperazine was used instead of the hydroxyethylamine mentioned in the description of Example 74.

$^1$H-NMR (300 MHz, CDCl$_3$) δ1.55 (d, 6H), 1.80–2.00 (m, 4H), 2.60–2.80 (m, 4H), 2.92 (t, 4H ), 3.48 (t, 4H), 4.55 (sep., 1H), 6.35 (br, 1H), 7.00 (dd, 1H), 7.31 (d, 1H), 7.42 (d, 1H)

FAB-MS (m/e) 341 (M+H)$^+$

Example 130

Synthesis of Compound 7-19

Synthesis was performed in the same manner as in Example 74 except that N-methylpiperazine was used instead of the hydroxyethylamine mentioned in the description of Example 74.

$^1$H-NMR (300 MHz, CDCl$_3$) δ1.55 (d, 6H), 1.80–2.00 (m, 4H), 2.37 (s, 3H), 2.51 (t, 4H), 2.60–2.80 (m, 4H), 3.55 (t, 4H ), 4.55 (sep., 1H), 6.32 (br, 1H), 6.99 (dd, 1H), 7.31 (d, 1H), 7.41 (d, 1H)

FAB-MS (m/e) 354 (M)$^+$

Example 131

Synthesis of Compound 7-20

Synthesis was performed in the same manner as in Example 74 except that 1-(2-pyridyl)piperazine was used instead of the hydroxyethylamine mentioned in the description of Example 74.

$^1$H-NMR (300 MHz, CDCl$_3$) δ1.56 (d, 6H), 1.80–2.00 (m, 4H), 2.60–2.80 (m, 4H), 3.66 (br, 8H), 4.56 (sep., 1H), 6.35 (br, 1H), 6.60–6.70 (m, 2H), 7.03 (dd, 1H), 7.33 (d, 1H), 7.44 (d, 1H), 7.52 (ddd, 1H), 8.21 (dd, 1H)

FAB-MS (m/e) 418 (M+H)$^+$

Example 132

Synthesis of Compound 7-21

Synthesis was performed in the same manner as in Example 74 except that 1-(2-pyrimidyl)piperazine was used instead of the hydroxyethylamine mentioned in the description of Example 74.

$^1$H-NMR (300 MHz, CDCl$_3$) δ1.56 (d, 6H), 1.80–2.00 (m, 4H), 2.60–2.80 (m, 4H), 3.61 (t, 4H ), 3.93 (t, 4H), 4.56 (sep., 1H), 6.55 (t, 1H), 7.03 (dd, 1H), 7.33 (d, 1H), 7.44 (d, 1H), 8.35 (d, 2H)

FAB-MS (m/e) 418 (M)$^+$

Example 133

Synthesis of Compound 7-22

N-Z-Ethanolamine (1.57 g) and N-Boc-piperazine (0.93 g) were dissolved in 50 mL of acetonitrile, and the solution was added with 1.39 g of potassium carbonate and stirred at 50° C. for 5 hours. The reaction mixture was concentrated under reduced pressure, and the residue was added with water and extracted with ethyl acetate. The organic layer was washed with water, dried over anhydrous sodium sulfate, and concentrated under reduced pressure. The residue was purified by silica gel chromatography (hexane/ethyl acetate= 7/3) to obtain 1.33 g of N-Z-(N-Boc-piperazino)ethylamine.

The resulting N-Z-(N-Boc-piperazino)ethylamine (1.33 g) was dissolved in 5 mL of dioxane, and the solution was added with 5 mL of 4 N hydrochloric acid solution in dioxane, and stirred at room temperature for 2 hours. The reaction mixture was concentrated under reduced pressure and the residue was dissolved in 1 N hydrochloric acid. The aqueous layer was washed with ethyl acetate, adjusted to pH 9 with 40% aqueous sodium hydroxide, and extracted with ethyl acetate. The extract was dried over anhydrous sodium sulfate and concentrated under reduced pressure to obtain 610 mg of N-Z-ethylamine.

The resulting N-Z-ethylamine (610 mg) and N-isopropyl-6-phenoxycarbonyl-amino-1,2,3,4-tetrahydrocarbazole (810 mg) obtained by the method of Example 3 were dissolved in 3 ml of dichloromethane, and the solution was added with 232 mg of triethylamine and 3 mL of acetonitrile, and stirred at 80° C for 20 hours. The reaction mixture was concentrated under reduced pressure, and the residue was added with saturated aqueous sodium hydrogencarbonate, and extracted with dichloromethane. The extract was dried over anhydrous sodium sulfate and concentrated under reduced pressure, and the residue was purified by silica gel chromatography (hexane/ethyl acetate=3/7) to obtain 0.53 g of N-isopropyl-6-(2-(N-Z-amino)ethyl)piperazinocarbonylamino-1,2,3,4-tetrahydrocarbazole.

The carbazole derivative (258 mg) obtained above was dissolved in 20 mL of methanol, and the solution was added with 50 mg of 10% palladium/carbon, and stirred under hydrogen atmosphere for 16 hours. Insoluble solids were removed by filtration, and the filtrate was concentrated under reduced pressure. The residue was purified by silica gel chromatography (chloroform/methanol=8/2 to 7/3) to obtain 120 mg of N-isopropyl-6-(2-aminoethyl) piperadinocarbonylamino-1,2,3,4-tetrahydrocarbazole.

The resulting amine compound (100 mg) was dissolved in dichloromethane, and the solution was added with 55 mg of isopropylsulfonyl chloride and 39 mg of triethylamine, and stirred at room temperature for 8 hours. The reaction mixture was added with saturated aqueous sodium hydrogencarbonate and extracted with dichloromethane, and the organic layer was dried over anhydrous sodium sulfate and concentrated under reduced pressure. The residue was purified by silica gel thin layer chromatography (dichloromethane/methanol=1/1) to obtain 16 mg of Compound 7-22.

$^1$H-NMR (300 MHz, CDCl$_3$) δ1.37 (d, 6H), 1.56 (d, 6H), 1.80–2.00 (m, 4H), 2.45 (t, 4H), 2.51 (t, 2H), 2.60–2,80 (m, 4H), 3.18 (t, 2H ), 3.46 (t, 4H), 4.56 (sep., 1H), 4.86 (br, 1H), 6.50 (br, 1H), 7.01 (dd, 1H), 7.30 (d, 1H), 7.41 (d, 1H)

FAB-MS (m/e) 489 (M)$^+$

Example 134

Synthesis of Compound 8-1

Ammonium chloride (1.27 g) was dissolved in 24 mL of water, and the solution was added with 240 mL of isopropyl alcohol and 13.1 g of iron powder and refluxed for 15 minutes with stirring. Subsequently, the reaction mixture was added with 6-nitro-1,2,3,4-tetrahydrocarbazole (10.0 g) prepared by the method described in Journal of Chemical Society, p.833 (1924), stirred for 5 hours, further added with ammonium chloride (0.53 g) and iron powder (5.19 g), and then stirred for 4 hours. After the reaction mixture was left stand for cooling to room temperature, insoluble solids were removed by filtration and the filtrate was concentrated. Then, the residue was dissolved in 72 ml of tetrahydrofuran and added dropwise with a mixed solution of 5.66 g of triethylamine and 5.83 g of morpholinocarbonyl chloride in 15 ml of tetrahydrofuran. The mixture was stirred at room temperature for 1 hour and half, then left at room temperature for one day. The mixture was added with water, and extracted with dichloromethane. The organic layer was washed with 0.2 N hydrochloric acid, water and then with saturated brine, dried over sodium sulfate, and concentrated under reduced pressure. The residue was washed with a mixture of dichloromethane and methanol and dried under reduced pressure to obtain 5.64 g of 6-morpholinocarbonylamino-1,2,3,4-tetrahydrocarbazole.

The 6-morpholinocarbonylamino-1,2,3,4-tetrahydrocarbazole (503 mg) obtained above was dissolved in 8 ml of dimethylformamide, and the solution was added with 414 mg of potassium hydroxide, and added dropwise with a mixed solution of 237 mg of methyl iodide and 8 ml of dimethylformamide. The reaction mixture was stirred at room temperature for 15 minutes, added with water and then added with 2 N hydrochloric acid. The resulting precipitates were taken by filtration. The resulting precipitates were recrystallized from a mixed solvent of methanol and ethyl acetate to obtain 89 mg of Compound 8-1.

$^1$H-NMR (300 MHz, CDCl$_3$) δ1.80–2.00 (m, 4H), 2.62–2.75 (m, 4H), 3.48 (t, 4H), 3.60 (s, 3H), 3.75 (t, 4H), 6.35 (br, 1H), 7.04 (dd, 1H), 7.16 (d, 1H), 7.45 (d, 1H)

FAB-MS (m/e) 313 (M)$^+$

Example 135

Synthesis of Compound 8-2

The 6-morpholinocarbonylamino-1,2,3,4-tetrahydrocarbazole (503 mg) obtained in Example 134 was dissolved in 15 mL of dimethylformamide, and the solution was added with 414 mg of potassium hydroxide and then added dropwise with 160 μl of ethyl iodide, and the mixture was stirred at room temperature for 1 hour. The reaction mixture was added with water, neutralized by addition of 2 N hydrochloric acid and then extracted with ethyl acetate. The extract was washed with 0.2 N hydrochloric acid, water and then with saturated aqueous sodium hydrogencarbonate, dried over anhydrous sodium sulfate, and concentrated under reduced pressure. The residue was purified by silica gel chromatography (dichloromethane/ethyl acetate=1/1) to obtain 138 mg of Compound 8-2.

$^1$H-NMR (300 MHz, CDCl$_3$) δ1.30 (t, 3H), 1.8–2.0 (m, 4H), 2.62–2.80 (m, 4H), 3.46 (t, 4H), 3.73 (t, 4H), 4.04 (q, 2H), 6.40 (brs, 1H), 7.03 (dd, 1H), 7.17 (d, 1H), 7.43 (d, 1H)

FAB-MS (m/e) 328 (M+H)$^+$

Example 136

Synthesis of Compound 8-3

Synthesis was performed in the same manner as in Example 135 except that propyl iodide was used instead of the ethyl iodide mentioned in the description of Example 135.

$^1$H-NMR (300 MHz, CDCl$_3$) δ0.92 (t, 3H), 1.76 (m, 2H), 1.80–2.00 (m, 4H), 2.60–2.70 (m, 4H), 3.47 (t, 4H), 3.74 (t, 4H), 3.94 (t, 2H), 6.33 (br, 1H), 7.02 (dd, 1H), 7.17 (d, 1H) 7.43 (d, 1H)

FAB-MS (m/e) 341 (M)$^+$

Example 137

Synthesis of Compound 8-4

The N-isopropyl-6-amino-1,2,3,4-tetrahydrocarbazole (2.28 g) obtained in Example 71, 1.80 g of 4-morpholinocarbonyl chloride and 1.20 g of triethylamine were dissolved in 20 mL of tetrahydrofuran, and the solution was stirred overnight at room temperature. The reaction mixture was concentrated under reduced pressure and then added with ethyl acetate, and the organic layer was washed with 10% aqueous citric acid and then with saturated aqueous sodium hydrogencarbonate, and dried over anhydrous sodium sulfate. The solvent was evaporated under reduced pressure, and the residue was purified by silica gel chromatography (eluent: dichloromethane/ethyl acetate=8/2) and recrystallized from ethanol to obtain 1.30 g of Compound 8-4.

$^1$H-NMR (300 MHz, CDCl$_3$) δ1.56 (d, 6H), 1.80–2.00 (m, 4H), 2.62–2.75 (m, 4H), 3.48 (t, 4H), 3.75 (t, 4H), 4.55 (sep. 1H), 6.27 (br, 1H), 7.00 (dd, 1H), 7.32 (d, 1H), 7.41 (d, 1H)

FAB-MS (m/e) 341 (M)$^+$

Example 138

Synthesis of Compound 8-5

Butyl iodide was used instead of the propyl iodide mentioned in the description of Example 70, and synthesis was performed in the same manner as in Examples 71 and 135 except that.

$^1$H-NMR (300 MHz, CDCl$_3$) δ0.93 (t, 3H), 1.34 (m, 2H), 1.69 (m, 2H), 1.80–2.00 (m, 4H), 2.68 (m, 4H), 3.48 (t, 4H), 3.75 (t, 4H), 3.97 (t, 2H), 6.29 (brs, 1H), 7.02 (dd, 1H), 7.16 (d, 1H), 7.43 (d, 1H)

FAB-MS (m/e) 355 (M)$^+$

Example 139

Synthesis of Compound 8-6

Synthesis was performed in the same manner as in Example 135 except that isobutyl iodide was used instead of the ethyl iodide mentioned in the description of Example 135.

¹H-NMR (300 MHz, CDCl₃) δ0.90 (d, 6H), 1.80–2.00 (m, 4H), 2.15 (sep., 1H), 2.68 (t, 4H), 3.47 (t, 4H), 3.71–3.77 (m, 6H), 6.31 (brs, 1H), 7.02 (dd, 1H), 7.15 (d, 1H), 7.43 (d, 1H)

FAB-MS (m/e) 355 (M)⁺

Example 140

Synthesis of Compound 8-7

Synthesis was performed in the same manner as in Example 135 except that bromomethylcyclopropane was used instead of the ethyl iodide mentioned in the description of Example 135.

¹H-NMR (300 MHz, CDCl₃) δ0.25–0.35 (m, 2H), 0.45–0.55 (m, 2H), 1.10–1.25 (m, 1H), 1.80–2.00 (m, 4H), 2.60–2.75 (m, 4H), 3.48 (t, 4H), 3.74 (t, 4H), 3.89 (d, 2H), 6.30 (brs, 1H), 7.03 (dd, 1H), 7.20 (d, 1H), 7.43 (d, 1H)

FAB-MS (m/e) 353 (M)⁺

Example 141

Synthesis of Compound 8-8

Synthesis was performed in the same manner as in Example 135 except that bromoethyl methyl ether was used instead of the ethyl iodide mentioned in the description of Example 135.

¹H-NMR (300 MHz, CDCl₃) δ1.80–2.00 (m, 4H), 2.60–2.80 (m, 4H), 3.28 (s, 3H), 3.48 (t, 4H), 3.60 (t, 2H), 3.74 (t, 4H), 4.16 (t, 2H), 6.35 (br, 1H), 7.03 (dd, 1H), 7.18 (d, 1H), 7.43 (d, 1H)

FAB-MS (m/e) 367 (M)⁺

Example 142

Synthesis of Compound 8-9

Synthesis was performed in the same manner as in Example 135 except that bromoethanol was used instead of the ethyl iodide mentioned in the description of Example 135.

¹H-NMR (300 MHz, CDCl₃) δ1.80–2.00 (m, 4H), 2.60–2.80 (m, 4H), 3.50 (t, 4H), 3.77 (t, 4H), 3.91 (t, 2H), 4.19 (t, 2H), 6.42 (brs, 1H), 7.05 (dd, 1H), 7.14 (d, 1H), 7.48 (d, 1H)

FAB-MS (m/e) 343 (M)⁺

Example 143

Synthesis of Compound 8-10

Chloroacetonitrile was used instead of the propyl iodide mentioned in the description of Example 70, and synthesis was performed in the same manner as in Examples 71 and 135.

¹H-NMR (300 MHz, CDCl₃) δ1.75–2.10 (m, 4H), 2.55–2.80 (m, 4H), 3.48 (t, 4H), 3.76 (t, 4H), 4.87 (s, 2H), 6.34 (brs, 1H), 7.10 (dd, 1H), 7.19 (d, 1H), 7.53 (d, 1H)

FAB-MS (m/e) 338 (M)⁺

Example 144

Synthesis of Compound 8-11

The 6-morpholinocarbonylamino-1,2,3,4-tetrahydrocarbazole (503 mg) obtained in Example 134 was added with 5 mL of acetic anhydride and stirred for 30 minutes, and then the mixture was added with several drops of trifluoroborane ether complex and stirred for 2 hours. The reaction mixture was added with water and extracted with ethyl acetate, and the organic layer was washed with water and saturated brine and dried over anhydrous sodium sulfate. The extract was evaporated under reduced pressure, and the residue was purified by silica gel chromatography (eluent: chloroform/methanol=96/4) to obtain 97 mg of Compound 8-11.

¹H-NMR (300 MHz, CDCl₃) δ1.80–2.00 (m, 4H), 2.62 (t, 2H), 2.65 (s, 3H), 2.97 (t, 2H), 3.50 (t, 4H), 3.75 (t, 4H), 6.45 (brs, 1H), 7.05 (dd, 1H), 7.58 (d, 1H), 7.95 (d, 1H)

FAB-MS (m/e) 342 (M+H)⁺

Example 145

Synthesis of Compound 9-1

3-Methyl-6-nitro-1,2,3,4-tetrahydrocarbazole was prepared from 4-methylcyclohexanone according to the method described in Journal of Chemical Society, p.833 (1924) and then converted into N-isopropyl-3-methyl-6-nitro-1,2,3,4-tetrahydrocarbazole in the same manner as in Exmple 70 and Example 71. Compound 9-1 was synthesized in the same manner as in Example 137.

¹H-NMR (300 MHz, CDCl₃) δ1.10 (d, 3H), 1.54 (d, 3H), 1.56 (d, 3H), 1.50–1.70 (m, 1H), 1.80–2.00 (m, 2H), 2.20–2.30 (m, 1H), 2.70–2.90 (m, 3H), 3.47 (t, 4H), 3.74 (t, 4H), 4.55 (sep., 1H) 6.31 (br, 1H), 6.99 (dd, 1H), 7.32 (d, 1H), 7.40 (d, 1H)

FAB-MS (m/e) 355 (M)⁺

Example 146

Synthesis of Compound 9-2

Compound 9-2 was synthesized in the same manner as in Example 145 except that 4-methoxycyclohexanone was used as the starting material.

¹H-NMR (300 MHz, CDCl₃) δ1.54 (d, 3H), 1.56 (d, 3H), 1.90–2.05 (m, 1H), 2.10–2.30 (m, 1H), 2.64 (dd, 1H), 2.80 (ddd, 1H), 2.86 (ddd, 1H), 3.08 (dd, 1H), 3.44 (s, 3H), 3.50 (t, 4H), 3.68–3.80 (m, 1H), 3.75 (t, 4H), 4.55 (sep., 1H) 6.31 (br, 1H), 6.99 (dd, 1H), 7.32 (d, 1H), 7.44 (d, 1H)

FAB-MS (m/e) 371 (M)⁺

Example 147

Synthesis of Compound 10-1

2-Nitro-hexahydrocyclopent[b]indole was prepared from cyclopentanone according to the method described in Journal of Chemical Society, p.833 (1924) and then Compound 10-1 was synthesized in the same manner as in Examples 70, 71, 72 and 88.

¹H-NMR (300 MHz, CDCl₃) δ1.49 (d, 6H), 1.60–1.80 (m, 6H), 2.49–2.60 (m, 2H), 2.78 (t, 2H), 2.97 (t, 2H), 3.03 (s, 3H), 3.45 (t, 2H), 3.74 (t, 2H), 4.61 (sep., 1H), 6.51 (br, 1H), 7.05 (dd, 1H), 7.22 (d, 1H), 7.47 (d, 1H)

FAB-MS (m/e) 344 (M+H)⁺

Example 148

Synthesis of Compound 10-2

2-Nitro-hexahydrocyclopent[b]indole was prepared from cyclopentanone according to the method described in Journal of Chemical Society, p.833 (1924) and then Compound 10-2 was synthesized in the same manner as in Examples 70, 71, 72 and 100.

¹H-NMR (300 MHz, CDCl₃) δ1.47 (d, 6H), 2.50 (m, 2H), 2.76 (t, 2H), 2.94 (t, 2H), 3.00 (s, 3H), 3.18 (t, 2H), 3.87 (t, 2H), 4.59 (sep., 1H), 7.03 (dd, 1H), 7.19 (d, 1H), 7.19–7.28 (m, 2H), 7.47 (d, 1H), 7.69 (ddd, 1H), 8.61 (ddd, 1H)

FAB-MS (m/e) 377 (M+H)⁺

Example 149

Synthesis of Compound 10-3

2-Nitro-hexahydrocyclopent[b]indole was prepared from cyclopentanone according to the method described in Journal of Chemical Society, p.833 (1924) and then Compound 10-3 was synthesized in the same manner as in Examples 70, 71, 72 and 101.

¹H-NMR (300 MHz, CDCl₃) δ1.47 (d, 6H), 2.51 (m, 2H), 2.76 (t, 2H), 2.90–2.97 (m, 7H), 2.97 (s, 3H), 3.65 (t, 2H), 4.59 (sep., 1H), 6.16 (br, 1H), 6.96 (dd, 1H), 7.18–7.22 (m, 3H), 7.42 (d, 1H), 8.53 (m, 1H)

FAB-MS (m/e) 377 (M+H)⁺

Example 150

Synthesis of Compound 10-4

2-Nitro-hexahydrocyclopent[b]indole was prepared from cyclopentanone according to the method described in Journal of Chemical Society, p.833 (1924) and then Compound 10-4 was synthesized in the same manner as in Examples 70, 71, 72 and 137.

¹H-NMR (300 MHz, CDCl₃) δ1.50 (d, 6H), 2.53 (m, 2H), 2.68 (t, 2H), 2.98 (t, 2H), 3.52 (t, 4H), 3.78 (t, 4H), 4.65 (sep., 1H), 6.37 (br, 1H), 7.02 (dd, 1H), 7.24 (d, 1H), 7.45 (d, 1H)

FAB-MS (m/e) 327 (M)⁺

Example 151

Synthesis of Compound 11-1

2-Nitro-hexahydrocyclohept[b]indole was prepared from cyclohexanone according to the method described in Journal of Chemical Society, p.833 (1924) and then Compound 11-1 was synthesized in the same manner as in Examples 70, 71, 72 and 88.

¹H-NMR (300 MHz, CDCl₃) δ1.50–2.00 (m+d, 16H), 2.60–2.70 (m, 2H), 2.85–3.00 (m, 2H), 3.02 (s, 3H), 3.42 (t, 2H), 3.72 (t, 2H), 4.68 (sep., 1H), 6.47 (br, 1H), 6.99 (dd, 1H), 7.29 (d, 1H), 7.48 (d, 1H)

FAB-MS (m/e) 371 (M)⁺

Example 152

Synthesis of Compound 11-2

2-Nitro-hexahydrocyclohept[b]indole was prepared from cyclohexanone according to the method described in Journal of Chemical Society, p.833 (1924) and then Compound 11-2 was synthesized in the same manner as in Examples 70, 71, 72 and 100.

¹H-NMR (300 MHz, CDCl₃) δ1.57 (d, 6H), 1.60–1.80 (m, 6H), 2.75–2.79 (m, 2H), 2.86–2.90 (m, 2H), 2.97 (s, 3H), 3.14 (t, 2H), 3.85 (t, 2H), 4.68 (sep., 1H), 7.01 (dd, 1H), 7.17 (dd, 1H), 7.18 (d, 2H), 7.29 (d, 1H), 7.51 (d, 1H), 7.62 (ddd, 1H), 7.79 (br, 1H), 8.63 (ddd, 1H)

FAB-MS (m/e) 404 (M)⁺

Example 153

Synthesis of Compound 11-3

2-Nitro-hexahydrocyclohept[b]indole was prepared from cyclohexanone according to the method described in Journal of Chemical Society, p.833 (1924) and then Compound 11-3 was synthesized in the same manner as in Examples 70, 71, 72 and 101.

¹H-NMR (300 MHz, CDCl₃) δ1.57 (d, 3H), 1.60–2.00 (m, 6H), 2.75–2.79 (m, 2H), 2.87–2.95 (m, 4H), 2.97 (s, 3H), 3.65 (t, 2H), 4.69 (sep., 1H), 6.17 (brs, 1H), 6.94 (dd, 1H), 7.19 (dd, 2H), 7.30 (d, 1H), 7.44 (d, 1H), 8.53 (dd, 2H)

FAB-MS (m/e) 404 (M)⁺

Example 154

Synthesis of Compound 11-4

2-Nitro-hexahydrocyclohept[b]indole was prepared from cyclohexanone according to the method described in Journal of Chemical Society, p.833 (1924) and then Compound 11-4 was synthesized in the same manner as in Examples 70, 71, 72 and 137.

¹H-NMR (300 MHz, CDCl₃) δ1.60 (d, 6H), 1.70–1.95 (m, 6H), 2.76–2.84 (m, 2H), 2.88–2.96 (m, 2H), 3.50 (t, 4H), 3.76 (t, 4H), 4.74 (sep., 1H), 6.33 (br, 1H), 6.98 (dd, 1H), 7.34 (d, 1H), 7.47 (d, 1H)

FAB-MS (m/e) 355 (M)⁺

Example 155

Preparation of hydrochloride of Compound 5-18

Compound 5-18 obtained by the method of Example 100 was dissolved in ethyl acetate, and then the solution was added dropwise with 4 N hydrochloric acid in dioxane. The resulting precipitates were washed with ether to obtain hydrochloride of Compound 5-18. Hydrochlorides of Compound 5-20, Compound 5-21, Compound 10-2, Compound 10-3, Compound 11-2 and Compound 11-3 were also prepared in a similar manner.

Example 156

Synthesis of Compound 12-1

3-Fluoro-benzohydrazine (3.3 g) and cyclohexanone (2.2 g) were added to ethanol (30 ml) and the mixture was stirred for 2 hours under reflux. The reaction mixture was concentrated and the resulting residue was recrystallized from hexane to obtain 7-fluoro-carbazole (1.81 g, 48%). Then, concentrated sulfuric acid (20 ml) was cooled to 0° C. and added with 7-fluoro-carbazole (2.1 g) and sodium nitrate (900 mg), and then the mixture was stirred for 10 minutes. The reaction mixture was poured on an ice layer and filtered to obtain 7-fluoro-6-nitro-carbazole (1.1 g, 42%). The resulting 7-fluoro-6-nitro-carbazole (500 mg) and KOH (200 mg) were stirred in acetonitrile as a solvent, and then the mixture was added dropwise with 2-iodopropane (500 mg) and stirred for 8 hours. The reaction mixture was added with water and extracted with ethyl acetate. The extract was dried over anhydrous sodium sulfate, and the solvent was evaporated under reduced pressure. The resulting residue was purified by column chromatography (adsorbent: silica gel, developing solvent: ethyl acetate/hexane) to obtain 7-fluoro-1-isopropyl-6-nitro-carbazole (254 mg, 43%). The resulting 7-fluoro-1-isopropyl-6-nitro-carbazole (500 mg) and Fe (400 mg) were stirred in i-PrOH/water solvent (1:1) under reflux. The reaction mixture was extracted with ethyl acetate and dried over anhydrous sodium sulfate, and the solvent was evaporated under reduced pressure. The resulting residue was purified by column chromatography (adsorbent: silica gel, developing solvent: ethyl acetate/hexane) to obtain 6-amino-7-fluoro-isopropyl-carbazole (290 mg, 65%). The resulting amino compound (500 mg) was dissolved in chloroform (10 ml), and the solution was added dropwise with phenyl chloroformate (190 mg) and stirred for 2 hours. The reaction mixture was added with water and extracted. The extract was dried over anhydrous sodium sulfate, and the solvent was evaporated under reduced pressure. The resulting residue was purified by column chromatography (adsorbent: silica gel, developing solvent: ethyl acetate/hexane) to obtain phenylurethane (263 mg, 61%).

The resulting phenylurethane (900 mg) and (4-pyridino) ethylamine (400 mg) were dissolved in acetonitrile (15 ml) and refluxed for 2 hours. The reaction mixture was added with water and extracted. The extract was dried over anhydrous sodium sulfate, and the solvent was evaporated under reduced pressure. The residue obtained was purified by column chromatography (adsorbent: silica gel, developing solvent: ethyl acetate/hexane) to obtain Compound 12-1 (814 mg, 81%).

$^1$H-NMR (300 MHz, CDCl$_3$) δ1.53–1.57 (m, 6H), 1.77–1.93 (m, 4H), 2.68–2.73 (m, 4H), 2.97 (t, 2H), 3.01 (s, 3H), 3.68 (t, 2H), 4.50 (Sept, 1H), 6.39 (d, 1H), 7.15 (d, 1H), 7.22 (d, 2H), 7.98 (d, 1H), 8.55 (d,2H)

FAB-MS (m/e) 409 (M+H)$^+$

Example 157

Synthesis of Compound 12-2

N-isopropyl-6-nitro-8-fluoro-1,2,3,4-tetrahydrocarbazole was synthesized as in Example 70 by using 2-fluoro-4-nitrophenylhydrazine according to the method described in Journal of Chemical Society, p.833 (1924). Compound 12-2 was synthesized in the same manner as the syntheses in Examples 71, 72 and 102.

$^1$H-NMR (300 MHz, CDCl$_3$) δ1.50 (d, 6H), 1.75–1.95 (m, 4H), 2.68–2.73 (m, 4H), 2.93 (t, 2H), 2.97 (s, 3H), 3.65 (t, 2H), 4.65 (Sept, 1H), 6.17 (br, 1H), 6.87 (dd, 1H), 7.10 (d, 1H), 7.20 (d, 2H), 8.54 (d, 2H)

FAB-MS (m/e) 408 M$^+$

Example 158

Synthesis of Compound 12-3

Phenyl thiochloroformate was used instead of the phenyl chloroformate in the procedure of Example 72, and Compound 12-3 was synthesized in the same manner as in Example 102.

$^1$H-NMR (300 MHz, CDCl$_3$) δ1.59 (d, 6H), 1.80–2.00 (m, 4H), 2.68–2.73 (m, 4H), 3.09 (t, 2H), 3.15 (s, 3H), 4.16 (t, 2H), 4.65 (Sept, 1H), 6.86 (dd, 1H), 7.19 (s, 1H), 7.25 (d, 2H), 7.29 (d, 1H), 7.38 (d, 2H), 8.54 (d,2H)

FAB-MS (m/e) 406 M$^+$

Test Example 1
Y5 Receptor Binding Inhibition Test

Human Y5 receptor gene was isolated based on its cDNA sequence (Nature, 382, p.168 (1996)) by amplifying a gene fragment through PCR and introducing the fragment into expression vector pcDNA3. The sequence of human Y5 gene obtained was analyzed by using ABI PRISM Dye Terminatior Kit (Perkin-Elmer) and verified that the resulting sequence was correct. Expression of the human Y5 receptor was carried out by using a Baculovirus expression system. A recombinant virus containing the human Y5 gene was prepared by using a Baculovirus expression system kit (Life Technologies). High Five insect cells was infected with the virus to allow expression of human Y5 receptor in a large amount.

A membrane prepared from the insect cells in which the human Y5 receptor was expressed was incubated with a test compound (10 μM) and $^3$H-NPY (Amersham Pharmacia Biotech) at 4° C. for 2 hours in an assay buffer (50 mM HEPES buffer containing 1 mM magnesium chloride, 0.25 mg/ml bacitracin, 10 μg/ml leupeptin, 1 μg/ml evelactone B and 1% fetal bovine serum albumin, pH 7.4). Recovery of radioactivity bound to the membrane was performed by the filtration method using a 96-hole Unifilter. Specific binding to human Y5 receptor was obtained by an amount of binding which was antagonized upon addition of excess cold NPY. The results are shown in Table 1. In the table, inhibitory ratios are indicated as inhibitory ratios (%) of test compounds based on amounts of Y5 specific bindings in a group treated with a solvent.

TABLE 1

| Test compound | % Inhibition ratio (10 μM) | Test compound | % Inhibition ratio (10 μM) |
|---|---|---|---|
| Compound 1-1 | 95 | Compound 1-39 | 80 |
| Compound 1-2 | 91 | Compound 1-40 | 91 |
| Compound 1-3 | 78 | Compound 1-41 | 52 |
| Compound 1-4 | 100 | Compound 1-42 | 74 |
| Compound 1-5 | 98 | Compound 1-43 | 54 |
| Compound 1-6 | 93 | Compound 1-44 | 69 |
| Compound 1-7 | 100 | Compound 1-45 | 87 |
| Compound 1-8 | 100 | Compound 1-46 | 102 |
| Compound 1-9 | 100 | Compound 1-47 | 100 |
| Compound 1-10 | 99 | Compound 1-48 | 96 |
| Compound 1-11 | 103 | Compound 1-49 | 91 |
| Compound 1-12 | 77 | Compound 1-50 | 89 |
| Compound 1-13 | 109 | Compound 1-51 | 80 |
| Compound 1-14 | 106 | Compound 1-52 | 88 |
| Compound 1-15 | 111 | Compound 1-53 | 66 |
| Compound 1-16 | 94 | Compound 1-54 | 88 |
| Compound 1-17 | 93 | Compound 1-56 | 94 |
| Compound 1-18 | 88 | Compound 1-57 | 89 |
| Compound 1-19 | 84 | Compound 1-58 | 66 |
| Compound 1-20 | 86 | Compound 1-59 | 93 |
| Compound 1-21 | 97 | Compound 1-60 | 86 |
| Compound 1-22 | 89 | Compound 1-61 | 77 |
| Compound 1-23 | 77 | Compound 1-62 | 50 |
| Compound 1-24 | 98 | | |
| Compound 1-25 | 100 | Compound 2-1 | 71 |
| Compound 1-26 | 82 | Compound 2-4 | 85 |
| Compound 1-27 | 96 | Compound 2-6 | 67 |
| Compound 1-28 | 100 | | |
| Compound 1-29 | 89 | Compound 3-1 | 88 |
| Compound 1-30 | 99 | Compound 3-2 | 94 |
| Compound 1-31 | 94 | Compound 3-3 | 89 |
| Compound 1-32 | 97 | Compound 3-4 | 96 |
| Compound 1-33 | 82 | Compound 3-5 | 100 |
| Compound 1-34 | 88 | Compound 3-6 | 91 |
| Compound 1-35 | 75 | Compound 3-7 | 95 |
| Compound 1-36 | 92 | Compound 3-8 | 73 |

TABLE 2

| Test compound | % Inhibition ratio (10 μM) | Test compound | % Inhibition ratio (10 μM) |
|---|---|---|---|
| Compound 4-1 | 85 | Compound 7-4 | 90 |
| Compound 4-2 | 89 | Compound 7-5 | 100 |
| Compound 4-3 | 99 | Compound 7-6 | 88 |
| Compound 4-4 | 98 | Compound 7-7 | 97 |
| Compound 4-5 | 102 | Compound 7-8 | 97 |
| Compound 4-6 | 99 | Compound 7-9 | 91 |

TABLE 2-continued

| Test compound | % Inhibition ratio (10 μM) | Test compound | % Inhibition ratio (10 μM) |
|---|---|---|---|
| Compound 4-7 | 93 | Compound 7-10 | 97 |
| Compound 4-8 | 84 | Compound 7-11 | 95 |
| Compound 4-9 | 86 | Compound 7-12 | 94 |
| Compound 4-10 | 92 | Compound 7-13 | 83 |
|  |  | Compound 7-14 | 96 |
| Compound 5-1 | 90 | Compound 7-15 | 88 |
| Compound 5-2 | 97 | Compound 7-16 | 96 |
| Compound 5-3 | 98 | Compound 7-17 | 99 |
| Compound 5-4 | 101 | Compound 7-18 | 92 |
| Compound 5-5 | 82 | Compound 7-19 | 75 |
| Compound 5-6 | 89 | Compound 7-20 | 89 |
| Compound 5-7 | 100 | Compound 7-21 | 80 |
| Compound 5-8 | 75 | Compound 7-22 | 86 |
| Compound 5-9 | 98 |  |  |
| Compound 5-10 | 104 | Compound 8-1 | 82 |
| Compound 5-11 | 97 | Compound 8-2 | 95 |
| Compound 5-12 | 100 | Compound 8-3 | 101 |
| Compound 5-13 | 98 | Compound 8-4 | 98 |
| Compound 5-14 | 95 | Compound 8-5 | 85 |
| Compound 5-15 | 87 | Compound 8-6 | 100 |
| Compound 5-16 | 86 | Compound 8-7 | 100 |
| Compound 5-17 | 100 | Compound 8-8 | 73 |
| Compound 5-18 | 100 | Compound 8-9 | 101 |
| Compound 5-19 | 100 | Compound 8-10 | 78 |
| Compound 5-20 | 103 | Compound 8-11 | 102 |
| Compound 5-21 | 99 |  |  |
| Compound 5-22 | 100 | Compound 9-1 | 96 |
| Compound 5-23 | 98 | Compound 9-2 | 78 |
| Compound 5-24 | 95 |  |  |
| Compound 5-25 | 101 | Compound 10-1 | 100 |
| Compound 5-26 | 108 | Compound 10-2 | 83 |
|  |  | Compound 10-3 | 95 |
| Compound 6-1 | 94 | Compound 10-4 | 94 |
| Compound 6-2 | 86 |  |  |
| Compound 6-3 | 102 | Compound 11-1 | 100 |
|  |  | Compound 11-2 | 96 |
| Compound 7-1 | 92 | Compound 11-3 | 100 |
| Compound 7-2 | 99 | Compound 11-4 | 97 |
| Compound 7-3 | 98 |  |  |
|  |  | Compound 12-1 | 100 |
|  |  | Compound 12-2 | 96 |
|  |  | Compound 12-3 | 97 |

Test Example 2
Animal Test for Ingestion Behavior Induced by NPY

Male ddY mice (5-week old, 25–35 g) were fixed under no anesthetization, and administered with neuropeptide Y (human/rat NPY, 300 pmol/mouse) at lateral ventricle (at 1.0 mm on the right of bregma) using a two-stage needle (2.5 mm). Each test compound was dissolved in distilled water and orally administered 1 hour before the administration of NPY. Ingestion amount was measured for 4 hours after the NPY administration. The compounds of the present invention significantly suppressed the ingestion induced by NPY compared with the control group in which only distilled water was orally administered.

Test Example 3
Animal Test for Ingestion Behavior Induced by Starvation

Male ddY mice (5-week old, 25–35 g) were starved from the noon of one day before the day of experiment and feeding was restarted 24 hours later. Each test compound was dissolved in distilled water and orally administered 1 hour before the restart of feeding. Ingestion amount was measured for 4 hours after the restart of feeding. The compounds of the present invention significantly suppressed the ingestion induced by starvation compared with the control group in which only distilled water was orally administered.

Test Example 4
Continuous Administration Test for Animals with Obesity

Male ob/ob mice (8-week old, 41 to 53 g) were orally administered with a test compound every day at a frequency of twice a day for 2 weeks, and ingestion amount was measured. The compounds of the present invention significantly suppressed ingestion compared with the control group in which only distilled water was orally administered. Moreover, when blood parameters were measured at the end of the continuous administration, the compounds of the present invention was found to reduced glucose, insulin, lipid and corticosterone levels compared with the control group in which only distilled water was orally administered.

Industrial Applicability

The compounds represented by the general formulas (I) or (IV) according to the present invention are useful as ingestion controlling agents for diseases in which NPY is involved, in particular, various diseases in which NPY/Y5 receptor is involved, e.g., hyperphagia, inappetence of cancer patients and the like, and also are useful as active ingredients of medicaments for therapeutic and/or prophylactic treatment of central system diseases such as melancholia, epilepsy and dementia, and metabolic diseases such as obesity, diabetes, hypercholesterolemia, hyperlipidemia, arteriosclerosis and hormone abnormality and the like.

What is claimed is:

1. A compound represented by the following general formula (XXI), or a salt thereof:

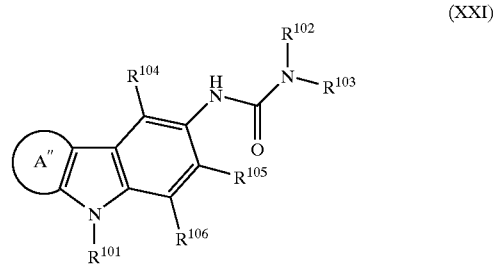

(XXI)

wherein:

A″ represents a ring of the following formula:

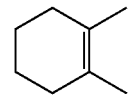

where said ring may have one or more substituents selected from lower alkyl groups, lower alkoxy groups and halogen atoms, and where the lower alkyl and lower alkoxy groups may have one or more substituents;

$R^{101}$ represents a lower alkyl group or a lower acyl group, which groups may contain a ring structure, and may have one or more substituents;

$R^{102}$ represents a hydrogen atom or an alkyl group having a total of 1 to 20 carbon atoms, which alkyl group may contain a ring structure, and may have one or more substituents;

$R^{103}$ represents an alkyl group having a total of 1 to 20 carbon atoms, which alkyl group may contain a ring structure, and may have one or more substituents; and $R^{102}$ and $R^{103}$, together with the nitrogen atom to which they are bonded, may form a ring, which ring may contain one or more hetero atoms as ring members in addition to the nitrogen atom to which $R^{102}$ and $R^{103}$ are bonded, and which ring may have one or more substituents; and $R^{104}$, $R^{105}$ and $R^{106}$ each independently represent a substituent selected from a hydrogen atom, a hydroxyl group, a lower alkyl group, a lower acyl group, a lower alkoxy group, a halogen atom, an amino group, a mono(lower alkyl)amino group, a di(lower alkyl)amino group, a lower acylamino group and an amido group, which substituent may have one or more substituents.

2. The compound or the salt thereof according to claim 1, wherein $R^{101}$ is a lower alkyl group which may contain a ring structure, and may have one or more substituents.

3. The compound or the salt thereof according to claim 1, wherein $R^{103}$ is an alkyl group having one or more substituents containing one or more hetero atoms selected from a nitrogen atom, an oxygen atom and a sulfur atom.

4. The compound or the salt thereof according to claim 3, wherein the one or more substituents of the alkyl group represented by $R^{103}$ are selected from a hydroxyl group, an amino group, a cyano group, a carbamoyl group, a sulfamoyl group, a lower alkoxy group, a lower alkylthio group, a lower alkylsulfonylamino group, a lower alkylcarbonylamino group, a hydroxyalkyl group, a hydroxyalkyloxy group, an alkoxyalkyloxy group, a monoalkylamino group, a dialkylamino group, a lower alkylsulfonylaminoalkoxy group, a lower alkylcarbonylaminoalkoxy group, a lower alkylsulfonylaminoalkylthio group, a lower alkylcarbonylaminoalkylthio group, a tetrazolyl group, a triazolyl group, an imidazolyl group, a pyridyl group, a morpholinyl group, a morpholino group, a thiomorpholino group, a piperazino group, a piperazinyl group, a piperidino group, a piperidinyl group, a pyrrolidinyl group, a triazolylthio group and an imidazolylthio group.

5. The compound or the salt thereof according to claim 1, wherein $R^{101}$ is a lower alkyl group, $R^{102}$ is an alkyl group, and $R^{103}$ is an alkyl group having a substituent selected from a hydroxyl group, an amino group, a cyano group, a carbamoyl group, a sulfamoyl group, a lower alkoxy group, a lower alkylthio group, a lower alkylsulfonylamino group, a lower alkylcarbonylamino group, a hydroxyalkyl group, a hydroxyalkyloxy group, an alkoxyalkyloxy group, a monoalkylamino group, a dialkylamino group, a lower alkylsulfonylaminoalkoxy group, a lower alkycarbonylaminoalkoxy group, a lower alkylsulfonylaminoalkylthio group, a lower alkylcarbonylaminoalkylthio group, a tetrazolyl group, a triazolyl group, an imidazolyl group, a pyridyl group, a morpholinyl group, a morpholino group, a thiomorpholino group, a piperazino group, a piperazinyl group, a piperidino group, a piperidinyl group, a pyrrolidinyl group, a triazolylthio group and an imaidazolylthio group.

6. The compound or the salt thereof according to claim 5, wherein $R^{103}$ is a pyridylalkyl group.

7. The compound or the salt thereof according to claim 6, wherein $R^{101}$ is an isopropyl group, $R^{102}$ is a methyl group, and $R^{103}$ is a pyridylethyl group.

8. The compound or the salt thereof according to claim 7, wherein the pyridylethyl group is a 2-(4-pyridyl)ethyl group.

9. The compound or the salt thereof according to claim 1, wherein the ring formed by $R^{102}$ and $R^{103}$ is a ring represented by the general formula (XXII):

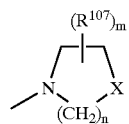

(XXII)

wherein

X represents —$CH_2$—, —O—, —S—, —NH— or —$NR^{108}$—, and $R^{108}$ is a lower alkyl group, a lower acyl group, a phenyl group or a heterocyclic group, where said lower alkyl, lower acyl, phenyl and heterocyclic groups may have one or more substituents;

n represents an integer of from 1 to 4;

$R^{107}$ represents a hydroxyl group, an amino group, a cyano group, a lower alkyl group, a lower alkoxy group, a lower alkylthio group, a lower alkylcarbonyl group, where said lower alkyl, lower alkoxy, lower alkylthio and lower alkylcarbonyl groups may contain a ring structure, and may have one or more substituents, an aryl group which may have one or more substituents, or a heterocyclic group;

m represents 0 or an integer of from 1 to 4, provided that for $m \geq 2$, the groups $R^{107}$ may be the same or different.

10. The compound or the salt thereof according to claim 9, wherein X is —$CH_2$—, —O— or —S—.

11. A medicament comprising as an active ingredient at least one of a compound according to claim 1, a physiologically acceptable salt thereof, a hydrate thereof and a solvate thereof.

12. A medicament comprising as an active ingredient at least one of a compound according to claim 2, a physiologically acceptable salt thereof, a hydrate thereof and a solvate thereof.

13. A medicament comprising as an active ingredient at least one of a compound according to claim 3, a physiologically acceptable salt thereof, a hydrate thereof and a solvate thereof.

14. A medicament comprising as an active ingredient at least one of a compound according to claim 4, a physiologically acceptable salt thereof, a hydrate thereof and a solvate thereof.

15. A medicament comprising as an active ingredient at least one of a compound according to claim 5, a physiologically acceptable salt thereof, a hydrate thereof and a solvate thereof.

16. A medicament comprising as an active ingredient at least one of a compound according to claim 6, a physiologically acceptable salt thereof, a hydrate thereof and a solvate thereof.

17. A medicament comprising as an active ingredient at least one of a compound according to claim 7, a physiologically acceptable salt thereof, a hydrate thereof and a solvate thereof.

18. A medicament comprising as an active ingredient at least one of a compound according to claim 8, a physiologically acceptable salt thereof, a hydrate thereof and a solvate thereof.

19. A method of controlling ingestion, wherein the method comprises administering to a subject in need thereof an effective amount of at least one of a compound according to claim 1, a physiologically acceptable salt thereof, a hydrate thereof and a solvate thereof.

20. A method of controlling ingestion, wherein the method comprises administering to a subject in need thereof an effective amount of at least one of a compound according to claim 8, a physiologically acceptable salt thereof, a hydrate thereof and a solvate thereof.

21. A method of treating diabetes, wherein the method comprises administering to a subject in need thereof an effective amount of at least one of a compound according to claim 1, a physiologically acceptable salt thereof, a hydrate thereof and a solvate thereof.

22. A method of treating diabetes, wherein the method comprises administering to a subject in need thereof an effective amount of at least one of a compound according to claim 8, a physiologically acceptable salt thereof, a hydrate thereof and a solvate thereof.

23. A method of treating at least one of hypercholesterolemia, hyperlipidemia and arteriosclerosis, wherein the method comprises administering to a subject in need thereof an effective amount of at least one of a compound according to claim 1, a physiologically acceptable salt thereof, a hydrate thereof and a solvate thereof.

24. A method of treating at least one of hypercholesterolemia, hyperlipidemia or arteriosclerosis, wherein the method comprises administering to a subject in need thereof an effective amount of at least one of a compound according to claim 8, a physiologically acceptable salt thereof, a hydrate thereof and a solvate thereof.

25. The compound or the salt thereof according to claim 1, which is a ligand for a neuropeptide Y receptor.

26. A process for the manufacture of a medicament, wherein the process comprises combining a pharmaceutically acceptable carrier with at least one of a compound according to claim 1, a physiologically acceptable salt thereof, a hydrate thereof and a solvate thereof.

27. A process for the manufacture of a medicament, wherein the process comprises combining a pharmaceutically acceptable carrier with at least one of a compound according to claim 8, a physiologically acceptable salt thereof, a hydrate thereof and a solvate thereof.

* * * * *